United States Patent
Lin et al.

(10) Patent No.: US 10,121,267 B2
(45) Date of Patent: Nov. 6, 2018

(54) SPECTRAL ESTIMATION AND POLY-ENERGETIC RECONSTRUCTION METHODS AND X-RAY SYSTEMS

(71) Applicant: Duke University, Durham, NC (US)

(72) Inventors: Yuan Lin, Durham, NC (US); Ehsan Samei, Durham, NC (US)

(73) Assignee: Duke University, Durham, NC (US)

( * ) Notice: Subject to any disclaimer, the term of this patent is extended or adjusted under 35 U.S.C. 154(b) by 34 days.

(21) Appl. No.: 15/313,239

(22) PCT Filed: Jun. 30, 2015

(86) PCT No.: PCT/US2015/038414
§ 371 (c)(1),
(2) Date: Nov. 22, 2016

(87) PCT Pub. No.: WO2016/003957
PCT Pub. Date: Jan. 7, 2016

(65) Prior Publication Data
US 2017/0186195 A1 Jun. 29, 2017

Related U.S. Application Data

(60) Provisional application No. 62/020,461, filed on Jul. 3, 2014.

(51) Int. Cl.
*G06K 9/00* (2006.01)
*G06T 11/00* (2006.01)
(Continued)

(52) U.S. Cl.
CPC .......... *G06T 11/008* (2013.01); *A61B 6/032* (2013.01); *A61B 6/482* (2013.01); *A61B 6/50* (2013.01);
(Continued)

(58) Field of Classification Search
CPC .............................. G01N 2223/401
See application file for complete search history.

(56) References Cited

U.S. PATENT DOCUMENTS 5,647,018 A * 7/1997 Benjamin ............. G06T 11/006
250/398
9,865,067 B2 * 1/2018 Highnam ............. G06T 11/008
(Continued)

OTHER PUBLICATIONS

International Preliminary Report on Patentability dated Mar. 1, 2017 from International Application No. PCT/US2015/038414.
(Continued)

*Primary Examiner* — Oneal R Mistry
(74) *Attorney, Agent, or Firm* — Olive Law Group, PLLC

(57) ABSTRACT

Spectral estimation and poly-energetic reconstructions methods and x-ray systems are disclosed. According to an aspect, a spectral estimation method includes using multiple, poly-energetic x-ray sources to generate x-rays and to direct the x-rays towards a target object. The method also includes acquiring a series of poly-energetic measurements of x-rays from the target object. Further, the method includes estimating cross-sectional images of the target object based on the poly-energetic measurements. The method also includes determining path lengths through the cross-sectional images. Further, the method includes determining de-noised poly-energetic measurements and de-noised path lengths based on the acquired poly-energetic measurements and the determined path lengths. The method also includes estimating spectra for angular trajectories of a field of view based on the de-noised poly-energetic measurements and the path lengths.

19 Claims, 64 Drawing Sheets

(51) Int. Cl.
*G01T 1/16* (2006.01)
*A61B 6/00* (2006.01)
*A61B 6/03* (2006.01)

(52) U.S. Cl.
CPC .......... *A61B 6/5205* (2013.01); *A61B 6/5258* (2013.01); *A61B 6/5282* (2013.01); *G01T 1/16* (2013.01); *G06T 11/005* (2013.01); *G06T 11/006* (2013.01); *G01N 2223/401* (2013.01); *G01N 2223/419* (2013.01); *G06T 2211/408* (2013.01); *G06T 2211/424* (2013.01)

(56) References Cited

U.S. PATENT DOCUMENTS

| | | |
|---|---|---|
| 2006/0072800 A1 | 4/2006 | Bernard Deman et al. |
| 2008/0095302 A1 | 4/2008 | Ruhrnschopf et al. |
| 2012/0093285 A9 | 4/2012 | Ren et al. |
| 2012/0219200 A1 | 8/2012 | Reeves et al. |
| 2012/0265050 A1* | 10/2012 | Wang ..................... A61B 5/055 600/411 |
| 2013/0112874 A1* | 5/2013 | Osvath ................... A61B 6/486 250/311 |
| 2013/0343624 A1 | 12/2013 | Thibault et al. |
| 2014/0121527 A1 | 5/2014 | Adler, Jr. et al. |
| 2014/0328453 A1* | 11/2014 | Hsieh ..................... A61B 6/035 378/16 |
| 2014/0341333 A1* | 11/2014 | Wang ..................... A61B 6/032 378/19 |
| 2015/0302634 A1* | 10/2015 | Florent .................. G06T 7/30 345/419 |

OTHER PUBLICATIONS

International Search Report and Written Opinion for PCT/US2015/038414 dated Jan. 7, 2016.

* cited by examiner

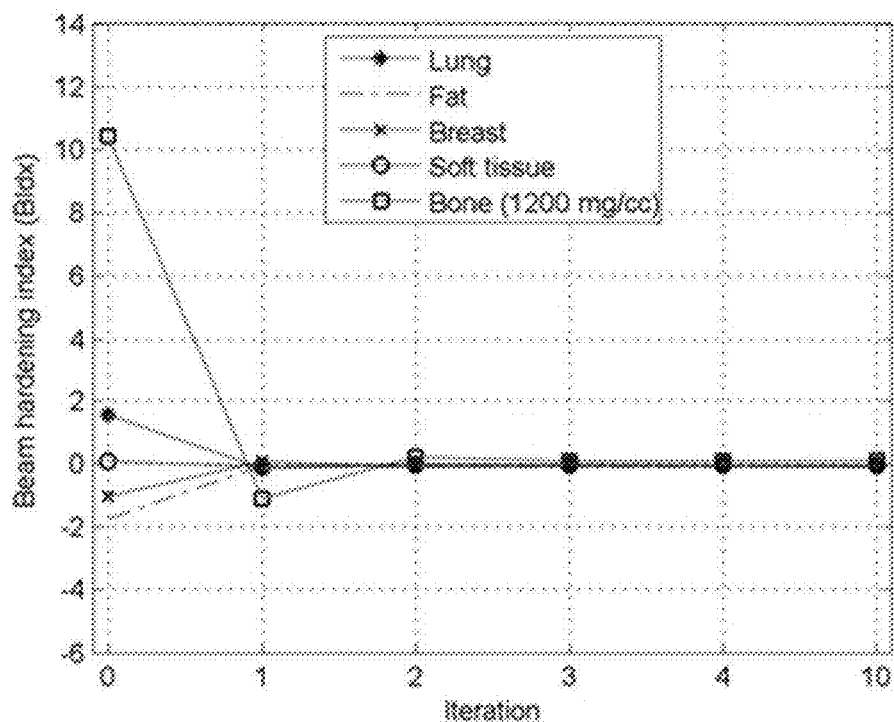
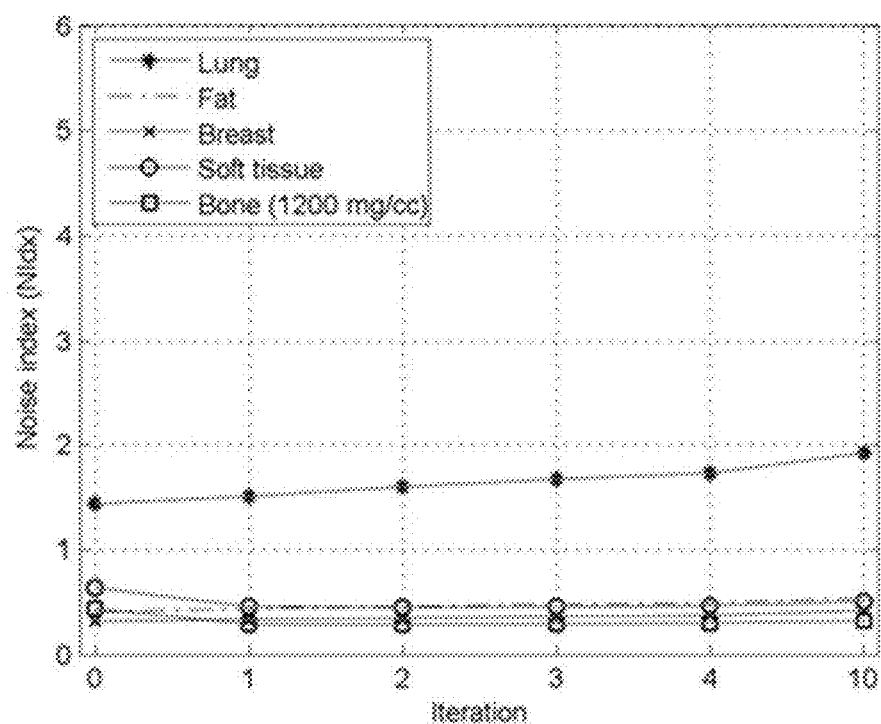
FIG. 5B

Examples of collimators and blockers
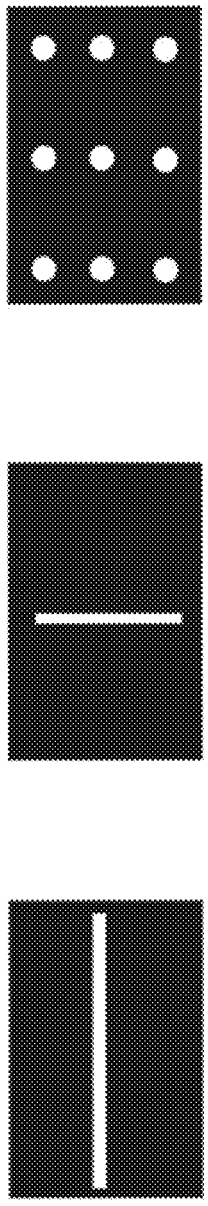
Examples of target objects made of a single material (left) and multiple materials (right)
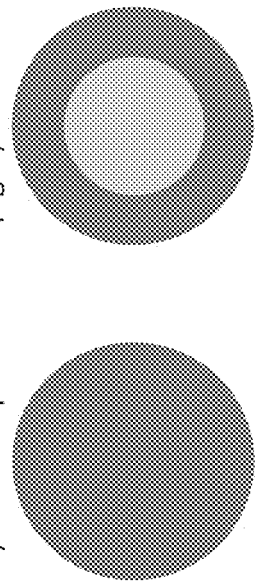
Examples of target objects
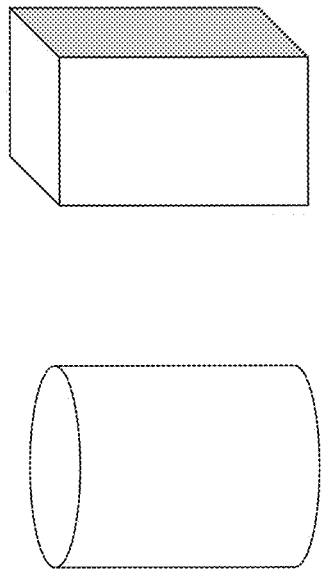
FIG. 55

__US 10,121,267 B2__

SPECTRAL ESTIMATION AND POLY-ENERGETIC RECONSTRUCTION METHODS AND X-RAY SYSTEMS

CROSS REFERENCE TO RELATED APPLICATION

This is a 371 national stage patent application which claims priority to PCT International Patent Application No. PCT/US15/38414, filed Jun. 30, 2015, and titled SPECTRAL ESTIMATION AND POLY-ENERGETIC RECONSTRUCTION METHODS AND X-RAY SYSTEMS, which claims priority to U.S. Provisional Patent Application No. 62/020,461, filed Jul. 3, 2014 and titled SYSTEMS AND METHODS FOR QUANTITATIVE POLY-ENERGETIC RECONSTRUCTION SCHEMES FOR SINGLE SPECTRUM CT SCANNERS; the entire contents of which are incorporated herein by reference herein in their entireties.

TECHNICAL FIELD

The presently disclosed subject matter relates to x-ray imaging. Particularly, the presently disclosed subject matter relates to poly-energetic reconstruction methods for x-ray imaging modalities.

BACKGROUND

For many commercially available CT scanners, the photons emitted from the X-ray source spread within a wide and continuous distribution of energy spectrum. As a poly-energetic X-ray beam passes through matter, lower-energy photons are preferentially absorbed compared to higher-energy photons; the beam gradually becomes harder as its mean energy increases. This phenomenon leads to various well-known beam-hardening (BH) artifacts, such as cupping and streaks, which affect the voxel values in the reconstructed image, and make the quantitative evaluation of attenuation properties challenging.

Ever since the first clinical CT scanner in 1967, numerous efforts have been made to address this challenge via poly-energetic reconstruction. These methods aim to incorporate the energy-dependent nonlinearity of the attenuation coefficient into the reconstruction process without a dramatic increase in computational complexity. Generally speaking, these methods can be divided into three categories.

The first category is filtered backprojection (FBP)-based linearization approaches, which aim to correct the raw measurements according to the water's or bone's X-ray attenuation characteristics prior to the FBP reconstruction. For example, a reconstruction technique (i.e., water correction) was previously developed to compensate for the water-related cupping artifacts. However, this technique is limited to soft tissue, and for inhomogeneous objects (especially in the presence of bone), BH artifacts are still significant. Later, a bone correction technique was developed for X-ray images. However, this technique requires a threshold-based segmentation process for the initial reconstructed images, which restricts its quantitative performance.

The second category is iterative-based base material approaches, which assume that the target volume consists of N known base materials, and use a linear combination of the known energy dependences to approximate the energy dependence of the attenuation coefficient in each voxel. Base material approaches are a more accurate alternative to the linearization approaches, but limited base materials have been incorporated due to expensive computation. For example, a segmentation-free displacement model was developed that accounts for soft tissue, bone, and their mixture by their density difference. This technique performs well for these base materials, but is less accurate for fat and breast tissue since their spectral properties deviate from those of the base materials.

In the third category, as an acquisition alternative, the dual energy approaches decompose the attenuation coefficients into components related to photoelectric absorption and Compton scattering. With the dual energy projection datasets, the nonlinear intensity measurements can be transformed to two simple linear integrals of the component coefficients, and the FBP can be used to reconstruct the unknown object. However, this technique requires two scans at different kVps and a sophisticated hardware setup, such as dual-energy X-ray tubes, rapid kVp switching, or energy discriminating detectors (either layered detectors or photo counting detectors).

In addition, high concentration iodinated contrast agent can also induce strong beam hardening artifacts. Some efforts have been made to account for the attenuation properties iodine, but with limited success. For example, an image-based beam hardening correction algorithm was developed to incorporate the attenuation properties of water, bone and iodine in terms of effective density. However, a pre-requisite of this technique is to accurately segment these three base materials into distinct regions. Also, a technique was developed to distinguish the three regions by measuring the voxel dynamics, but they used a series of threshold-based segmentation techniques, and the voxels containing low concentration or low dynamic iodinated contrast agent could be potentially mis-interpreted as soft tissue or bone minerals. Besides, both of the two techniques are limited to myocardial perfusion exam, as they only model the attenuation properties of blood-iodine mixture. Errors may arise in other perfusion exams, such as lung or breast perfusion exams.

In view of the foregoing, quantitative poly-energetic reconstruction schemes for X-ray imaging modalities is proposed to improve the performance of the X-ray imaging modalities.

SUMMARY

Spectral estimation and poly-energetic reconstructions methods and x-ray systems are disclosed. In aspects of the present disclosure, poly-energetic reconstruction methods are provided for x-ray imaging modalities, which include but are not limited to single spectrum computed tomography (CT), dual-energy CT, photon-counting CT, CT with multiple contrast media, quantitative CT, tomosynthesis, radiography, mammography, and fluoroscopy, etc. The application fields of these X-ray imaging modalities include but are not limited to medical field, industry field, military field, and security check, etc. This application uses a medical single spectrum CT scanner as an exemplary system to explain the methods, and our methods can also be applied with or without variants to the other X-ray imaging modalities and the other application fields. Such that our methods by no means are only limited to the single spectrum CT scanner and the medical field.

According to an aspect, a spectral estimation method includes using multiple, poly-energetic x-ray sources to generate x-rays and to direct the x-rays towards a target object. The method also includes acquiring a series of poly-energetic measurements of x-rays from the target object. Further, the method includes estimating cross-sectional images of the target object based on the poly-energetic measurements. The method also includes determining path lengths through the cross-sectional images. Further, the method includes determining de-noised poly-energetic measurements and de-noised path lengths based on the acquired poly-energetic measurements and the determined path lengths. The method also includes estimating spectra for angular trajectories of a field of view based on the de-noised poly-energetic measurements and the de-noised path lengths.

According to another aspect, a poly-energetic reconstruction method includes providing multiple, acquired poly-energetic measurements, a reference energy for reconstruction, and an initialized reconstruction volume. The method includes providing one or more base material sets. Further, the method includes generating a region map based on a current reconstruction volume. The method also includes decomposing each voxel of the current reconstruction volume into a plurality of base materials in terms of based material path lengths based on the provided reference energy, a voxel value of the reconstruction volume, the region map, and the corresponding base material set. Further, the method includes performing a forward poly-energetic, ray-tracing technique to estimate poly-energetic measurements based on the current reconstruction volume. The method includes subtracting estimated poly-energetic measurements from the acquired poly-energetic measurements to obtain error measurements. Further, the method includes performing a backward updating technique to update the current reconstruction volume based on a difference between the estimated poly-energetic measurements and acquired poly-energetic measurements. The method also includes iterating the steps of providing one or more based material sets, initializing, and generating for one of a predetermined number of iterations or until the reconstruction volume converges and meets predetermined criteria. Further, the method includes transforming the reconstruction volume from the reference energy to the target energy to finalize the reconstruction volume.

According to another aspect, the present disclosure provides three poly-energetic reconstruction methods for X-ray imaging modalities.

According to another aspect, the present disclosure provides an angle-dependent estimation method of CT x-ray spectrum from rotational transmission measurements, thereby enabling estimation of incident spectra across a wide range of angular trajectories with a single phantom and a single axial scan in the absence of knowledge of a bowtie filter.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description server to explain the principles and operation of the concepts disclosed.

BRIEF DESCRIPTION OF THE SEVERAL VIEWS OF THE DRAWINGS

The foregoing aspects and other features of the present subject matter are explained in the following description, taken in connection with the accompanying drawings, wherein:

FIG. 5B illustrates graphs of BIdx and NIdx of algorithm piFBP-WS;

FIG. 55 depicts diagrams of examples of collimators and blockers, target objects as indicated;

DETAILED DESCRIPTION

Figure 1B:
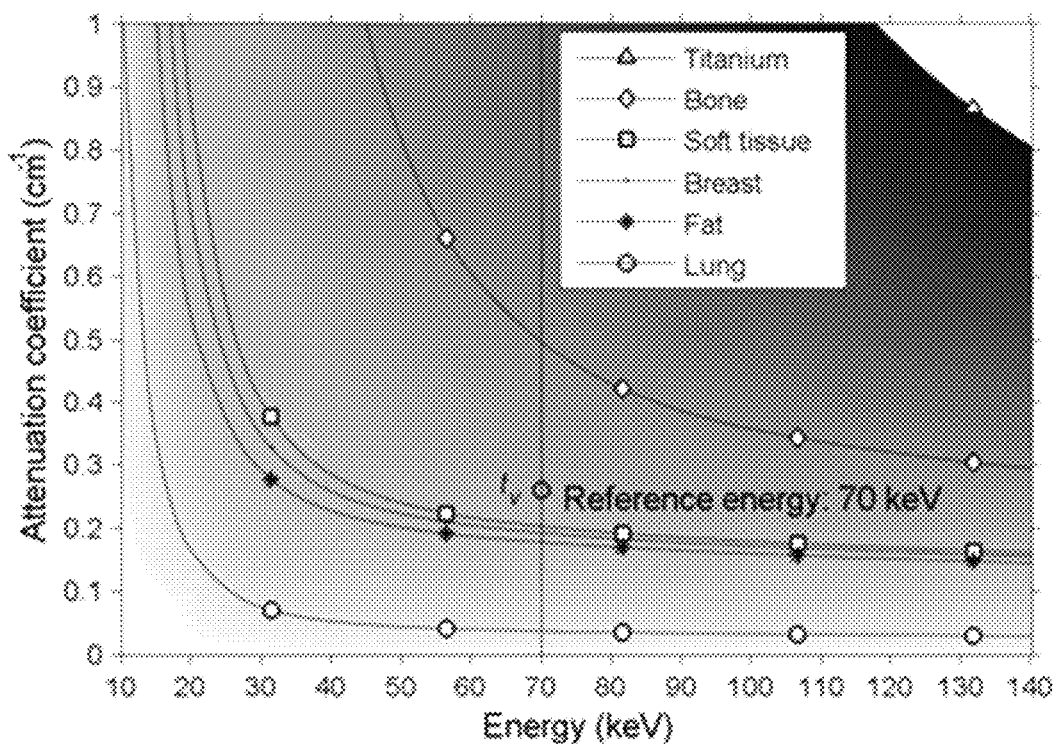
FIGS. 1A and 1B illustrate graphs of different attenuation coefficient curves of base materials for a chest CT exam.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

Beam-hardening effects are mainly caused by the inconsistency between the poly-energetic nature of the x-ray CT system and the mono-energetic nature of the reconstruction algorithms, which can seriously degrade the quality of CT images and result in misdiagnosis. In accordance with embodiments of the present disclosure, several poly-energetic reconstruction methods for CT scanners are provided. In one method, a reconstruction technique, i.e., poly-energetic iterative Filtered Backprojection algorithm (piFBP), can incorporate diverse body tissues (e.g., lung, fat, breast, soft tissue, and bone) and metal implants into the reconstruction process. Artifact-free images can be quickly reconstructed with only four iterations. This method can be applied to general CT exams and quantitative CT exams. If iodinated contrast agent is administered to the patient and pre-contrast projections are not available or useable due to uncorrectable patient motions (e.g., myocardial CT perfusion), another reconstruction algorithm, i.e., poly-energetic Simultaneous Algebraic Reconstruction Technique (pSART), can be applied to account for the attenuation properties of the blood-iodine mixtures. If patient motions are negligible or correctable and the pre-contrast images can be used as prior information, yet another reconstruction algorithm, i.e., poly-energetic dynamic perfusion algorithm (pDP), can be used to account for the attenuation properties of diverse tissue-iodine mixtures and to differentiate bones and iodine without the use of segmentation techniques. Such that reconstruction algorithm pDP can be applied to the other CT perfusion exams, such as lung perfusion, breast perfusion, brain perfusion, and CT angiography, etc.

The poly-energetic reconstruction methods and systems disclosed herein can effectively eliminate beam hardening artifacts caused by bone and iodine, greatly reduce metal artifacts caused by metal implants, and quantitatively reconstruct accurate images with poly-energetic spectrum. Its fast reconstruction speed and excellent performance make it ready for clinical applications on the current CT scanners.

CT performance as well as dose and image quality is directly affected by the x-ray spectrum. However, the current assessment approaches of the CT x-ray spectrum require costly measurement equipment and complicated operational procedures, and are often limited to the spectrum corresponding to the center of rotation. Angle-dependent estimation methods are provided herein for addressing these limitations. Particularly, in methods disclosed herein, incident spectra across a wide range of angular trajectories can be estimated accurately with only a single phantom and a single axial scan in the absence of the knowledge of a bowtie filter.

Beam hardening (BH) is a process whereby the average energy of the x-ray beam increases as the beam propagates through materials, because lower energy photons may be preferentially absorbed compared to the higher energy ones. This nonlinear effect leads to two major visible artifacts, i.e., cupping due to water-related BH and streaks due to bone- or metal-related BH. Besides, this nonlinear effect also influences the voxel values and makes the quantitative evaluation of attenuation properties challenging. Many different solutions are disclosed herein in accordance with embodiments of the present disclosure to eliminate the BH effect, and they can be broadly divided into three categories, i.e., FBP-based linearization approaches, iterative-based base material approaches, and the dual energy approaches.

Each approach has advantages and disadvantages. Linearization approaches are fast and widely used in the current clinical practice, but can only reduce visible artifacts and have limited quantitative reconstruction abilities. Iterative base material approaches are accurate for base materials, but cannot be widely used for diagnosis due to slow computational speed. The dual energy approaches are fast and accurate, but the sophisticated hardware and cost limit their applications.

The present disclosure provides a fast poly-energetic iterative FBP (iFBP) algorithm (piFBP) for CT, which combines the poly-energetic forward projection process of the iterative approaches with FBP type backward updating process. For the poly-energetic forward projection process, an adaptive attenuation coefficient decomposition method is proposed, which can help incorporate diverse base materials including diverse body tissues (e.g., lung, fat, breast, soft tissue, and bone) and metal implants. For the backward updating process, a new iFBP algorithm with smoothing kernel is proposed to improve the convergence properties. A series of simulations were performed to validate the algorithm.

The symbols and their definitions used throughout this paper are summarized in Table 1.

Iterative algorithms can be viewed as feedback loops in which projections are simulated based on the current estimates (forward projection process) and are compared to the measured projections for the backward error updating (backward projection process). Therefore, faithfully simulating the transmission process of the x-ray beam in the forward projection process and efficiently updating the errors in the backward projection process are two requirements of a poly-energetic reconstruction algorithm. To meet these requirements, poly-energetic forward projection methods and iFBP backward projection methods were developed as set forth herein.

The forward projection model for the poly-energetic x-ray beam is given by $$\bar{p}_r = -\ln(\int I(E)\exp[-\int_{L_r}\mu(\vec{x},\varepsilon)dl]d\varepsilon)(r=1,\ldots,NR), \quad (1)$$

where $\bar{p}_r$ is the logarithmic estimation along the rth ray line $L_r$, $N_R$ is the total number of the ray paths from the x-ray source to the detector elements, $I(\varepsilon)$ is the spectrum (normalized to unit area), and $\mu(\vec{x},\varepsilon)$ is the unknown spatial- and energetic-related attenuation map of the object. In order to reduce the free degrees of the attenuation map $\mu(r,\varepsilon)$ and to facilitate the evaluation of this nonlinear double integral, the following adaptive base material decomposition method is provided.

TABLE 1

Symbols and definitions.

| Symbols | Definitions |
|---|---|
| $\mathcal{B}$ | Filtered backward projection (FBP) operator |
| $\mathcal{F}(\mathcal{F}_w)$ | Logarithmic poly-energetic forward projection operator (with water correction) |
| $I_e$ | X-ray photon intensity at the e-th energy bin |
| $I(\varepsilon)$ | X-ray photon intensity at energy level $\varepsilon$ |
| N | Total number of the voxels in the measured ROI |
| $N_E$ | Total number of the spectrum energy bins |
| $N_M$ | Total number of the base materials |
| $N_R$ | Total number of the x-ray paths from x-ray source to detector modules |
| $N_V$ | Total number of the voxels of the volume |
| S | Smoothing operator |
| $Y_{rs}$ | CT Measurement through the r-th x-ray with the s-th incident spectrum |
| $a_{vr}$ | Contribution of the v-th voxel to the r-th ray |
| e | Index for spectrum energy bins |
| $l_{mr}$ | Accumulated effective length of the m-th material along the r-th ray |
| $l_r$ | Water equivalent length along the r-th ray |
| m | Index for the base materials |
| $\bar{p}$ ($\bar{p}_w$) | Column vector of logarithmic poly-energetic estimations (after water correction) |
| $p_r$ | Logarithmic measurement along the r-th ray |
| $\bar{p}_r$ | Logarithmic estimation along the r-th ray |
| r | Index for the x-ray paths |
| t | Column vector of voxels of the target volume in terms of the attenuation coefficient at $\varepsilon$ |
| $t_v$ | Attenuation coefficient of the v-th voxel at reference energy $\varepsilon_0$ |
| $t_v^0$ | Theoretical attenuation coefficient of the v-th voxel at reference energy $\varepsilon_0$ |
| $t(\vec{x})$ | Attenuation coefficient at location $\vec{x}$ at reference energy $\varepsilon_0$ |
| v | Index for the voxels |
| $\varepsilon$ | Energy level within the spectrum range |
| $\varepsilon_0$ | Reference energy, at which the mono-energetic image will be reconstructed |
| $\eta_v^b$ | Beam hardening error to the v-th voxel |
| $\eta_v^n$ | Noise error to the v-th voxel |
| $\mu(\vec{x}, \varepsilon)$ | Attenuation coefficient at location $\vec{x}$ at reference energy $\varepsilon$ |
| $\mu_{me}$ | Attenuation coefficient of the m-th base material at the e-th energy bin |
| $\mu_m(\varepsilon)$ | Attenuation coefficient of the m-th base material at energy $\varepsilon$ |
| $\mu_w(\varepsilon)$ | Attenuation coefficient of water at energy $\varepsilon$ |
| $\rho_m$ | Density of the m-th base material |
| $\rho_v$ | Density of the v-th voxel |

Figure 1A:
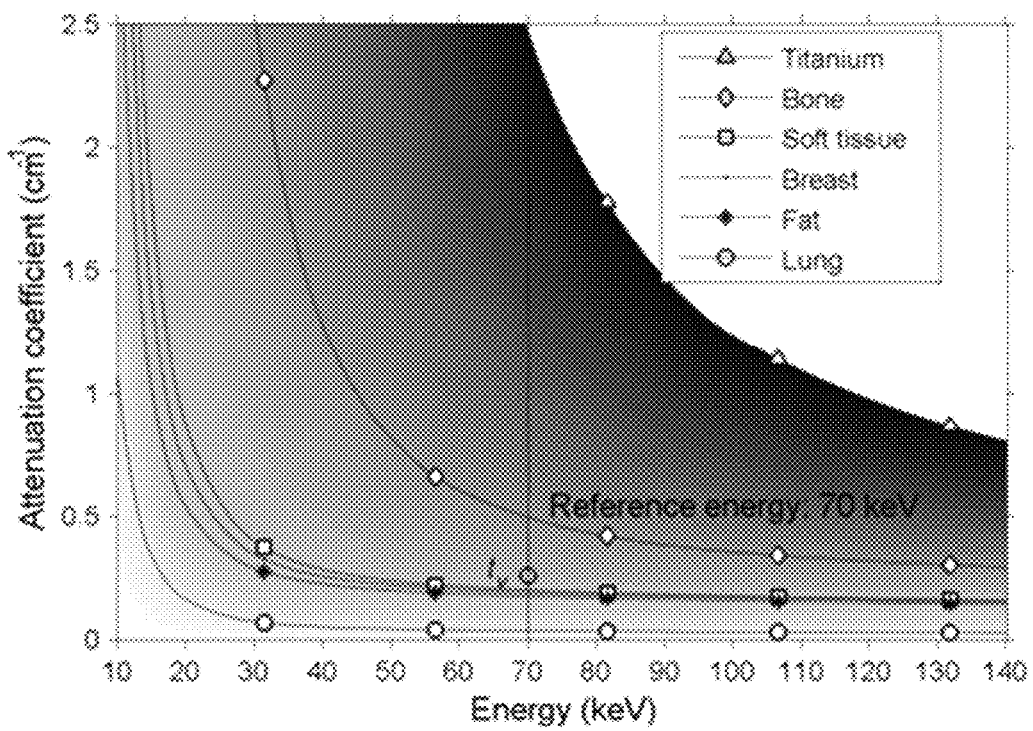

It can be assumed that the object is composed of NM known base materials, and each voxel is a mixture of two base materials. The base material set can be selected according to the CT exams. For example, the base material set for a chest CT exam usually comprises air (m=0), lung (m=1), fat (m=2), breast (m=3), soft tissue (m=4), bone (m=5), and metal implants (m=6), where m is the material index. The attenuation coefficient curves of these base materials are plotted in FIGS. 1A and 1B, which illustrate graphs of different attenuation coefficient curves of base materials for a chest CT exam. More particularly, FIG. 1A shows a plot with large attenuation coefficient range [0.0, 2.5] to facilitate the appreciation of the relative relationship between the high attenuation curves and the low attenuation curves. FIG. 1B shows a plot with small attenuation coefficient range [0.0, 1.0] to facilitate the appreciation of the relative relationship of the low attenuation curves. The gray gradient indicates the interpolated curves along the 70 keV reference energy line. Since previous iterative-based base material approaches can only incorporate one (soft tissue) or two (soft tissue and bone) base materials, errors arise for other materials, such as lung, fat, and breast. Our base material set contains a wide range of materials, so that gradation of attenuation coefficients for various tissue types can be broadly and accurately sampled.

In order to facilitate incorporating the base material set into the forward projection process, the value of the vth voxel $t_v$ (v=1, ..., NV) is defined as the attenuation coefficient at a reference mono-energetic energy of $\varepsilon_0$ (e.g. $\varepsilon_0$=70 keV), where NV is the total number of the unknown voxels. Based on $t_v$, each voxel of mixture can be adaptively decomposed to two adjacent base materials. For instance, if $t_v$ (the circle in FIGS. 1A and 1B) is within the bone interval, i.e., [$\mu_4(\varepsilon_0)$, $\mu_5(\varepsilon_0)$), where $\mu_m(\varepsilon_0)$ is the attenuation coefficient of the mth base material at the reference energy $\varepsilon_0$, then the attenuation coefficient curve for the vth voxel can be estimated as $$\mu(t_v, \varepsilon) = \frac{\mu_5(\varepsilon_0) - t_v}{\mu_5(\varepsilon_0) - \mu_4(\varepsilon_0)}\mu_4(\varepsilon) + \frac{t_v - \mu_4(\varepsilon_0)}{u_5(\varepsilon_0) - \mu_4(\varepsilon_0)}\mu_5(\varepsilon). \quad (2)$$

This expression is defined as a separation model, and the coefficients stand for the base material volume fractions or effective lengths, i.e., for x-ray, the path through the mixture with attenuation coefficient $t_v$ is equivalent to sequential paths through $$\frac{\mu_5(\varepsilon_0) - t_v}{\mu_5(\varepsilon_0) - \mu_4(\varepsilon_0)}$$

soft tissue and $$\frac{t_v - \mu_4(\varepsilon_0)}{\mu_5(\varepsilon_0) - \mu_4(\varepsilon_0)}$$

bone. This decomposition approach transfers the energy dependence to countable base materials and the dependence degrees are reflected by base material effective lengths with attenuation coefficients at preselected reference energy $\varepsilon_0$. This suggests that we can use one forward ray tracing to calculate the energy independent accumulated effective lengths of all base materials, which can then be used repeatedly to estimate the poly-energetic forward projection (Eq. 1).

Equation 2 can also be rewritten into an equivalent mass attenuation coefficient form as $$\mu(t_v, \varepsilon) = \left(\frac{\mu_5(\varepsilon_0) - t_v}{\mu_5(\varepsilon_0) - \mu_4(\varepsilon_0)}\rho_4\right)\left[\frac{\mu(\varepsilon)}{\rho}\right]_4 + \left(\frac{t_v - \mu_4(\varepsilon_0)}{\mu_5(\varepsilon_0) - \mu_4(\varepsilon_0)}\rho_5\right)\left[\frac{\mu(\varepsilon)}{\rho}\right]_5, \quad (3)$$

where $\rho_m$(m=1, ..., $N_M$) is the density of the base materials. The above expression stands for a mixture model, and the coefficients in the round brackets are the base material densities after being mixed. This model is convenient for computing the bone density, $$\rho_v = \frac{t_v - \mu_4(\varepsilon_0)}{\mu_5(\varepsilon_0) - \mu_4(\varepsilon_0)} \times 1920 \text{ mg cc}^{-1}, \quad (4)$$

where 1920 mg cc$^{-1}$ is the density of the bone base material. Bone may be generally considered as a water-calcium solution. For cancellous bone, this solution model is reasonably accurate and can be applied to quantitative CT for bone mineral measurement. For cortical bone, this solution model can lead to significant displacement effect which can be accounted by tabulating the decomposition coefficients in Equation 3 for different density bones. It has been assumed that the displacement effect would be inconsequential and thus the solution model was sufficiently accurate.

A general decomposition equation for the with voxel can be expressed as $$\mu(t_v, \varepsilon) = \sum_{m=0,...,N_M-1} X[\mu_m, \quad (5)$$

$$\mu_{m+1}](t_v)\left[\frac{\mu_{m+1}(\varepsilon_0) - t_v}{\mu_{m+1}(\varepsilon_0) - \mu_m(\varepsilon_0)}\mu_m(\varepsilon) + \frac{t_v - \mu_m(\varepsilon_0)}{\mu_{m+1}(\varepsilon_0) - \mu_m(\varepsilon_0)}\mu_{m+1}(\varepsilon)\right],$$

where the step function $X_{(a,b)}$ is defined as $$X_{[a,b)}(t) = \begin{cases} 1 & t \in [a, b) \\ 0 & t \notin [a, b) \end{cases}$$

For easy observation, the interpolated attenuation curves along the 70 keV reference energy line with Equation 5 is plotted in FIGS. 1A and 1B with a gray gradient. To reduce the computational time, the base material interval indices and the corresponding effective lengths for every voxel can be calculated and stored in matrices before each iteration, with which the accumulated effective lengths of all base materials can be computed through one forward ray tracing as $$\int_{L_r} \mu(t(\vec{x}), \varepsilon)dl \approx \sum_{v=1,...,N_V} a_{rv}\mu(t_v, \varepsilon) = \sum_{m=0,...,N_M} l_{rm}\mu_m(\varepsilon) \quad (7)$$

where $a_{rv}$ denotes the elements of the system matrix, and $l_{rm}$ denotes the accumulated effective length of the m-th material for the r-th ray, $$l_{rm} = \sum_{v=1,...,N_v} a_{rv}X_{[\mu_m,\mu_{m+1})}(t_v) \times \quad (8)$$

$$\begin{cases} \frac{\mu_{m+1}(\varepsilon_0) - t_v}{\mu_{m+1}(\varepsilon_0) - \mu_m(\varepsilon_0)} & m = 0 \\ \frac{\mu_{m+1}(\varepsilon_0) - t_v}{\mu_{m+1}(\varepsilon_0) - \mu_m(\varepsilon_0)} + \frac{t_v - \mu_{m-1}(\varepsilon_0)}{\mu_m(\varepsilon_0) - \mu_{m-1}(\varepsilon_0)} & m = 1, ..., N_M - 1 \\ \frac{t_v - \mu_{m-1}(\varepsilon_0)}{\mu_m(\varepsilon_0) - \mu_{m-1}(\varepsilon_0)} & m = N_M \end{cases}$$

With the accumulated effective length $l_{rm}$, the poly-energetic forward projection equation (Eq. 1) can be easily calculated as $$\bar{p}_r = -\ln\left(\int I(\varepsilon)\exp\left[-\int_{L_r} \mu(t(\vec{x}), \varepsilon)dl\right]d\varepsilon\right) \quad , \quad (9)$$

$$\approx -\ln\left(\sum_{e=1,\ldots,N_E} I_e \exp\left[-\sum_{m=0,\ldots,N_M} l_{rm}\mu_{me}\right]\Delta e\right)$$

where $I_e$ denotes the e-th energy bin (e=1, ..., $N_E$) of the x-ray spectrum and $N_E$ is the total number of the discrete energy bins. For simplicity, Equation 9 can be expressed in a vector notation as $$\bar{p} = \mathcal{F} t, \quad 1$$

where $\bar{p}$ is the column vector containing estimated logarithmic poly-energetic detector values, t is the column vector containing voxels of the target volume in terms of the attenuation coefficient at reference energy $\varepsilon_0$, and $\mathcal{F}$ is the logarithmic poly-energetic forward projection operator.

The backward projection method of piFBP (detailed in the next subsection) may use the conventional water correction technique. The water correction technique assumes that the scanned object is mainly made of water equivalent materials in x-ray attenuation characteristics. Such that, each logarithmic poly-energetic measurement ($p_r$) or estimation ($\bar{p}_r$) corresponds to a water-equivalent length ($l_r$), which can be determined based on an experiment-based lookup table or the following equation $$p_r = -\ln(\int I(e)\exp[-_w(\varepsilon)l_r]d\varepsilon), \quad (2)$$

where $\mu_w(\varepsilon)$ is the attenuation of water. Multiplying $l_r$ with water's attenuation coefficient at preselected reference energy ($\varepsilon_0$) then yields the water corrected measurements as $$p_{w,r} = \mu_w(\varepsilon_0)l_r. \quad (3)$$

If the scanned object is made of water equivalent materials, water correction can completely eliminate the beam hardening artifacts. In the next subsection, $p_w$ may be used to indicate the column vector containing water-corrected logarithmic measurements. The column vector containing water corrected logarithmic poly-energetic forward estimations is correspondingly expressed as $$\bar{p}_w = \mathcal{F}_w t, \quad 4$$

where $\mathcal{F}_w$ is a compound operator consisting of a water correction operation after a logarithmic poly-energetic forward projection operation.

Currently, this water correction technique may be used by a clinical CT scanner use to pre-correct the projection measurements, which are then reconstructed by conventional FBP algorithm. As such, this water-corrected FBP method was used as a major comparison method in our validation section.

Iterative FBP (iFBP) may be used to solve the non-uniform attenuation compensation problem in single-photon emission computed tomography (SPECT). With the poly-energetic forward projection operation described herein, an iterative FBP algorithm can be written as $$piFBP\text{-}W: \begin{cases} t^{(0)} = \mathcal{B} p_w \\ t^{(k+1)} = t^{(k)} + c\mathcal{B}(p_w - \mathcal{F}_w t^{(k)}) \end{cases}, \quad 5$$

where B is the filtered backward projection (FBP) operator, k is the iteration index (k≥0), and c is the relaxation parameter. Herein, the relaxation parameter c may be equal to one. For convenience, the poly-energetic iterative algorithm Equation 14 is named as piFBP-W, where W stands for the water correction in the iterative updating equation.

piFBP-W may use the water-corrected measured projections $p_w$ as the ground truth. If one voxel is underestimated (or overestimated) due to BH effect, the simulated forward projections $\mathcal{F}_w t^{(k)}$ through that voxel are likely to be underestimated (or overestimated) with respect to $p_w$. The differences reflected by the estimated and measured projections may then be backward updated to correct the target volume. Ideally, the image estimates stop changing, i.e., converge to the correct solution, when $$p_w - \mathcal{F}_w t(k) = 0. \quad 6$$

However, the measurement noise in the CT system, such as quantum noise and electronic noise, can be gradually built up in the target volume in each iteration, and finally result in divergent results. So the conventional form Equation 14 may not be used for reconstruction directly.

As BH artifacts are mainly low frequency signals, we propose to use a smoothing operator S to suppress the noise in the correction volume, and improve the convergence stability:

$$piFBP\text{-}WS: \begin{cases} t^{(0)} = \mathcal{B} p_w \\ t^{(k+1)} = t^{(k)} + c\mathcal{S}\mathcal{B}(p_w - \mathcal{F}_w t^{(k)}) \end{cases}. \quad (16)$$

For the smoothing kernel, this study employed a zero-mean 5×5 pixels Gaussian low pass filter with a standard deviation (sigma) of 1.05. As the iterative updating equation in Equation 16 contains both a water correction process and a smoothing kernel, we designate this algorithm as piFBP-WS.

For piFBP-WS, water correction needs to be applied to the simulated poly-energetic projections. The water correction can reduce the nonlinearity of the projections, and benefit the convergence, but it is a time consuming process. Because of monotonicity of the water correction, $p-Ft^{(k)}$ and $p_w - F_w t^{(k)}$ have the same updating direction and slightly different updating step sizes, the water correction process may be omitted in the backward updating equation to reduce computational time. The new poly-energetic reconstruction algorithm designated as piFBP, can then be expressed as $$piFBP: \begin{cases} t^{(0)} = \mathcal{B} p_w \\ t^{(k+1)} = t^{(k)} + c\mathcal{S}\mathcal{B}(p - \mathcal{F} t^{(k)}) \end{cases}. \quad (17)$$

It is shown herein that piFBP-WS has better convergence property than piFBP, but piFBP has a faster reconstruction speed and yields similar images.

Two ideas are worth noting. First, $F_w$ and B are inverse operators of each other when the spectrum is mono-energetic or when the materials in the scanned object are all water equivalent. However, F and B are only inverse operators of each other in the former case. Second, Fourier cut-off frequency and the filter type can lead to a so-called inherent error in the reconstruction process. Using a ram-lak filter during the iterative processes can reduce the inherent error by preserving the high frequency edge information. Otherwise, sharp edges may be blurred by the soft filters, which create inconsistency between estimated and measured projections in the subsequent iterations as edge artifacts.

In experiments, a fan beam with an equiangular are detector row CT geometry was simulated. Two phantoms (a simple oval phantom and an anthropomorphic thorax phantom) were used to generate projection data. The simulation parameters are listed in Table 2. Quantum noise corresponding to 4.0×10⁵ photons per detector pixel was added to the projection data. In this work, no inhomogeneous bow-tie filtering and scatter were taken into consideration.

Simulations were conducted on a GPU cluster with NVIDIA Tesla C1060 CPUs, which consists of 30 multiprocessors (each with eight SIMD processing cores) and 4 GB of memory.

TABLE 2

Parameters used in the simulations.

| Parameter name | Value |
| --- | --- |
| Source-to-detector distance (mm) | 1085.6 |
| Source-to-object distance (mm) | 595.0 |
| Number of detector bins | 736 |
| Detector size at iso-center (mm²) | 0.60 × 0.60 |
| Total photon number per detector bin | 4.0 × 10⁵ |
| Number of energy bins | 280 |
| Energy bin size | 0.5 keV |
| Pixel size of the phantoms (mm²) | 0.20 × 0.20 |
| Pixel size of the reconstructed images (mm²) | 0.40 × 0.40 |
| Number of projections | 2304 |

In simulations, there were two errors that cause the computed voxel value $t_v$ to deviate from the theoretical value $t_v^0$, i.e., the error due to BH effect ($\eta_v^b$) and the error due to noise ($\eta_v^n$).

$$t_v = t_v^0 + \eta_v^b + \eta_v^n. \quad (18)$$

The BH effect results in visible artifacts (e.g., cupping and streaking) and invisible voxel accuracy issue. In this work, the invisible voxel accuracy issue was quantified by only measuring the mean errors on uniform regions of a material. The noise term $\eta_v^n$ in the above equation can originate from different sources, such as quantum noise, electronic noise, under sampling, and discretization model (e.g., target volume voxelization or x-ray line integral, etc.). Here it is assumed that $\eta_v^n$ was the compound result of these noise sources, followed a zero-mean Gaussian distribution.

In a uniform region of a single material, the standard deviation of $n_v^b$ and the mean value of $n_v^n$ should be both approximately zero values. Thus, normalized mean error (NME) and normalized standard deviation (NStd) were to quantify the BH effect and noise level, respectively. The mathematical forms for NME and NStd were $$NME = \frac{1}{N}\sum_{v=1}^{N}\left(\frac{t_v - t_v^0}{t_v^0}\right) \approx \frac{1}{N}\sum_{v=1}^{N}\frac{\eta_v^b}{t_v^0}, \quad (19)$$

and $$NStd = \sqrt{\frac{1}{N}\sum_{v=1}^{N}\left(\frac{t_v - \bar{t}}{t_v^0}\right)^2} \approx \sqrt{\frac{1}{N}\sum_{v=1}^{N}\left(\frac{\eta_v^n}{t_v^0}\right)^2}, \quad (20)$$

where N is the total number of the voxels in the measured ROI, and $\bar{t}$ is the ROI mean value. Normalized root mean square error (NRMSE) may be utilized to quantify the differences between the reconstructed image and phantom image. However, it is not difficult to derive that $$NRMSE = \sqrt{\frac{1}{N}\sum_{v=1}^{N}\left(\frac{t_v - t_v^0}{t_v^0}\right)^2} \approx \sqrt{NME^2 + NStd^2}. \quad (21)$$

If BH effect is eliminated after several iterations, NME can approach zero, and then NStd can be used to approximate NRMSE. For simplicity, BH index (BIdx) and noise index (NIdx) may be used to denote as percentage of NME and percentage of NStd, respectively:

$$BIdx = NME \times 100, \text{ and} \quad 7$$

$$NIdx = NStd \times 100. \quad 8$$

Figure 2:
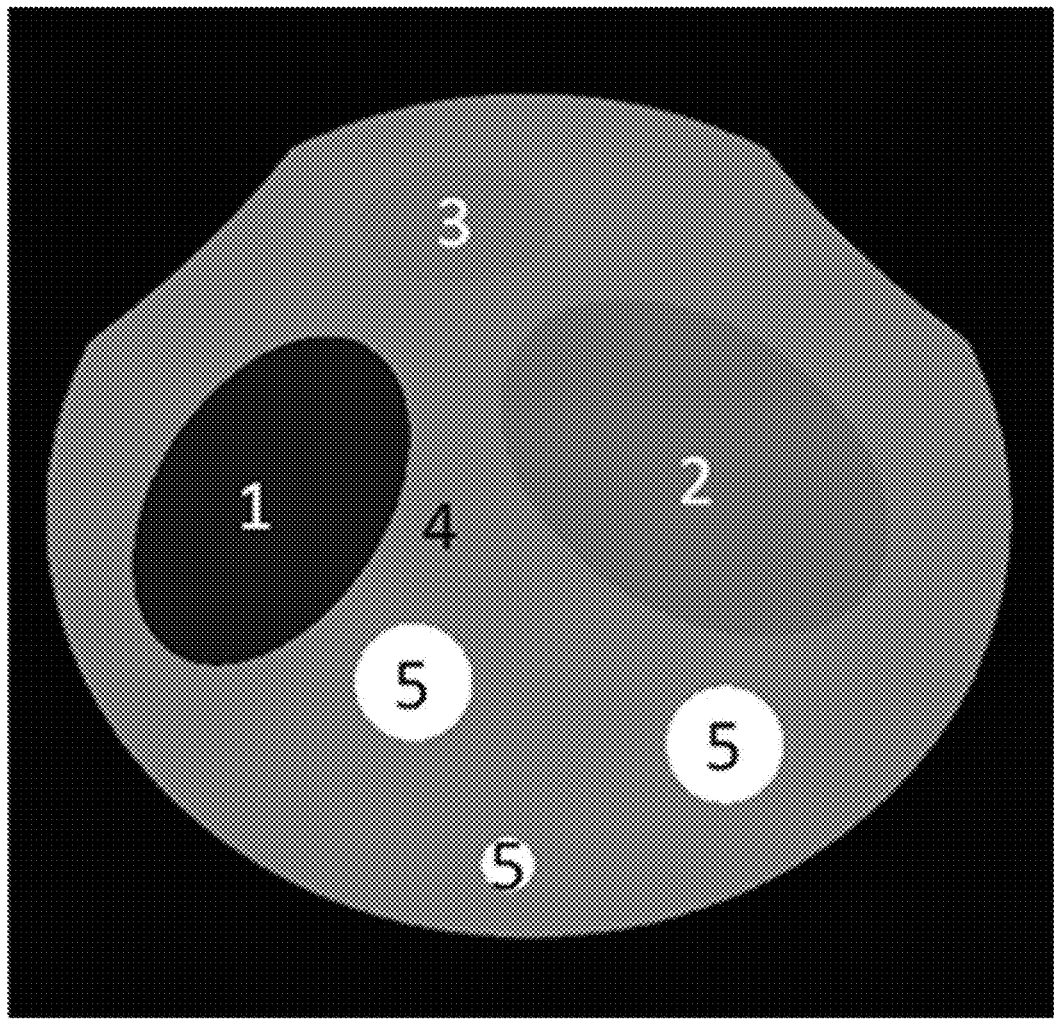
FIG. 2 is an image of an oval phantom consisting of the lung, fat, breast, soft tissue, and bone (1200 mg/cc) used for validation.

FIG. 2 is an image of an oval phantom consisting of the lung, fat, breast, soft tissue, and bone (1200 mg/cc) used for validation. This phantom is a simplified and idealized model to quantitatively assess the performance of the reconstruction algorithms. This phantom was scaled to four different sizes, i.e., 16, 24, 32, and 40 cm in diameter.

Six simulation tests were conducted on this phantom, i.e., an algorithm test, a convergence test, a phantom size test, a spectrum type test, and a spectrum mismatch test. In the first simulation test, reconstruction results of the 32 cm oval phantom were compared between different algorithms, including FBP with a mono-energetic spectrum projection dataset (70 keV), and water-corrected FBP and piFBP-type methods (piFBP-W, piFBP-WS, and piFBP) with a poly-energetic spectrum projection dataset (80 kVp). In the second simulation test, the convergence properties of the piFBP-type methods (piFBP-W, piFBP-WS, and piFBP) were investigated on the same 32 cm oval phantom. In the third simulation test, the oval phantom was scaled to four sizes, i.e., 16, 24, 32, and 40 cm diameter, to examine the reconstruction stability associated with the phantom size. In the fourth simulation, the spectrum (80, 100, 120, and 140 kVp) was varied to test the reconstruction stability associated with the x-ray spectrum. A spectrum mismatch test was conducted to investigate the influence of a possible difference between the actual and the assumed spectra. By adjusting the inherent aluminum filtration of the x-ray tube, the correct spectrum of 80 kVp can be softened or hardened to yield nineteen mismatch spectra with the normalized root mean square differences (NRMSDs) ranging from −9% to 9%, where negative NRMSDs indicate softened spectra and positive NRMSDs indicate hardened spectra. Finally, a base material transition test was conducted to investigate the benefit of more base materials. The projection dataset acquired with a 32 cm oval phantom and a spectrum of 80 kVp was reconstructed by increasing the number of the base materials. The base material groups used in this test are listed in Table 3. The parameters used in the six simulation tests are summarized in detail in Table 4.

Figure 3:
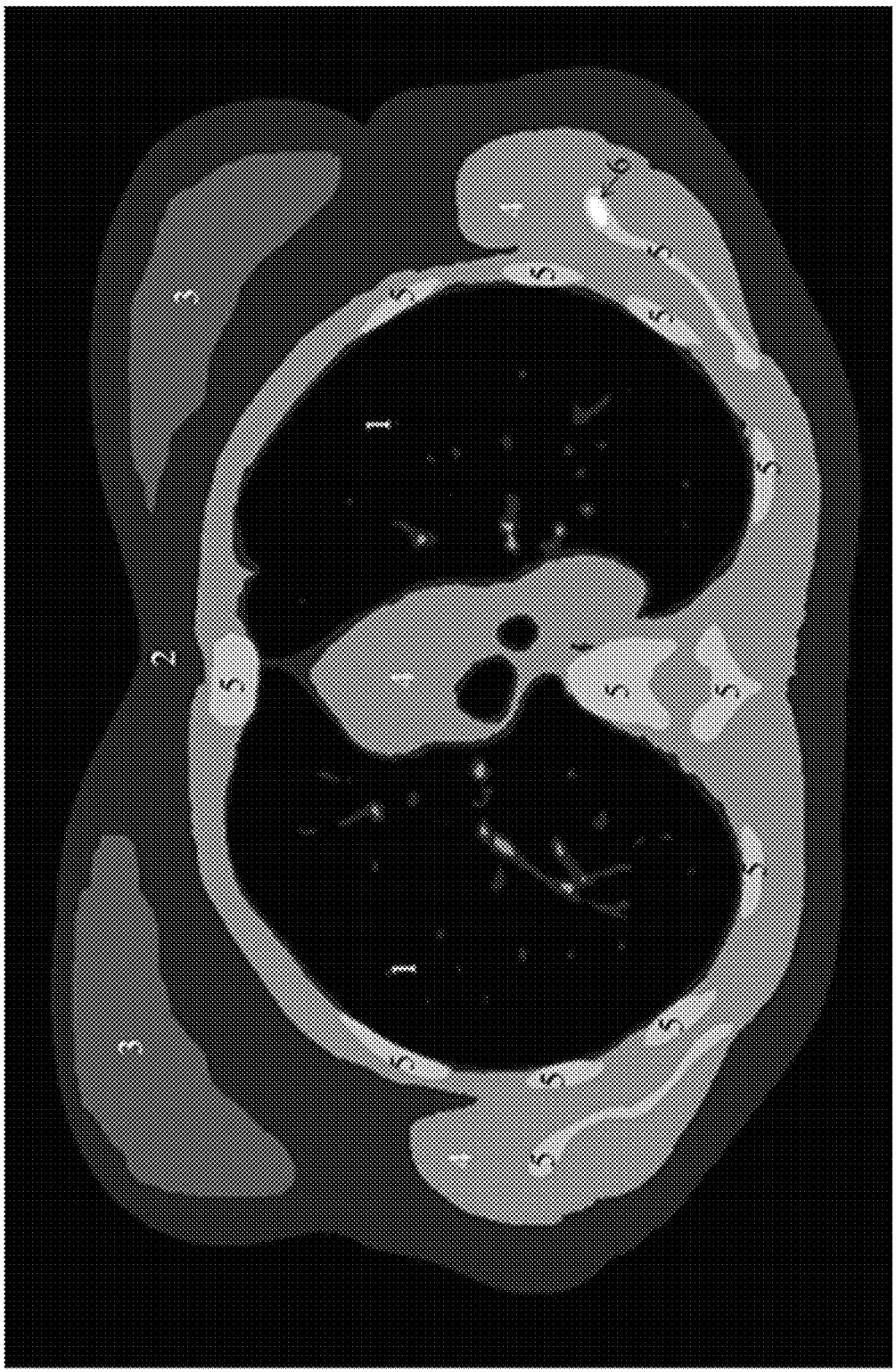
FIG. 3 is an image depicting a definition of the oval phantom with (1) lung, (2) fat, (3) breast, (4) soft tissue, and (5) bone (1200 mg/cc)

FIG. 3 is an image depicting a definition of the oval phantom with (1) lung, (2) fat, (3) breast, (4) soft tissue, and (5) bone (1200 mg/cc). This phantom was scaled to four different sizes, i.e., 16, 24, 32, and 40 cm in diameter.

TABLE 3

Base material groups used in the base material transition test.

|  | Group 1 | Group 2 | Group 3 | Group 4 | Group 5 |
|---|---|---|---|---|---|
| Base material | Water | Soft tissue<br>Bone | Breast<br>Soft tissue<br>Bone | Fat<br>Breast<br>Soft tissue<br>Bone | Lung<br>Fat<br>Breast<br>Soft tissue<br>Bone |

TABLE 4

Parameter summary of simulation tests for the cylindrical phantom.

| Simulation tests | Varying parameters | Fixed parameters |
|---|---|---|
| Algorithm test | Algorithm:<br>FBP (70 keV)<br>FBP (80 kVp)<br>piFBP-W (80 kVp)<br>piFBP-WS (80 kVp)<br>piFBP (80 kVp) | Phantom size: 32 cm<br>Iteration: 4 |
| Convergence test | Algorithm:<br>piFBP-W<br>piFBP-WS<br>piFBP<br>Iteration number:<br>0, 1, 2, 3, 4, 10 | Phantom size: 32 cm<br>Spectrum: 80 kVp |
| Phantom size test | Algorithm:<br>FBP, piFBP<br>Phantom size:<br>16, 24, 32, and 40 cm | Spectrum: 80 kVp<br>Iteration: 4 |
| Spectral type test | Algorithm:<br>FBP, piFBP<br>Spectrum:<br>80, 100, 120, 140 kVp | Phantom size: 32 cm<br>Iteration: 4 |
| Spectral mismatch test | Mismatch spectrum:<br>NRMSD = −9%, . . . , 9% | Algorithm: piFBP<br>Phantom size: 32 cm<br>Spectrum: 80 kVp<br>Iteration: 4 |
| Base material transition test | Base material groups:<br>Listed in Table 3 | Algorithm: piFBP<br>Phantom size: 32 cm<br>Spectrum: 80 kVp<br>Iteration: 4 |

In contrast to the previous phantom, real CT data from the database of The Cancer Imaging Archive (TCIA, http://www.cancerimagingarchive.net/) was used to create a more complex and realistic anthropomorphic thorax phantom, which is shown in the image of FIG. 3. FIG. 3 depicts the definition of the anthropomorphic thorax phantom with (1) lung, (2) fat, (3) breast, (4) soft tissue, (5) bone (1600 mg/cc), and (6) metal implant (Titanium). This phantom was composed of various materials, including five main body tissues (i.e., lung, fat, breast, soft tissue, and bone) and one metal implant (i.e., Titanium). With this phantom, the reconstruction performance under an extreme condition, i.e., when a metal implant exists in the patient body, were investigated by comparing piFBP (80 kVp) with FBP (70 keV) and FBP (80 kVp).

Figure 4A:
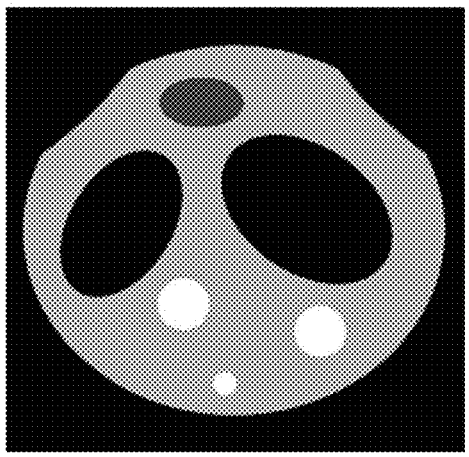
FIGS. 4A-4F show reconstructed images of an oval phantom by different algorithms with the corresponding quantitative results.
Figure 4B:
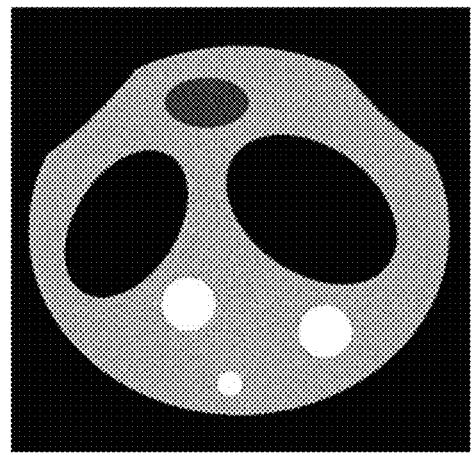
Figure 4C:
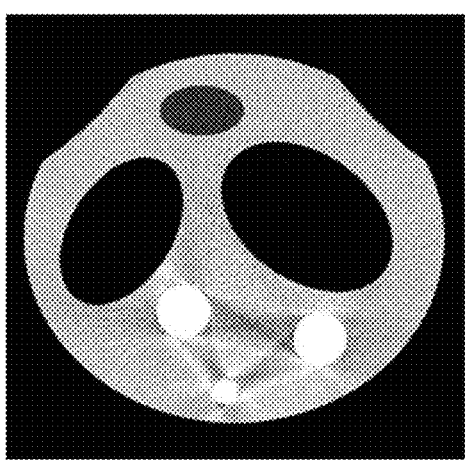
Figure 4D:
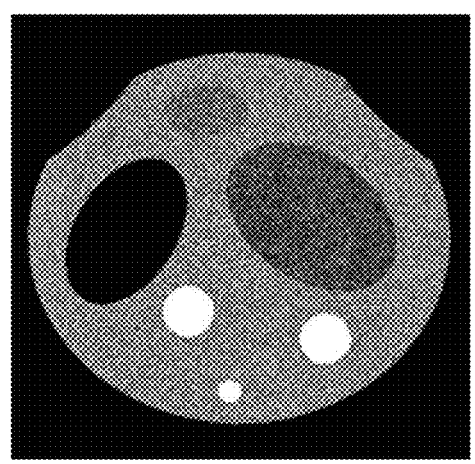
Figure 4E:
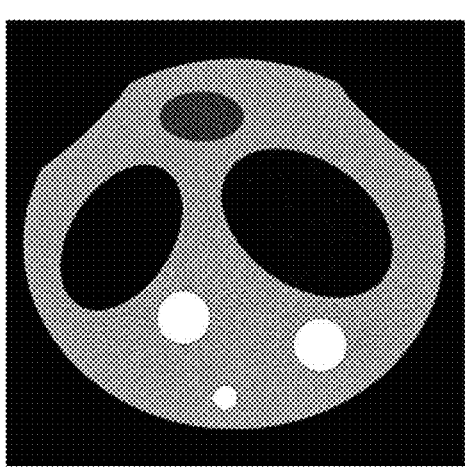
Figure 4F:
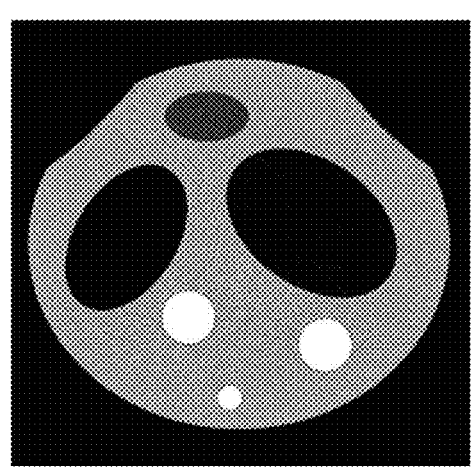

FIGS. 4A-4F show the reconstructed images of the oval phantom by different algorithms with the corresponding quantitative results listed in Table 4. Particularly, FIG. 4A shows the oval phantom with real attenuation coefficients (70 keV) of various body tissues. FIG. 4B was reconstructed by FBP with mono-energetic 70 keV spectrum projection dataset. The rest of the images were reconstructed from the same poly-energetic 80 kVp spectrum projection dataset but different algorithms, i.e., FIG. 4C is water-corrected FBP, FIG. 4D is piFBP-W, FIG. 4E is piFBP-WS, and FIG. 4F is piFBP. The window level=40 HU, and the window width=100 HU.

For reference purposes, the oval phantom with real attenuation coefficients (70 keV) of body tissues is shown in FIG. 4A, and the images reconstructed by FBP (70 keV) is shown in FIG. 4B. Because of the use of a mono-energetic spectrum, there were no visible BH artifacts in the reconstructed image, and the BIdx values of all materials were zeros. The NIdx values reflected the normalized noise levels, which were the lower limits that can be achieved by the poly-energetic reconstruction algorithms. It is noted that the NIdx of the lung was larger than those of the other body tissues. That is because lung has smaller attenuation coefficient, which magnified its NIdx value through the normalization process in Equation 20. The BIdx and NIdx of FIG. 4B were provided as benchmark values.

FIG. 4C shows the image reconstructed by water-corrected FBP with 80 kVp poly-energetic spectrum. Because of the BH effect, the dark streak artifacts between the bones severely degraded the image quality and the BIdx values of all materials spread within a large range of [−1.8, 10.4], which undermined quantitative evaluation. Based on the attenuation coefficient, the estimated bone density was 1464 mg/cc, which significantly deviated from the expected value of 1200 mg/cc. The NIdx values of FBP (80 kVp) were slightly larger than the NIdx benchmark values. This was due to the fact that the 80 kVp spectrum had more low energy photons than the 70 keV spectrum, so more photons were attenuated and less photons could reach the detector, which raised the quantum noise in the measurements, and finally raised the noise level in the reconstructed images.

The image reconstructed by the piFBP-W algorithm after four iterations is shown in FIG. 4D. The strong noise severely deteriorated the image quality, and the NIdx values in Table 4 increased multiple times for all materials. However, the iterations did help reduce the streak artifacts, making the streak artifacts almost invisible. This improvement was also reflected by the reduced spread range of BIdx, i.e., [−0.9, 0.7].

With the smoothing filter, the images reconstructed by piFBP-WS and piFBP with four iterations are shown in FIGS. 4E and 4F. Neither of these had visible beam-artifacts or severe noise. In addition, the two images were almost visually identical to FIG. 4B. The quantitative results showed that both BIdx and NIdx were close to their corresponding benchmark values. With Equation 4, the bone density was estimated to be 1201 mg/cc, which was very close to the expected value of 1200 mg/cc.

TABLE 5

Quantitative results of the oval phantom in terms of the beam hardening index (BIdx) and noise index (NIdx) for different materials and reconstruction algorithms.

| BIdx/NIdx | Lung | Fat | Breast tissue | Soft tissue | Bone |
|---|---|---|---|---|---|
| FBP (70 keV) | 0.0/1.1 | 0.0/0.3 | 0.0/0.3 | 0.0/0.4 | 0.0/0.2 |
| FBP (80 kVp) | 1.5/1.4 | −1.8/0.4 | −1.0/0.3 | 0.1/0.6 | 10.4/0.4 |
| piFBP-W | −0.8/5.5 | −0.8/1.4 | −0.9/1.1 | −0.4/1.4 | 0.7/0.8 |
| piFBP-WS | 0.0/1.7 | −0.1/0.5 | −0.1/0.4 | 0.0/0.5 | 0.1/0.3 |
| piFBP | 0.0/1.7 | −0.1/0.5 | −0.1/0.4 | 0.0/0.5 | 0.1/0.3 |

Figure 5A:
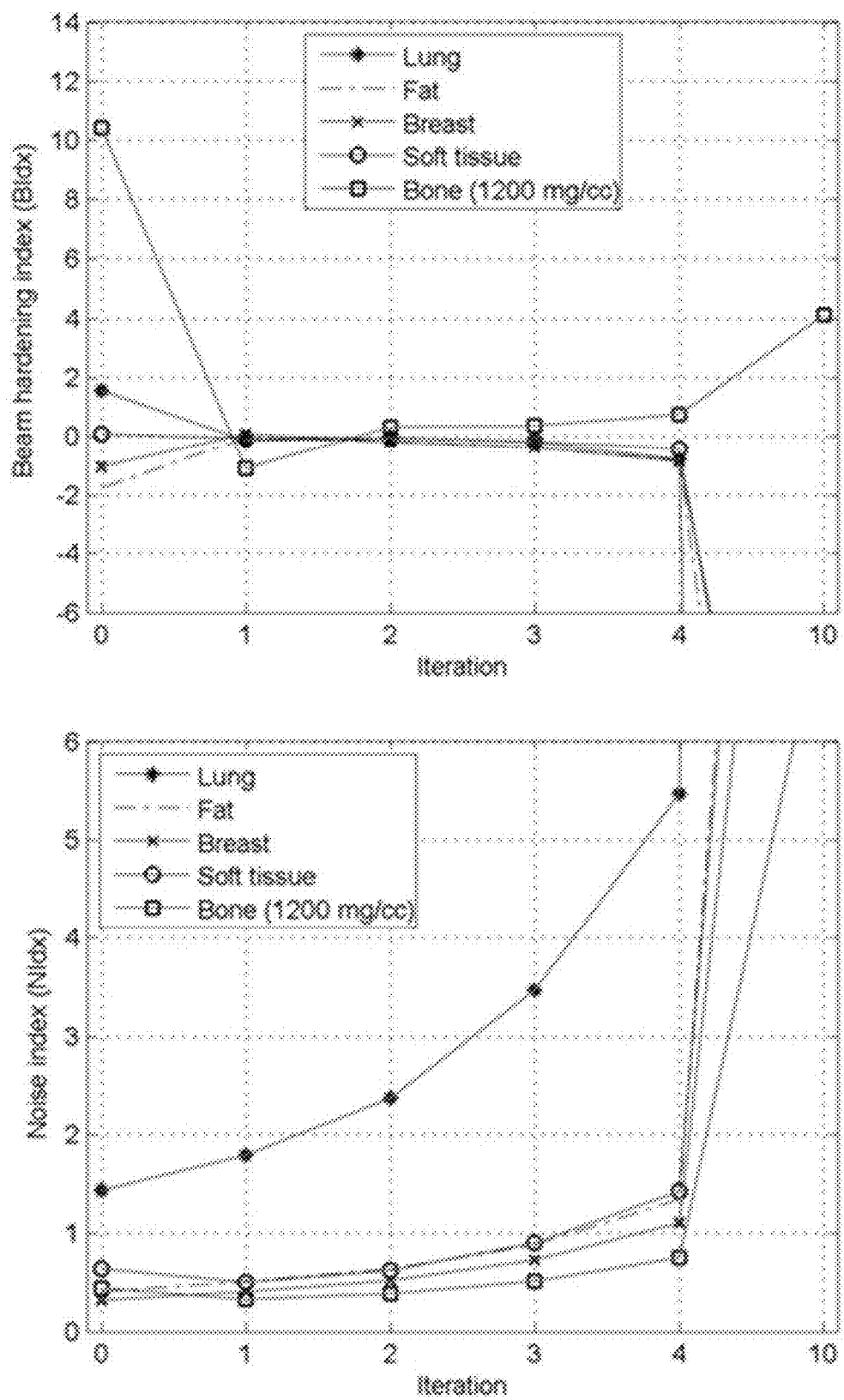
FIG. 5A illustrates graphs BIdx and NIdx of algorithm piFBP-W.
Figure 5C:
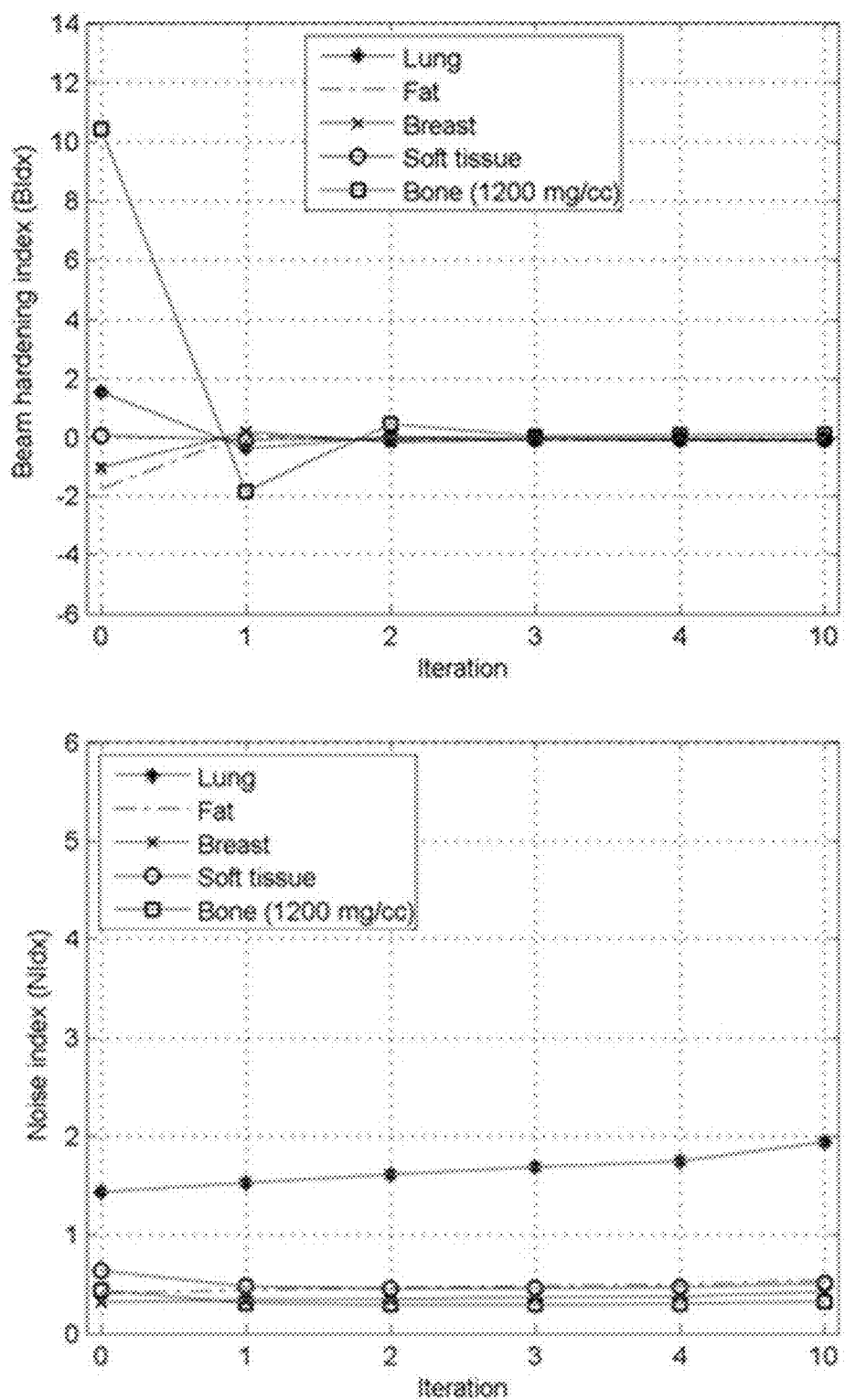
FIG. 5C illustrates graphs of BIdx and NIdx of algorithm piFBP.
Figure 6A:
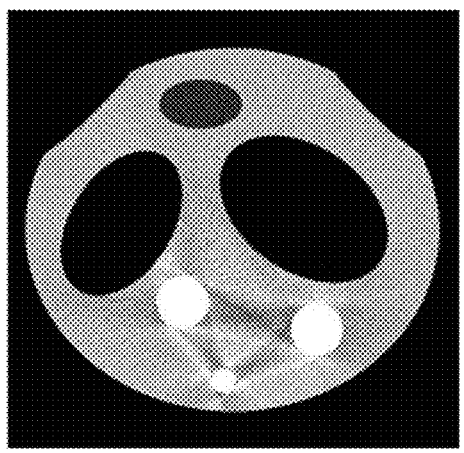
FIGS. 6A-6F depicts images reconstructed by piFBP at the 0th, 1st, 2nd, 3rd, 4th, and 10th iterations, respectively.
Figure 6B:
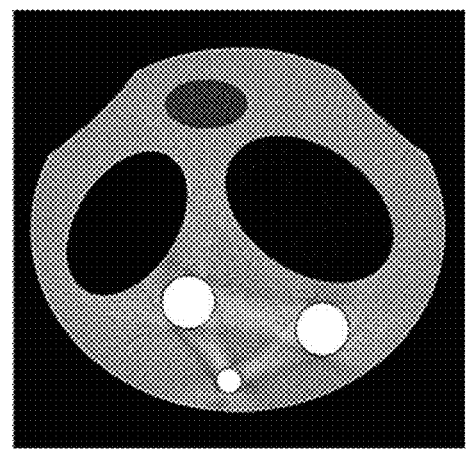
Figure 6C:
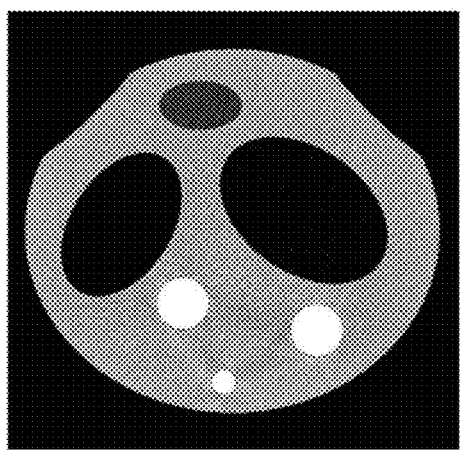
Figure 6D:
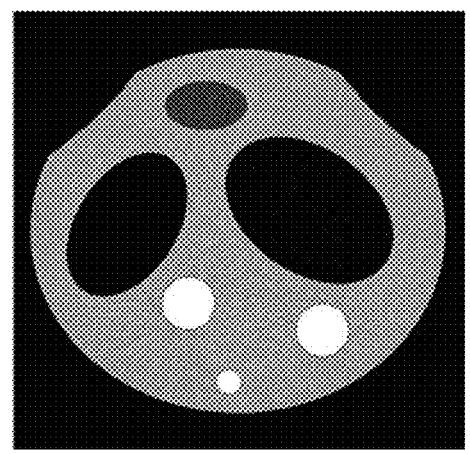
Figure 6E:
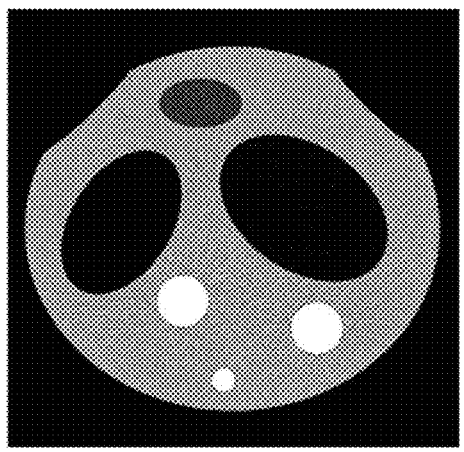
Figure 6F:
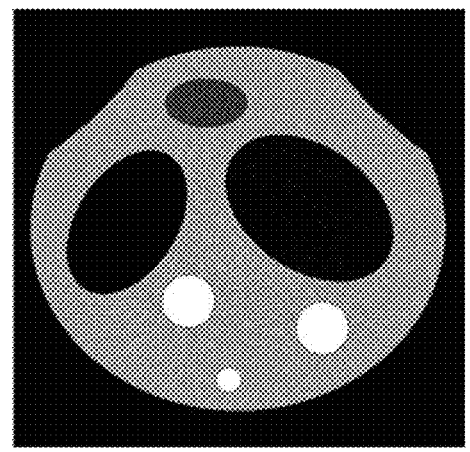

To further explore the convergence properties of the algorithms piFBP-W, piFBP-WS, and piFBP, the iteration trends of the BIdx and NIdx of various materials are plotted in FIGS. 5A-5C. More particularly, FIG. 5A illustrates graphs of BIdx and NIdx of algorithm piFBP-W, FIG. 5B illustrates graphs of BIdx and NIdx of algorithm piFBP-WS, and FIG. 5C illustrates graphs of BIdx and NIdx of algorithm piFBP.

These graphs show iteration trends of BIdx and NIdx of various materials in the oval phantom for algorithms piFBP-W, piFBP-WS, piFBP.

For algorithm piFBP-W, BIdx curves in FIG. 5A are significantly reduced in the first several iterations. However, due to the increasing noise, both BIdx and NIdx diverge after four iterations.

The BIdx curves of algorithms piFBP-WS and piFBP both converged to zero after three iterations. As water correction could reduce the nonlinearity of the projection data, so piFBP-WS converged slightly faster than piFBP. This improvement was reflected by the fact that the BIdx curve of bone in FIG. 5B had smaller oscillation magnitudes than that in FIG. 5C. As for the NIdx, there were no obvious differences between the curves of piFBP-WS and piFBP, and all the NIdx curves approximately maintained their original noise levels. The NIdx curves of lung of the two algorithms increased slightly, which was because the small attenuation coefficient of lung made its normalized NIdx sensitive to the noise. To help readers better appreciate the BH correction process, the images reconstructed by piFBP at the 0th, 1st, 2nd, 3rd, 4th, and 10th iterations are presented in FIGS. 6A-6F, which depicts images reconstructed by piFBP at the 0th, 1st, 2nd, 3rd, 4th, and 10th iterations, respectively. Window level was equal to 40 HU, and window width was equal to 100 HU.

Compared with piFBP, piFBP-WS had smaller oscillation magnitudes of BIdx curves but longer computational time (Table 6), which was caused by the time consuming water correction process in each iteration. Given the similar reconstruction results, piFBP is certainly a better choice.

TABLE 6

The comparison of computational speeds between piFBP-WS and piFBP.

| | Iterations | Time/Iteration | Total Time |
|---|---|---|---|
| piFBP-WS | 4 | 21 sec | 84 sec |
| piFBP | 4 | 7 sec | 28 sec |

Figure 7:
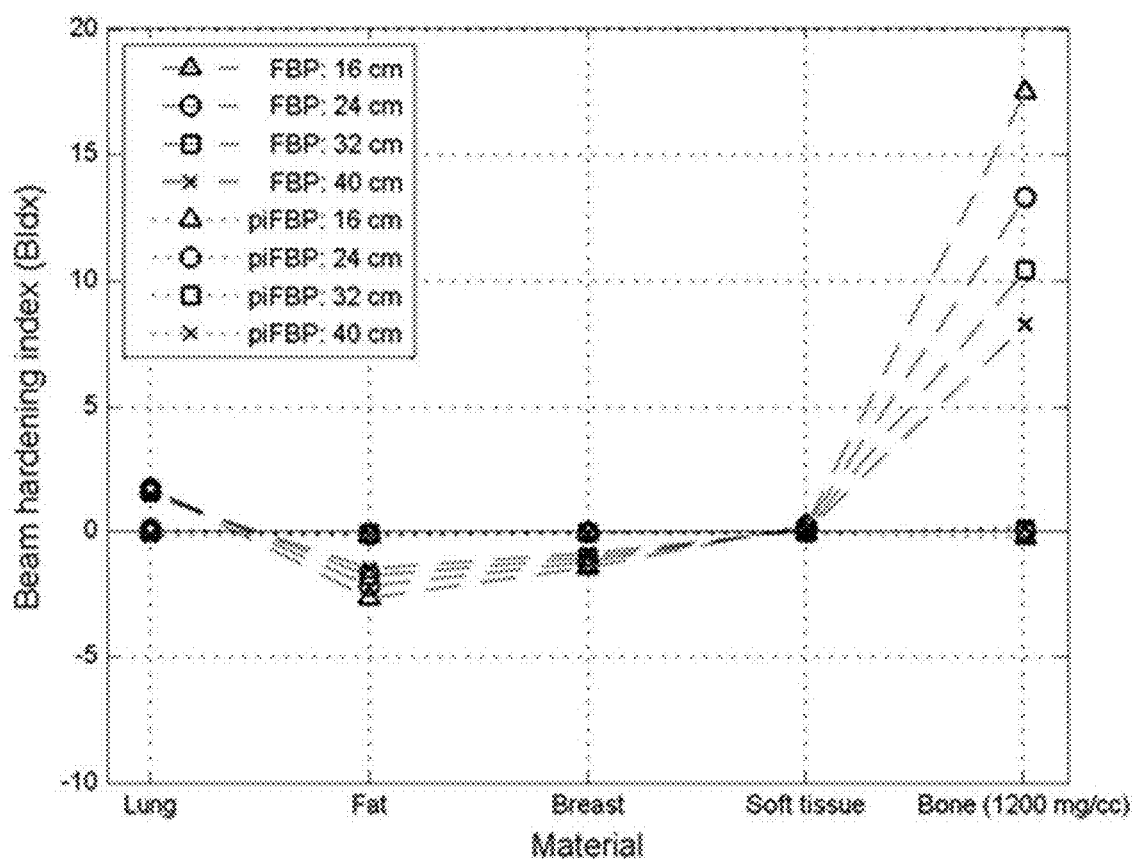
FIG. 7 illustrates a graph showing phantom size test results.

The effect of phantom size to different body tissues is illustrated in FIG. 7, which illustrates a graph showing phantom size test results. By varying phantom size (triangle: 16 cm; circle: 23 cm; square: 30 cm; cross: 37 cm), BIdx's are plotted for different materials and algorithms (dashed line: FBP; dotted line: piFBP). All simulations in this test used the 80 kVp spectrum. For FBP (dashed lines, 80 kVp), soft tissue maintained low BIdx values because its attenuation property was similar to that of water. Other materials were either underestimated or overestimated due to the BH effect. Among those materials, bone values not only significantly deviated from the theoretical values, but showed a large variation across different phantom sizes. For piFBP (dotted lines, 80 kVp), negligible BIdx values for any body tissue and phantom size showed that piFBP possesses stable reconstruction ability across phantom size.

Figure 8:
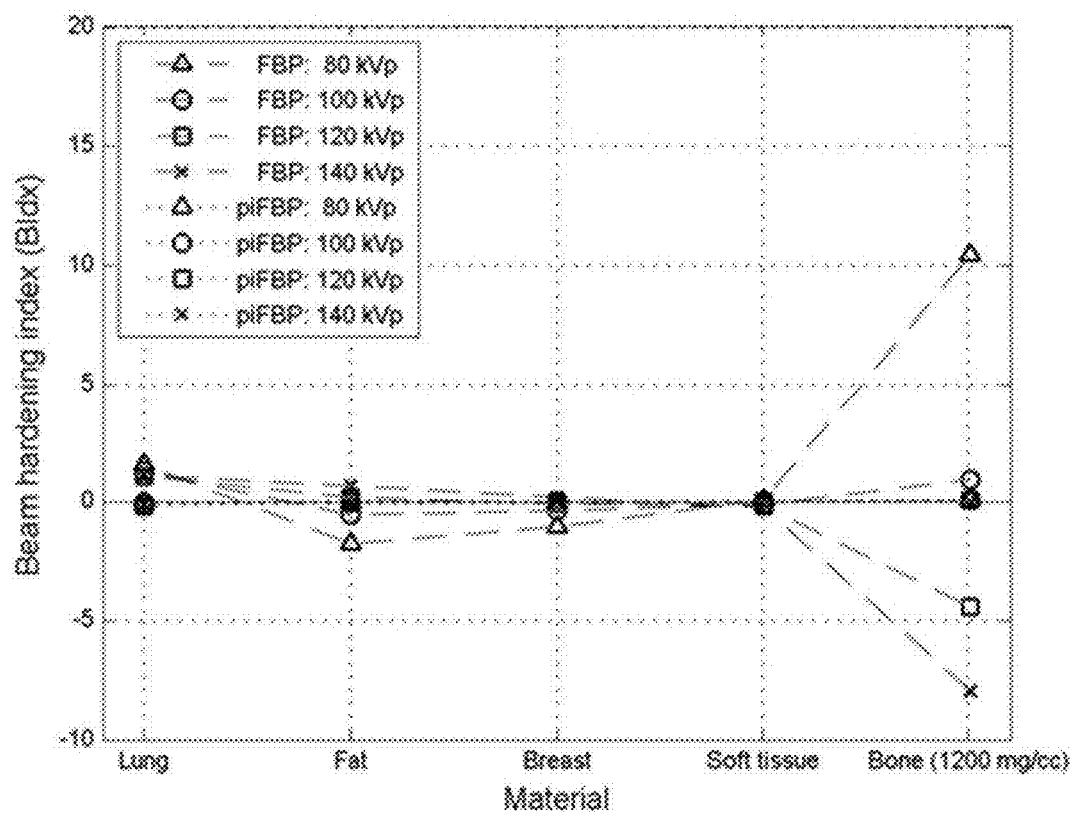
FIG. 8 illustrates a graph showing spectral test results.

The effect of the spectrum choice to different body tissues was reflected in FIG. 8, which illustrates a graph showing spectral test results. By varying x-ray spectrum (triangle: 80 kVp; circle: 100 kVp; square: 120 kVp; cross: 140 kVp), BIdx's are plotted for different materials and algorithms (dashed line: FBP; dotted line: piFBP). All simulations in this test used the 32 cm diameter phantom. All simulations in this test used the same 32 cm oval phantom. For FBP (dashed lines), soft tissue still maintained low BIdx values like the results in FIG. 7, but the other body tissues had relatively larger magnitudes of variation. In contrast, PE-IFPB (dotted lines) showed negligible BIdx values for different materials and spectra, which proved its stable reconstruction ability associated with the spectrum.

Figure 9:
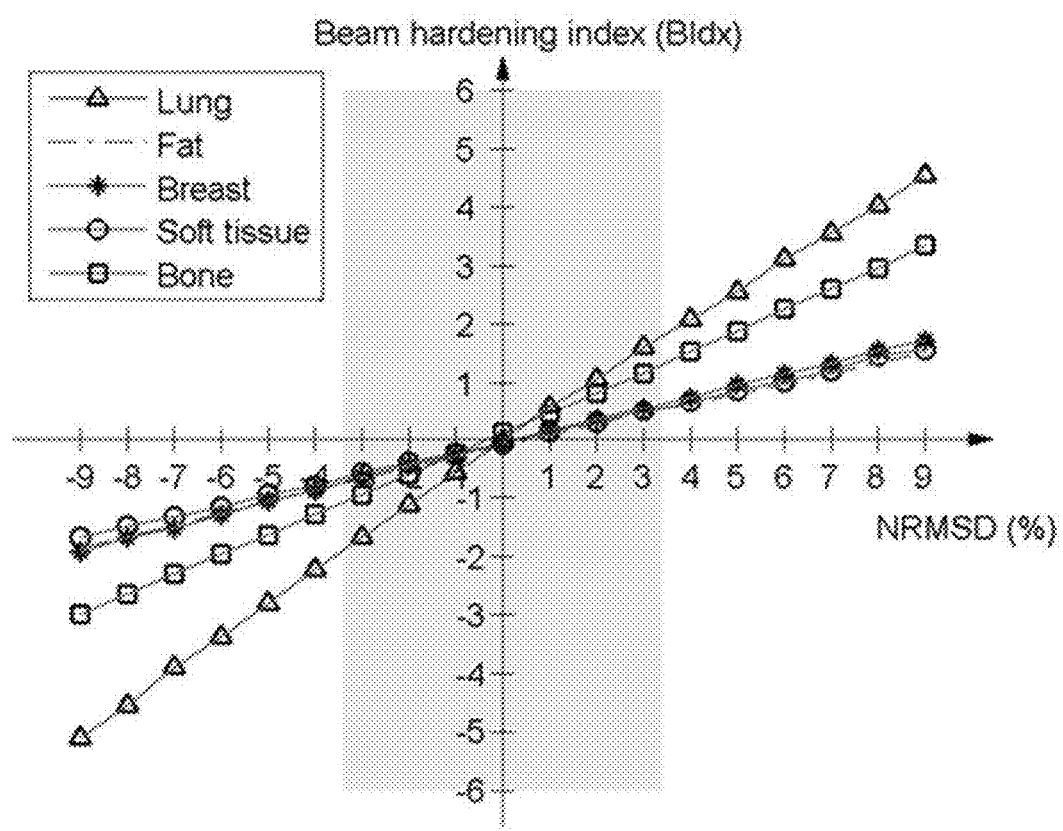
FIG. 9 illustrates a plot showing spectrum mismatch results.

The results of the spectrum mismatch test are shown in FIG. 9, which illustrates a plot showing spectrum mismatch results. BIdx's of different body tissues were derived based on different mismatch spectra (80 kVp), the NRMSDs of which ranged from −9% to 9%. The projection data were simulated by using the 32 cm diameter phantom. When the mismatch spectra were harder than the correct spectrum (80 kVp), the BIdx's of all tissues increased to compensate the decreased photon numbers in the low energy range. The reverse was the case for softer spectra. For the spectra with largest NRMSDs of −9% and 9%, the BIdx range increased from [−0.1, 0.1] to [−5.1, 4.5]. Based on an implemented spectrum measurement technique, an experimental accuracy of ±3.4% is readily achievable for the 80 kVp spectrum. Therefore, the BIdx range could be reduced down to [−1.8, 1.6], which was smaller than that of FBP with the correct spectrum (i.e., [−1.8, 10.4]). If water calibration is available, the BIdx range could be further reduced by subtracting the offset value of water. This test suggested that piFBP could moderately tolerate the mismatch spectra.

Figure 10:
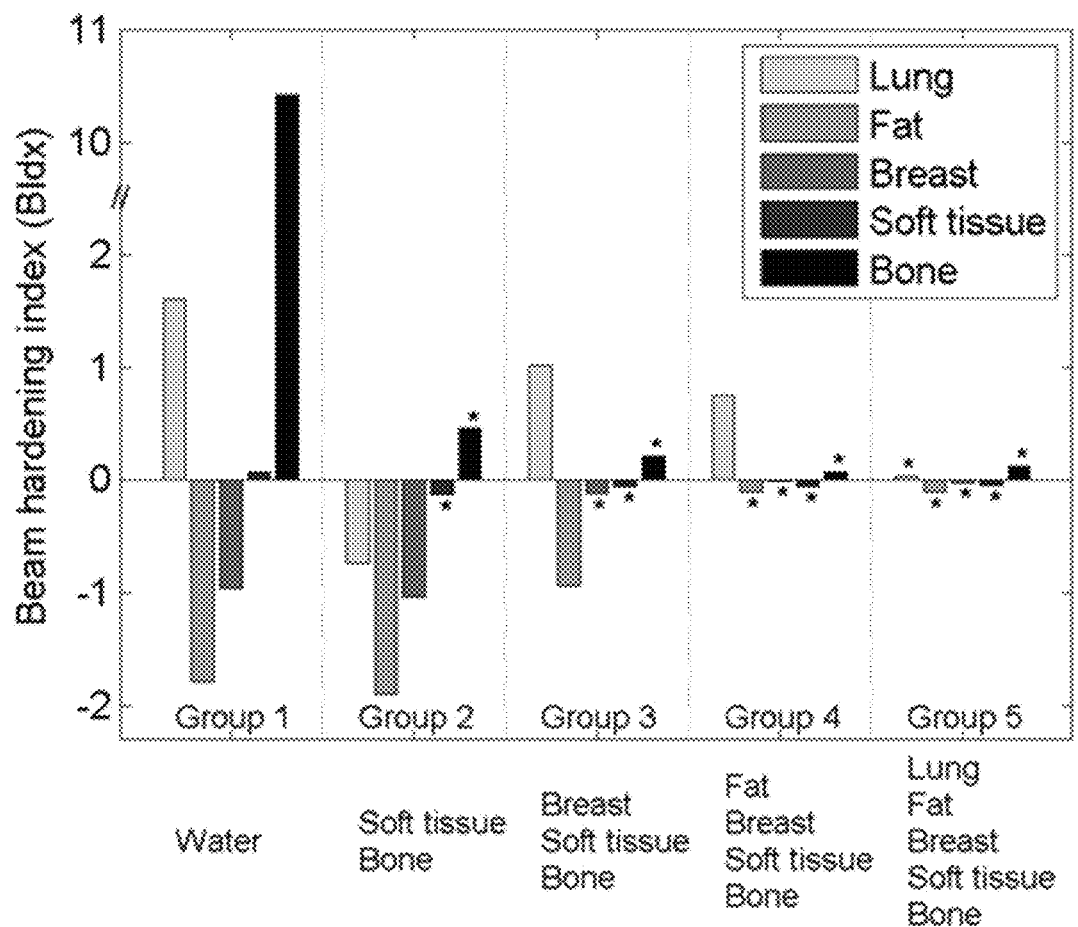
FIG. 10 illustrates a graph showing the simulation results of the base material transition test.

The results of the base material transition test are plotted in FIG. 10, which illustrates a graph showing the simulation results of the base material transition test. In FIG. 10, the columns without stars indicate that the corresponding materials are not base materials. The columns with stars indicate that the corresponding materials are base materials. The columns without stars indicate that the corresponding materials are not base materials. The columns with stars indicate that the corresponding materials are base materials. Referring to the indices of Table 3, when water was used as the base material (group 1), only soft tissue had negligible BIdx. Adding bone as a base material (group 2) greatly reduced the bone's BIdx. Adding breast as a base material (group 3) further reduced the BIdx of breast to a negligible level. Note that fat also showed a small improvement as in this case fat was interpreted as low density breast tissue instead of low density soft tissue as the attenuation property of fat is closer to that of the breast. With the addition of fat (group 4), the BIdx associated with fat was further reduced. Finally, adding lung as a base material (group 5) reduced lung's BIdx to a negligible level as well.

Figure 11:
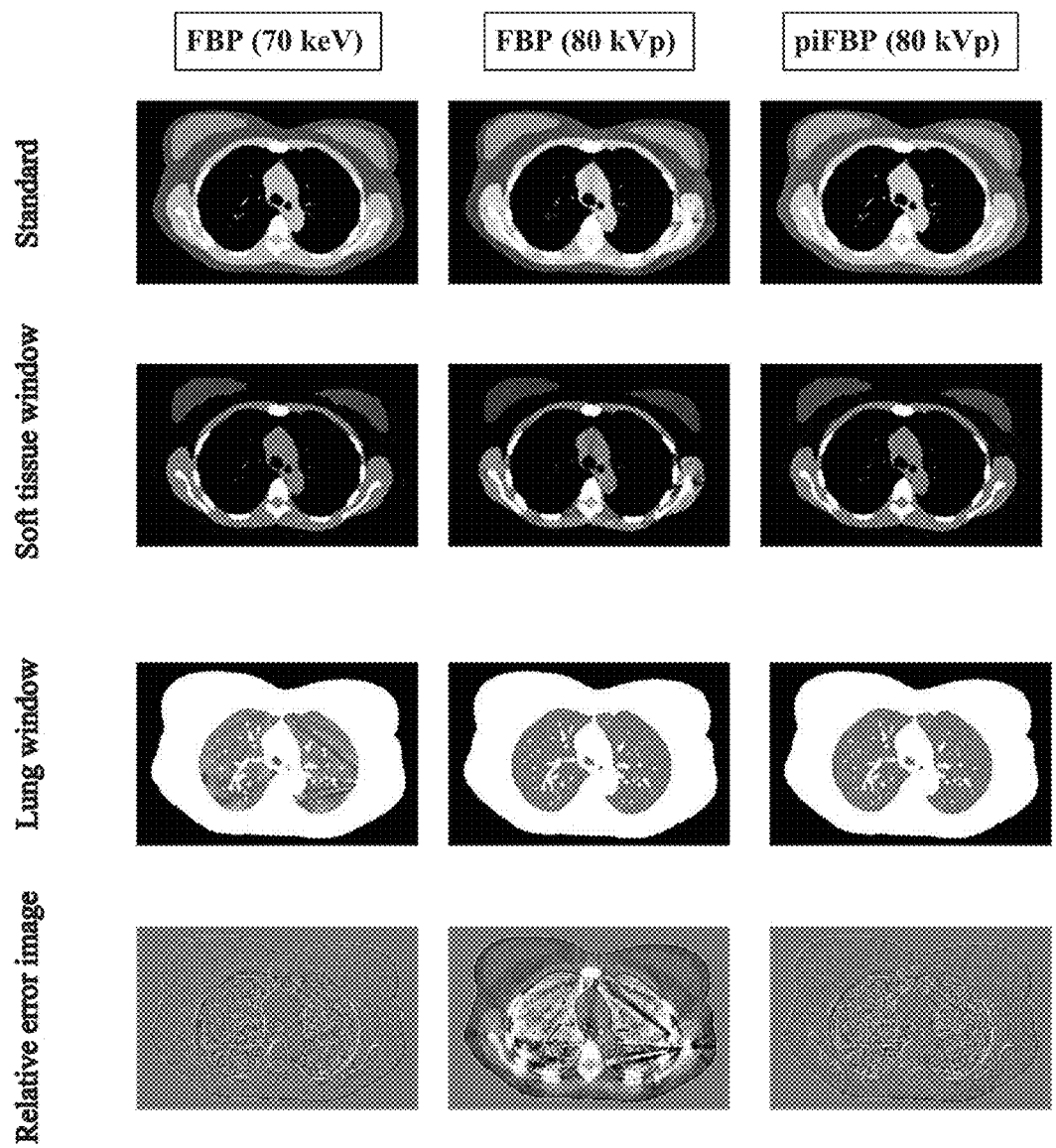
FIG. 11 illustrates images of reconstruction results of the anthropomorphic thorax phantom.

The reconstruction results of the anthropomorphic thorax phantom are presented in FIG. 11, which illustrates images of reconstruction results of the anthropomorphic thorax phantom. The images from the first column to the third column were reconstructed by the FBP with mono-energetic spectrum (70 keV), FBP with poly-energetic spectrum (80 kVp), and piFBP with poly-energetic spectrum (80 kVp), respectively. The images from the first row to the third row are shown in different windows, i.e., fat window (−20/300), soft tissue window (60/240), and lung window (−800/200). The last row shows the percent relative error images with window level 0/20. Table 7 shows quantitative results of the anthropomorphic thorax phantom in terms of the beam hardening index (BIdx) and the noise index (NIdx) for different materials and reconstruction algorithms. The three columns from left to right are the images reconstructed by algorithms FBP (70 keV), FBP (80 kVp), and piFBP (80 kVp), respectively. To facilitate visually comparison, from the first row to the third row, the images were adjusted to different windows, i.e., standard window (−20/300), soft tissue window (60/240), and lung window (−800/200). The percent relative error images with window level 0%/20% are shown in the last row for the attenuation value accuracy comparison.

The images in the first column of FIG. 11 were reconstructed by FBP (70 keV). Because of using a mono-energetic spectrum, no BH artifacts or metal artifacts were noticeable. The actual phantom data was used as benchmark images for the test comparisons.

The images reconstructed by FBP (80 kVp) are shown in the second column (see FIG. 11). As compared with the images reconstructed by FBP (70 keV) in the first column, the BH artifacts due to the metal implant and the bones severely deteriorated the image quality. For example, the metal implant on the right clavicle resulted in strong dark streaks on various body tissues, such as fat (standard window), soft tissue (soft tissue window), and lung (lung window). In addition, the bones also created strong artifacts. For example, in the soft tissue window, the streaks between sternum and vertebral column created false appearance on the heart, which obscured the real anatomical structures, and complicated the interpretation process. In addition to the visible artifacts, the invisible BH effect, i.e., voxel accuracy, could be visually assessed by the relative error image. Similar with the results revealed in the last subsection, fat and breast tended to be underestimated, but lung and bones tended to be overestimated.

The images in the last column were reconstructed by piFBP (80 kVp). In comparison with FBP (80 kVp), the streaks caused by the bones and the metal implant disappeared, and the image appearance was almost the same with the images reconstructed by FBP (70 keV). The relative error image in the last row was almost uniformly zero values, which indicated high reconstruction accuracy of the piFBP algorithm.

The quantitative results of the three reconstruction algorithms are listed in Table 7. Strong streak artifacts were avoided during the measurements. The first row is the results of FBP (70 keV). All the BIdx values were zeros due to mono-energetic spectrum, except the BIdx value of the metal implant, which was caused by photon starvation phenomenon. For the FBP (80 kVp), strong BH effect could be observed from the significantly deviated BIdx values. As the 80 kVp spectrum had more low energy photons, the photon starvation phenomenon was aggravated. The NIdx values slightly increased because of the spectral difference. For piFBP, the BIdx values of all materials were significantly reduced and close to these of FBP (70 keV). Though some of the NIdx values of piFBP increase slightly, all the NIdx values were approximately maintained at the same level with those of FBP (70 keV) and FBP (80 kVp).

TABLE 7

Quantitative results of the oval phantom in terms of the beam hardening index (BIdx) and noise index (NIdx) for different materials and reconstruction algorithms

| BIdx/NIdx | Lung | Fat | Breast Tissue | Soft Tissue | Bone (1600 mg/cc) | Metal (Ti) |
|---|---|---|---|---|---|---|
| FBP (70 keV) | 0.0/4.4 | 0.0/0.9 | 0.0/0.7 | 0.0/0.8 | 0.0/0.4 | −0.4/0.4 |
| FBP (80 kVp) | 1.8/5.7 | −2.9/1.1 | −1.1/0.9 | −1.4/1.2 | 15.9/0.6 | 23.3/0.6 |
| piFBP | 0.3/6.9 | −0.3/1.6 | −0.1/1.1 | −0.3/1.1 | −0.3/0.5 | 1.3/0.9 |

Disclosed herein are fast poly-energetic iterative FBP reconstruction algorithms (piFBP) to eliminate BH artifacts and endow CT with stable quantitative reconstruction ability. The performance of the algorithm was systematically explored by an oval phantom and an anthropomorphic thorax phantom.

Six simulation tests were conducted on the oval phantom, including an algorithm test, a convergence test, a phantom size test, a spectrum type test, and a spectrum mismatch test. The algorithm test showed that both piFBP-WS and piFBP reduced the BIdx's of various tissues from [−1.8, 10.4] for FBP to [−0.1, 0.1] and maintained the NIdx's almost unchanged, which indicates the proposed algorithms could effectively eliminate the BH effect and suppress the increasing noise. The convergence test showed that piFBP converged slightly slower than piFBP-WS, but required less computational time, so only piFBP algorithm was used for the following simulation tests and recommended for clinical practice. In the phantom size and spectrum tests, the variation range of the BIdx's was reduced from [−7.5, 17.5] for FBP to [−0.1, 0.1], which indicates that piFBP possessed stable reconstruction ability across all phantom sizes (16, 24, 32, 40 cm) and spectra (80, 100, 120, and 140 kVp). The spectrum mismatch test showed that piFBP could moderately tolerate the mismatch spectra, as the range of BIdx's of all materials only increased from [−0.1, 0.1] (derived with the correct spectrum) to [−1.8, 1.6] for the spectrum with the NRMSDs of +3.4% expected from experimental measurements. If water calibration information is available, the errors could be further reduced. Finally, the base material transition test indicated the importance of incorporating the correct attenuation information of the base materials in the scanned objects.

The reconstruction performance of piFBP was tested on a realistic anthropomorphic thorax phantom in the presence of a metal implant. The simulation results showed that the BH artifacts of the body tissues could be effectively eliminated and the metal artifacts significantly reduced with four iterations, as the variation range of the BIdx's was reduced from [−2.9, 15.9] for FBP to [−0.3, 0.3] for piFBP and the BIdx of the metal implant from 23.3 to 1.3. The BIdx residue of the metal implant was due to the photon starvation.

There are three important features that distinguish our poly-energetic reconstruction algorithms from the previous ones. First, most of the iterative-based base material approaches can only incorporate one or two materials into the reconstruction process. In contrast, the adaptive base material decomposition method introduced in this work can help incorporate diverse body tissues (such as lung, fat, breast, soft tissue, and bone) and also implant metals into the reconstruction process. The wide range of the base materials enables our reconstruction algorithm to significantly reduce the BH artifacts and to quantitatively reconstruct the images.

Second, IFBP was mainly used to solve the non-uniform attenuation compensation problem in SPECT. Simulations showed that the conventional IFBP diverge due to the influence of noise. To improve the convergence property, IFBP was reformed by adding a smoothing kernel (piFBP) to reduce noise but maintain BH correction signals. This proposed algorithm piFBP significantly improves the convergence stability and makes it possible for BH correction.

The third important feature is the fast reconstruction speed. Different from other poly-energetic iterative algorithms, which requires dozens or hundreds of iterations and long reconstruction time, our method can finish reconstruction with at most four iterations. If using high kVp spectra or bow-tie wedges to reduce the amount of low energy photons, the iteration number can be further reduced. The fast speed suggests that the current CT scanners can be enhanced with quantitative reconstruction ability by only updating the reconstruction algorithm. With quantitative CT, misdiagnoses can be reduced with artifact-free images, and the quantitative assessment of CT images can be improved.

If an unknown material (e.g., iron) does not possess prominent K-edges in the x-ray spectrum range, its attenuation coefficient then can be decomposed into two bases (i.e., photoelectric component and Compton component) or two distinct materials (e.g., water and bone). As there is one unknown decomposition coefficient for each base, the solution space is doubled with respect to that of the conventional FBP algorithm. For the dual energy approaches, a patient is scanned by a dual energy scanner to obtain more information. Such that the decomposition coefficients can be computed to enable quantitative reconstruction of this unknown material, but the dual energy scanner increases the cost and the complexity of the acquisition.

In comparison, the iterative-based base material approaches assume that the scanned object is composed of known base materials (e.g., water and bone) and their mixtures (i.e., water-bone mixtures). The attenuations of the base materials can only be used to accurately compute the attenuation properties of the base materials and their mixtures, but not to accurately predict the attenuation properties of the other materials (e.g. iron). For the previous algorithms limited base materials are incorporated, so errors arise for the other materials. In this work, a wide range of base materials were incorporated to greatly reduce this limitation, so that gradation of attenuation coefficients for various tissue types can be broadly and accurately sampled. As the attenuation at reference energy $\mu(E_0)$ is used to compute the decomposition coefficients based on a predefined decomposition equation (Eq. 5) via interpolation, the size of the solution space is the same as that of the conventional FBP algorithm. Therefore, techniques disclosed herein can be applied on a CT to reconstruct artifact-free images.

For the purpose of reconstruction stability, the two bases selected in the dual energy approaches should not be too close to each other. In contrast, close base materials will not induce reconstruction stability problem in the iterative-based base material approaches, as base materials are mainly used to estimate the attenuation properties of their mixtures via interpolation. In fact, close base materials can provide more accurate information to reduce approximation errors, as observed through the base material transition test.

In order to improve the convergence stability, the disclosed piFBP algorithms can reduce two adverse factors, i.e., the noise in the correction volume due to quantum noise and electronic noise, and the inherent error due to the Fourier cut-off frequency and the filter type. The noise was suppressed using a smoothing kernel and the inherent error was reduced using a ram-lak filter. In comparison, Vedula and Munshi proposed a different strategy to improve the convergence stability. They used softer filters (e.g., Hamming filter) to reduce the influence of the noise. The inherent error induced by the softer filters was then corrected by an inherent error correction procedure. As such, they can use a piFBP-W-type (Eq. 14) backward updating formula to remove the beam hardening artifacts. However, as their algorithm was mainly designed for the non-destructive test (NDT), the scanned objects could only consist of distinct base materials. The adaptive base material decomposition method proposed in this work can be employed as an extension of that work, so that that algorithm can be applied in diagnostic radiology to account for the mixtures of the base materials (e.g., water-bone mixtures). Quantitative comparison of the reconstruction performance of the two different strategies remains topics for future investigation.

The smoothing kernel in Equation 17 was not optimized in this work, as this study primarily aimed to improve the material quantification performance. An adaptive smoothing kernel may be used to not only reduce image noise but also maintain anatomical details. Further, techniques disclosed herein may be extended to CT angiography and CT perfusion, so that BH artifacts due to contrast agent materials (e.g., Iodine) can be eliminated, and quantitative concentrations of contrast agent can be retrieved for diagnostic analyses.

In quantitative myocardial CT perfusion imaging, iodine as contrast agent is administered to the patient through intravenous injection, which can increase the absorption of x-rays and enhance the visibility of vascular structures and organs. By recording the transit of the iodine through the vasculature and myocardium, time-attenuation curves (TACs) in the aorta (or left ventricle blood pool) and myocardium can be obtained, from which myocardial blood flow (MBF) and myocardial blood volume (MBV) can be further derived to quantitatively estimate ischemic regions. Therefore, accurately reconstructing the iodine concentration is of great importance to the quantitative assessment of the myocardial CT perfusion imaging.

Disclosed herein are pSART algorithms that incorporate the knowledge of various base materials (e.g., fat, breast, soft tissue, bone, and iodine) and the spectrum information into the reconstruction process. As each voxel is allowed to be a mixture of two most suitable base materials, the subtle attenuation differences of bones of different densities and of iodinated voxels of different concentrations can be accurately modeled in the reconstruction process to enable precise quantification. Instead of segmenting the images into three distinct regions, i.e., soft tissue, bone, and iodine, methods disclosed herein only need to coarsely segment the images into two types of regions, i.e., non-bone regions and non-iodine regions, which can be easily achieved by the current segmentation techniques. As no registration is involved, disclosed methods are not influenced by patient motion artifacts. Further described herein are a series of simulations and a phantom experiment to explore the accuracy and convergence properties of the proposed algorithm.

Symbols and their definitions used herein are provided in Table 8.

TABLE 8

Symbols and definitions.

| Symbols | Definitions |
| --- | --- |
| $E_0$ | Reference energy, at which the mono-energetic image will be reconstructed |
| $I_{se}$ | X-ray photon intensity at the e-th energy bin of the s-th spectrum |
| $N_E$ | Total number of the spectrum energy bins |
| $N_M$ | Total number of the base materials |
| $N_R$ | Total number of the x-ray paths from x-ray source to detector modules |
| $N_S$ | Total number of the spectra |
| $N_V$ | Total number of the voxels of the volume |
| $T_v$ | Region map of the v-th voxel |
| $Y_{rs}$ | CT Measurement through the r-th x-ray with the s-th incident spectrum |
| $\bar{Y}_{rs}$ | Estimated measurement through the r-th x-ray with the s-th incident spectrum |
| $a_{rv}$ | Contribution of the v-th voxel to the r-th ray |
| $c_v$ | Iodine concentration of the v-th voxel |
| e | Index for spectrum energy bins |
| $l_{rm}$ | Accumulated effective length of the m-th material along the r-th ray |
| m | Index for the base materials |

TABLE 8-continued

Symbols and definitions.

| Symbols | Definitions |
|---|---|
| r | Index for the x-ray paths |
| s | Index for the spectra |
| $t_v$ | Attenuation coefficient of the v-th voxel at reference energy $E_0$ |
| $t(\vec{x})$ | Attenuation coefficient at location $\vec{x}$ at reference energy $E_0$ |
| v | Index for the voxels |
| $\varepsilon$ | Energy level within the spectrum range |
| $\mu_m$ | Attenuation coefficient of the m-th base material at reference energy $E_0$ |
| $\mu_{me}$ | Attenuation coefficient of the m-th base material at the e-th energy bin |
| $\mu_m(\varepsilon)$ | Attenuation coefficient of the m-th base material at energy $\varepsilon$ |
| $\rho_m$ | Density of the m-th base material |
| $\rho_v$ | Density of the v-th voxel |

It is assumed herein that Yrs are the poly-energetic measurements for the r-th ray (r=1, . . . , $N_R$) with the s-th (s=1, . . . , $N_S$) incident spectrum, where $N_R$ and $N_S$ are the total number of the x-ray paths and spectra, respectively. The goal is to reconstruct a target volume, as individual indexed voxel of $t_v$ (v=1, . . . , $N_V$) in terms of the attenuation coefficient at a reference mono-energetic energy of $E_0$, where $N_V$ is the total numbers of the unknown voxels. The materials in the object are assumed to meet three requirements:

1) the object consists of $N_M$ indexed base materials with known attenuation coefficients $\mu_m(\varepsilon)$ (m=1, . . . , $N_M$), where m=1 corresponds to air;
2) each voxel can only be a mixture of two base materials; and
3) a region map $T_v$ (v=1, . . . , $N_V$) is available, defined as $$T_v = \begin{cases} 0, & \text{Non-bone voxel,} \\ 1, & \text{Non-iodine voxel} \end{cases} \quad (22)$$

Figure 12:
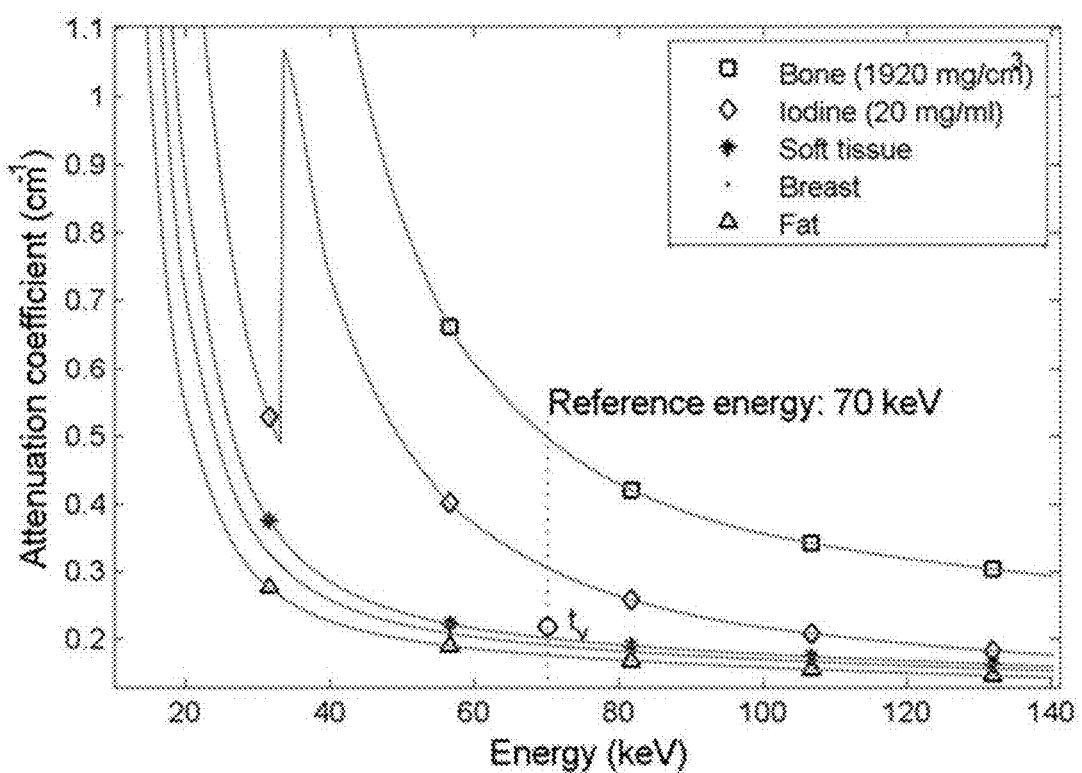
FIG. 12 is a graph showing the attenuation coefficients of those base materials in the diagnostic x-ray energy range.

In the context of quantitative myocardial CT perfusion imaging, the materials normally utilized to fulfill the first requirement include air (m=1), fat (m=2), breast (m=3), soft tissue (which has similar attenuation properties with blood, m=4), iodine solution (20 mg/ml blood-iodine solution, m=5), and bone (1920 mg/cm³ soft tissue-calcium solution, m=6). FIG. 12 is a graph showing the attenuation coefficients of those base materials in the diagnostic x-ray energy range. Most of the poly-energetic reconstruction algorithms use water to approximate body tissues. However, due to the difference of the attenuation properties, the CT numbers of fat and breast in the reconstructed images can deviate from the expected values, which can affect not only the accuracy of those voxels, but also in turn the accuracy of the other voxels within the iterative reconstruction process. By incorporating fat and breast into the reconstruction algorithm, the gradation of attenuation coefficients for various tissue types can be more accurately sampled. For convenience, the 20 mg/ml iodine was used as a base material, since the maximum iodine concentration in the vascular space is usually below 20 mg/ml.

The second requirement allows for the subtle attenuation differences of bones and iodine concentrations to be accurately accounted. This requirement also helps reduce the complexity of the reconstruction model by ruling out mixtures formed with more than two materials. Piece-wise linear interpolation is able to be employed to estimate the attenuation properties of any given voxel.

As the attenuation curves of bone and iodine have overlap regions above the attenuation curve of soft tissue (FIG. 12), the third requirement helps the algorithm differentiate bone and iodine and ensures that the correct attenuation curves are utilized for these two distinct materials. Instead of requiring to accurately segment the images into three types of regions, i.e., soft tissue regions, bone regions, and iodine regions, it is only required to coarsely segment the images into non-bone regions and non-iodine regions in accordance with embodiments of the present disclosure. In the non-iodine regions, materials can include any body tissues except iodine. Thereby voxel values larger than the attenuation coefficient value of soft tissue are automatically interpreted as mixtures of bone and soft tissue. Similarly, in the non-bone regions, voxels larger than the attenuation coefficient value of soft tissue are automatically interpreted as mixtures of iodine and soft tissue. In the myocardial perfusion images, the bones are limited to sternum, ribs, and thoracic vertebrae, and those bone structure can be readily segmented based on anatomical knowledge. With the segmented bone structure, the region type $T_v$ of the v-th voxel is set to one to bone structures, or zero otherwise.

To fully explain the poly-energetic forward ray-tracing strategies, the following are described herein: iodine region [$\mu_4, \mu_5$], bone region [$\mu_5, \mu_6$], and body tissue range [$\mu_1, \mu_4$], where $\mu_m$ is the m-th material attenuation coefficient at any preselected reference energy $E_0$.

With respect to iodine region, when $t_v \in [\mu_4, \mu_5]$ and $T_v=0$, the v-th voxel can be regarded as the mixture of the base materials of blood and iodine solution (20 mg/ml). Its attenuation coefficient is estimated as $$\mu(t_v, \varepsilon) = \frac{\mu_5 - t_v}{\mu_5 - \mu_4}\mu_4(\varepsilon) + \frac{t_v - \mu_4}{\mu_5 - \mu_4}\mu_5(\varepsilon). \quad (23)$$

Equation 23 can also be rewritten equivalently in the form of mass attenuation coefficient as $$\mu(t_v, \varepsilon) = \left(\frac{\mu_5 - t_v}{\mu_5 - \mu_4}\rho_4\right)\left[\frac{\mu(\varepsilon)}{\rho}\right]_4 + \left(\frac{t_v - \mu_4}{\mu_5 - \mu_4}\rho_5\right)\left[\frac{\mu(\varepsilon)}{\rho}\right]_5, \quad (24)$$

where $\rho_m$ (m=1, . . . , $N_M$) is the density of the base materials. As the base material iodine solution (20 mg/ml) is essentially the mixture of blood and iodine element, its attenuation coefficient is calculated as $$\rho_5\left[\frac{\mu(\varepsilon)}{\rho}\right]_5 = \rho_4\left[\frac{\mu(\varepsilon)}{\rho}\right]_4 + 20 \text{ mg/ml}\left[\frac{\mu(\varepsilon)}{\rho}\right]_{Iodine}. \quad (25)$$

Substitute the above equation into Equation 22, and we get $$\mu(t_v, \varepsilon) = \rho_4\left[\frac{\mu(\varepsilon)}{\rho}\right]_4 + \left(\frac{t_v - \mu_4}{\mu_5 - \mu_4} \times 20 \text{ mg/ml}\right)\left[\frac{\mu(\varepsilon)}{\rho}\right]_{Iodine}. \quad (26)$$

Therefore, the iodine concentration or density in the v-th voxel is computed as $$c_v = \frac{t_v - \mu_4}{\mu_5 - \mu_4} \times 20 \text{ mg/ml}. \quad (27)$$

With respect to bone region, when $t_v \in [\mu_5, \mu_6]$ and $T_v = 1$, the v-th voxel is decomposed into the base materials of soft tissue and bone and the attenuation coefficients of those voxels are estimated as $$\mu(t_v, \varepsilon) = \frac{\mu_6 - t_v}{\mu_6 - \mu_4} \mu_4(\varepsilon) + \frac{t_v - \mu_4}{\mu_6 - \mu_4} \mu_6(\varepsilon). \quad (28)$$

Based on the mixture model, the bone mineral density $\rho_v$ in the v-th voxel is assessed as $$\rho_v = \frac{t_v - \mu_4}{\mu_6 - \mu_4} \times 1920 \text{ mg/cm}^3, \quad (29)$$

where 1920 mg/cm$^3$ is the density of the bone base material.

When $t_v \in [\mu_1, \mu_4]$, the attenuation coefficient is estimated as $$\mu(t_v, \varepsilon) = \sum_{m=1,2,3} \chi_{[\mu_m, \mu_{m+1})}(t_v) \left[ \frac{\mu_{m+1} - t_v}{\mu_m - \mu_m} \mu_m(\varepsilon) + \frac{t_v - \mu_m}{\mu_{m+1} - \mu_m} \mu_{m+1}(\varepsilon) \right], \quad (30)$$

where step function $\chi_{[a,b)}$ is defined as $$\chi_{[a,b)}(t) = \begin{cases} 1 & t \in [a, b) \\ 0 & t \notin [a, b) \end{cases}. \quad (31)$$

As shown in FIG. 12, the attenuation coefficients of the body materials, such as fat, breast, and soft tissue, are very similarly, so interpolation is used to estimate the attenuation coefficients of the other organ tissues, such as brain, muscle (skeletal), lung, and ovary. In prior literature, these tissues are generally simplified as water. Herein, they can be decomposed into soft tissue and breast tissue base materials to achieve higher accuracy.

Combining Equations 23, 29, and 30, the attenuation coefficient of the v-th voxel is determined as $$\mu(t_v, \varepsilon) = \sum_{m=1,2,3} \chi_{[\mu_m, \mu_{m+1})}(t_v) \left[ \frac{\mu_{m+1} - t_v}{\mu_{m+1} - \mu_m} \mu_m(\varepsilon) + \frac{t_v - \mu_m}{\mu_{m+1} - \mu_m} \mu_{m+1}(\varepsilon) \right] \quad (32)$$

$$\chi_{[\mu_4, \mu_5)}(t_v) \left[ \frac{\mu_5 - t_v}{\mu_5 - \mu_4} \mu_4(\varepsilon) + \frac{t_v - \mu_4}{\mu_5 - \mu_4} \mu_5(\varepsilon) \right] (1 - T_v) +$$

$$\chi_{[\mu_4, \mu_6)}(t_v) \left[ \frac{\mu_6 - t_v}{\mu_6 - \mu_4} \mu_4(\varepsilon) + \frac{t_v - \mu_4}{\mu_6 - \mu_4} \mu_6(\varepsilon) \right] T_v.$$

To reduce the computational time, the base material range indices and the corresponding effective lengths for every voxel may be calculated and stored in matrices before performing forward ray tracing, with which, the accumulated effective lengths across base materials are computed through one forward ray tracing as $$\int_{L_r} \mu(t(\vec{x}), \varepsilon) dl \approx \sum_{v=1,\ldots,N_V} a_{rv} \mu(t_v, \varepsilon) = \sum_{m=1,\ldots,N_M} l_{rm} \mu_m(\varepsilon), \quad (33)$$

where $a_{rv}$ denotes the elements of the system matrix, and $l_{rm}$ denotes the accumulated effective length of the m-th material for the r-th ray ($r = 1, \ldots, N_R$), $$l_{rm} = \sum_{v=1,\ldots,N_V} a_{rv} \chi_{[\mu_m, \mu_{m+1})}(t_v) \times \quad (34)$$

$$\begin{cases} \frac{\mu_{m+1} - t_v}{\mu_{m+1} - \mu_m} & m = 1 \\ \frac{\mu_{m+1} - t_v}{\mu_{m+1} - \mu_m} + \frac{t_v - \mu_{m-1}}{\mu_m - \mu_{m-1}} & m = 2, 3 \\ \frac{(\mu_{m+2} - t_v) T_v}{\mu_{m+2} - \mu_m} + \frac{(\mu_{m+1} - t_v)(1 - T_v)}{\mu_{m+1} - \mu_m} + \frac{t_v - \mu_{m-1}}{u_m - \mu_{m-1}} & m = 4 \\ \frac{(t_v - \mu_m)(1 - T_v)}{\mu_m - \mu_4} & m = 5 \\ \frac{(t_v - \mu_m) T_v}{\mu_m - \mu_4} & m = 6 \end{cases}.$$

The accumulated effective length $l_{rm}$ are repeatedly used to fast and accurately compute the energy integral calculation as $$\overline{Y}_{rs} = \int I_s(\varepsilon) \exp\left[ -\int_{L_r} \mu(t(\vec{x}), \varepsilon) dl \right] d\varepsilon \quad (35)$$

$$\approx \sum_{e=1,\ldots,N_E} I_{se} \exp\left[ -\sum_{m=1,\ldots,N_M} l_{rm} \mu_{me} \right] \Delta e,$$

where $I_{se}$ denotes the e-th energy bin ($e = 1, \ldots, N_E$) of the s-th spectrum ($s = 1, \ldots, N_S$) and $N_E$ is the total number of the discrete energy bins.

With the estimated poly-energetic projections, both algebraic reconstruction algorithms and statistical reconstruction algorithms can be utilized to iteratively update voxels along the x-ray paths. Here, the SART was used as $$t_v^{(k+1)} = t_v^{(k)} + \frac{\sum_{rs} a_{rv} \left( \frac{\ln \overline{Y}_{rs}^{(k)} - \ln Y_{rs}}{\sum_{v'} a_{rv'}} \right)}{\sum_r a_{rv}}. \quad (36)$$

SART was initially designed for mono-energetic reconstruction based on the linear relationship between measured data $\ln Y_{rs}$ and linear attenuation coefficients. But when applying this algorithm to non-mono-energetic data, the inconsistency between the data and the reconstruction algorithm causes BH artifacts. The proposed poly-energetic ray tracing approach efficiently solves this inconsistency problem, and helps the reconstructed volume converge to an artifact-free image. Once image $t_v$ is reconstructed at reference energy $E_0$, the value of each pixel can be shifted along the interpolated attenuation coefficient curves to generate images at any other target energy. Generally, a high keV reference energy is preferred for fast convergence as described herein, and a target energy of 70 keV is used in this study as in many current clinical CT applications.

A fan beam geometry was simulated with an equiangular arc detector. Two phantoms (a cylindrical phantom and a thorax phantom) were used to generate poly-energetic projection data. The simulation parameters are listed in 9. Quantum noise corresponding to $4.0 \times 10^5$ photons per detector pixel was added to the projection data. In this work, no inhomogeneous bow-tie filtering and scattered radiation were taken into consideration. All simulations were conducted on Duke Blue Devil GPU Cluster with NVIDIA Tesla C1060 CPUs, which consists of 30 multiprocessors (each with eight SIMD processing cores) and 4 GB of memory.

TABLE 9

Simulation parameters used in the validation study.

| Parameter name | Value |
| --- | --- |
| Source-to-detector distance | 1085.6 mm |
| Source-to-object distance | 595.0 mm |
| Number of detector bins | 736 |
| Detector size at iso-center | $0.60 \times 0.60$ mm$^2$ |
| Total photon number per detector | $4.0 \times 10^5$ photons |
| Number of energy bins | 280 |
| Energy bine size | 0.5 keV |
| Number of projections | 1152 |

A cylindrical phantom (FIG. 13) consisting of air, fat, breast tissue, soft tissue, bone (1200 mg/cm$^3$), and iodinated contrast medium (8 mg/ml) was used in the study. Six simulation tests were conducted on this phantom to assess the reconstruction abilities of pSART compared with SART. All the SART reconstructions in this paper used water correction technique.

Figure 13:
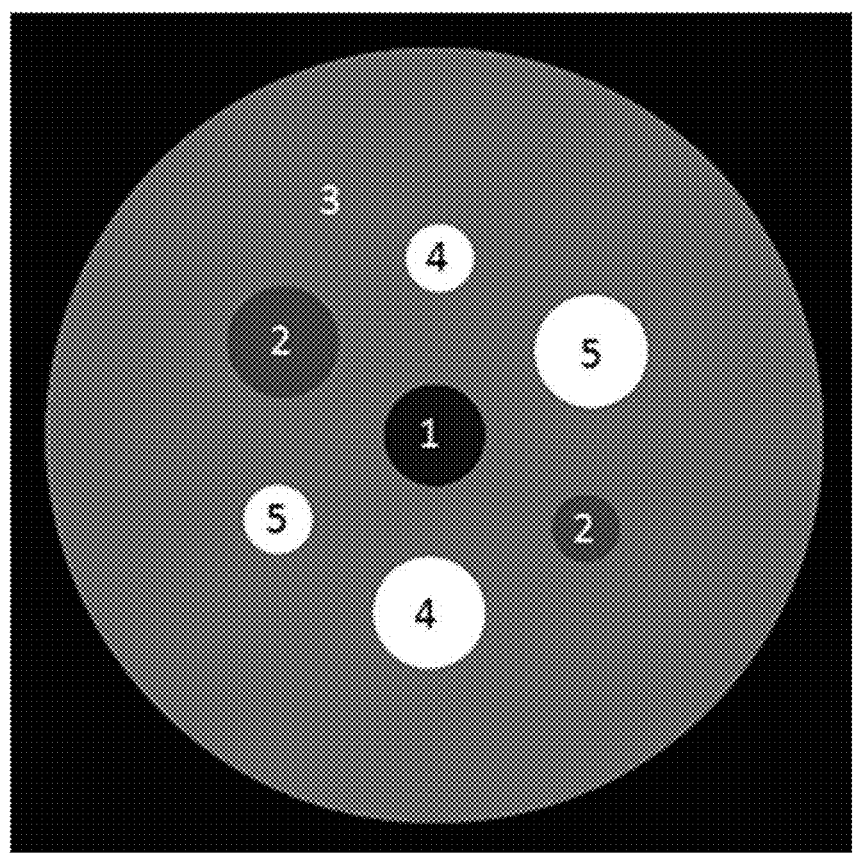
FIG. 13 is an image showing a definition of the cylindrical phantom with fat, breast tissue, soft tissue, iodine, and bone.

FIG. 13 is an image showing a definition of the cylindrical phantom (0.2×0.2 mm$^2$ per pixel) with (1) fat, (2) breast tissue, (3) soft tissue, (4) 8 mg/ml iodine, and (5) 1200 mg/cm$^3$ bone. This phantom was formed in four different cross sectional sizes, i.e., 16, 23, 30, and 37 cm in diameter.

The first simulation test aimed to validate the reconstruction stabilities in terms of material diversity with a 23 cm cylindrical phantom and a 100 kVp spectrum. A base material transition test was conducted in the second test to investigate the benefit of more base materials. The projection dataset acquired in the first test was reconstructed by increasing the number of the base materials. The base material groups used in this test are listed in Table 4. The third test focused on the reconstruction stability in terms of phantom size. The cylindrical phantom was formed into four sizes, i.e., 16, 23, 30, and 37 cm diameter, and imaging was simulated with a 100 kVp spectrum. In the fourth simulation test, we tested the reconstruction stability as a function of changes of the spectrum (80, 100, 120, and 140 kVp). In the fifth simulation test, we compared the convergence properties of the SART and pSART with three different spectra (80, 100, and 140 kVp). In addition, we also compared the convergence property of pSART at two reference energies (70 and 140 keV). In the last simulation test, the impact of a possible difference between the actual and the assumed spectra was investigated. Nineteen mismatch spectra were obtained by softening or hardening the correct spectrum of 100 kVp through adjusting the thickness of the inherent aluminum filtration of the x-ray tube. The normalized root mean square differences (NRMSDs) of these mismatch spectra ranged from −9% to 9% with an interval of 1%. Here, negative NRMSDs indicate softened spectra and positive NRMSDs indicate hardened spectra. The parameters used in the above six simulation tests are summarized in Table 10.

TABLE 10

Parameter summary of simulation tests for the cylindrical phantom.

| Simulation tests | Varying parameters | Fixed parameters | Individual parameters |
| --- | --- | --- | --- |
| Material test | — | Phantom size: 23 cm<br>Spectrum: 100 kVp | SART: water correction<br>pSART: $E_0$ = 70 keV |
| Base material transition test | Base material groups:<br>Listed in Table | Phantom size: 23 cm<br>Spectrum: 100 kVp | SART: water correction<br>pSART: $E_0$ = 70 keV |
| Phantom size test | Phantom size:<br>16, 23, 30, and 37 cm | Spectrum: 100 kVp | SART: water correction<br>pSART: $E_0$ = 70 keV |
| Spectrum type test | X-ray spectrum:<br>80, 100, 120, 140 kVp | Phantom size: 23 cm | SART: water correction<br>pSART: $E_0$ = 70 keV |
| Convergence test | X-ray spectrum:<br>80, 100, 140 kVp | Phantom size: 23 cm | SART: water correction<br>pSART: $E_0$ = 70 keV, 140 keV |
| Spectrum mismatch test | Mismatch spectrum:<br>NRMSD = −9%, . . . , 9% | Phantom size: 23 cm<br>Spectrum: 100 kVp | pSART: $E_0$ = 70 keV |

TABLE 11

Base material groups used in the base material transition test.

| | Group 1 | Group 2 | Group 3 | Group 4 | Group 5 |
| --- | --- | --- | --- | --- | --- |
| Base material | Water | Soft tissue<br>Iodine | Soft tissue<br>Iodine<br>Bone | Fat<br>Soft tissue<br>Iodine<br>Bone | Fat<br>Breast<br>Soft tissue<br>Iodine<br>Bone |

Figure 14:
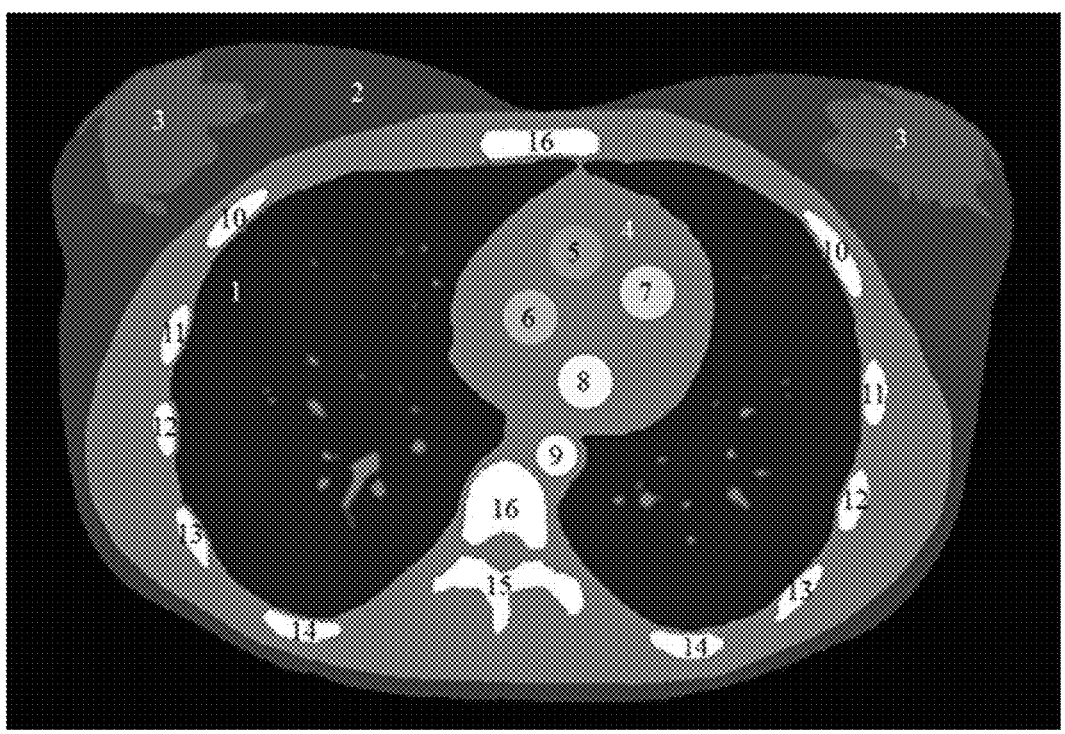
FIG. 14 is an image showing a definition of the anthropomorphic thorax phantom.

In order to further validate the reconstruction algorithm, real CT data from the database of The Cancer Imaging Archive (TCIA, http://www.cancerimagingarchive.net/) was used to create a more complex and realistic anthropomorphic thorax phantom (FIG. 14). Besides the body tissues such as lung, fat, breast, soft tissue, this phantom was supplemented with iodinated inserts of five different concentrations (3, 6, 9, 12, and 15 mg/ml), and bones of seven different densities (200, 400, 600, 800, 1000, 1200, and 1400 mg/cm$^3$). Using this phantom, the reconstruction performance of pSART was compared with that of SART.

FIG. 14 illustrates an image showing a definition of the anthropomorphic thorax phantom (0.14×0.14 mm$^2$ per pixel, 2048×1400 pixels) with (1) lung, (2) fat, (3) breast tissue, (4)

soft tissue, (5) 3 mg/ml iodine, (6) 6 mg/ml iodine, (7) 9 mg/ml iodine, (8) 12 mg/ml iodine, (9) 15 mg/ml, (10) 200 mg/cm³ bone, (11) 400 mg/cm³ bone, (12) 600 mg/cm³ bone, (13) 800 mg/cm³ bone, (14) 1000 mg/cm³ bone, (15) 1200 mg/cm³ bone, and (16) 1400 mg/cm³ bone. Phantom measurements were acquired on a clinical CT scanner (Siemens Somatom Definition Flash, Siemens Healthcare, Germany). An axial scan mode with fixed focal spot, a 0.5s rotation time, a nominal tube voltage of 100 kVp, and a tube current of 100 mAs was used.

Figure 15:
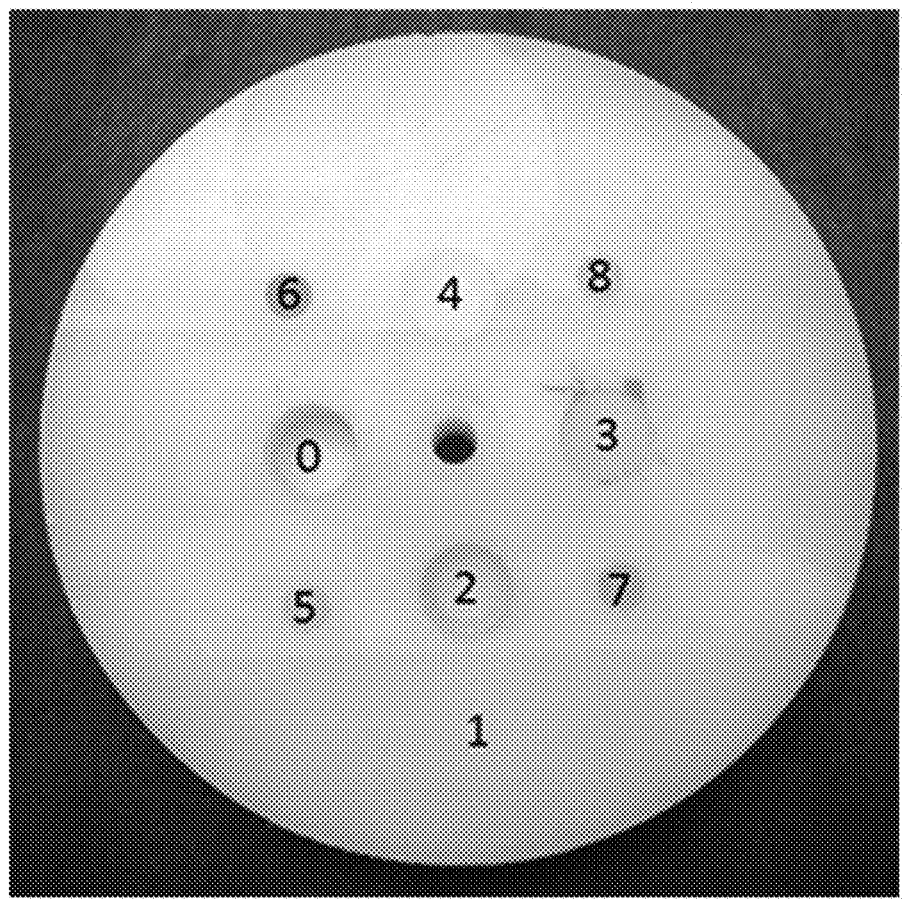
FIG. 15 is an image of a definition of the mercury phantom.

A 22 cm diameter Mercury phantom was employed, which contained nine different materials as shown in FIG. 15, which is an image of a definition of the mercury phantom with (0) air, (1), polyethylene, (2) polystyrene, (3) acrylic, (4) Teflon, (5) 2.2 mg/ml Iodine, (6) 4.3 mg/ml Iodine, (7) 6.4 mg/ml Iodine, (8) 8.5 mg/ml Iodine. The material information is listed in Table 12. As the attenuation coefficient curves of polyethylene, polystyrene, acrylic, and Teflon have similar sequence order with those of fat, breast, soft tissue, and bone, these polymers were classified into non-iodine region. The iodine inserts simulated mixtures of iodine and breast tissue and were classified into non-bone region using breast tissue and 20 mg/ml breast-iodine mixture as base materials. With the composition information of this phantom already known, we were able to quantitatively validate the accuracy of pSART algorithm.

values than water, such as iodine and bone, tended to be overestimated. The overall percent errors were within a 2% interval [−1.4%, 2.6%]. In comparison, the overall percent errors of pSART were within a negligible interval [−0.1%, 0.1%]. Table 14 correspondingly compared the iodine concentration and bone density estimated by SART and pSART to further validate the reconstruction accuracy of the pSART algorithm.

TABLE 13

Relative errors in terms of the attenuation coefficient for different materials in the cylindrical phantom.

| | Fat | Breast tissue | Soft tissue | Iodine (8 mg/ml) | Bone (1200 mg/cm³) |
|---|---|---|---|---|---|
| SART | −1.4% | −0.2% | 0.2% | 2.2% | 2.6% |
| pSART | −0.1% | −0.1% | −0.1% | 0.1% | 0.1% |

TABLE 12

Material information of the Mercury phantom.

| | Polyethylene | Polystyrene | Acrylic | Teflon | Iodine 2.2 mg/ml | Iodine 4.3 mg/ml | Iodine 6.4 mg/ml | Iodine 8.5 mg/ml |
|---|---|---|---|---|---|---|---|---|
| Density (mg/ml) | 938 | 1044 | 1164 | 2163 | 991 | 993 | 995 | 998 |
| HU | −90 | −32 | 131 | 994 | 57 | 112 | 167 | 222 |

Figure 16A:
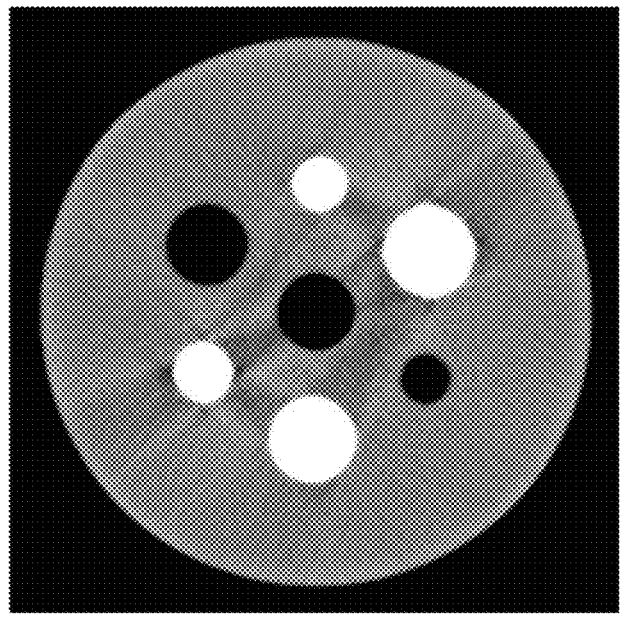
FIGS. 16A and 16B are images reconstructed by SART and pSART algorithms from the same projection dataset.
Figure 16B:
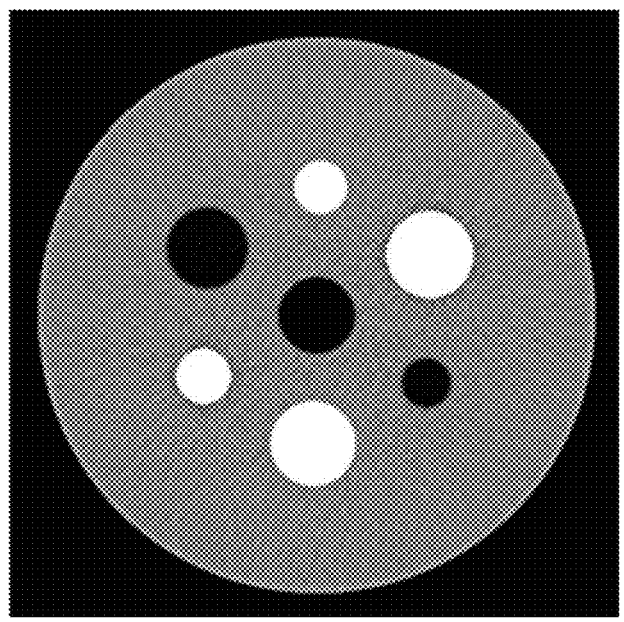

FIGS. 16A and 16B are images reconstructed by SART and pSART algorithms from the same projection dataset, which was acquired with the 23 cm cylindrical phantom and 100 kVp spectrum. Both of them were initialized with zero values and were reconstructed with 120 iterations. The images are shown with a window width of 160 HU and a window level of 70 HU. Though water correction was applied to SART (FIG. 16A), the visible cupping artifacts (brighter pixels at the soft tissue border) were not able to be completely eliminated. Besides, the dark streak artifacts between the bones and iodinated inserts further degraded the image quality. FIG. 16B was reconstructed by the proposed pSART algorithm at the reference energy 140 keV and target energy 70 keV. Compared with FIG. 16A, no degradation due to BH artifacts was observable, which implies that pSART was more accurate than SART.

In FIGS. 16A and 16B, images were reconstructed by water-corrected SART and pSART, respectively, from the same projection dataset, which was acquired with the 23 cm diameter cylindrical phantom and 100 kVp spectrum. Both of them were initialized with zero values and reconstructed with 120 iterations. The images were 512×512 with a voxel size of 0.5×0.5 mm².

Relative errors in terms of the attenuation coefficient for different materials of the cylindrical phantom are summarized in Table 13. For SART, because of the water correction, the soft tissue had relatively small percent error. In contrast, materials with less attenuation coefficient values than water, such as fat and breast tissue, tended to be underestimated; materials with larger attenuation coefficient

TABLE 14

Iodine concentration and bone density evaluated by SART and pSART.

| | Iodine (8 mg/ml) | Bone (1200 mg/cm³) |
|---|---|---|
| SART | 8.9 | 1263 |
| pSART | 8.0 | 1201 |

Figure 17:
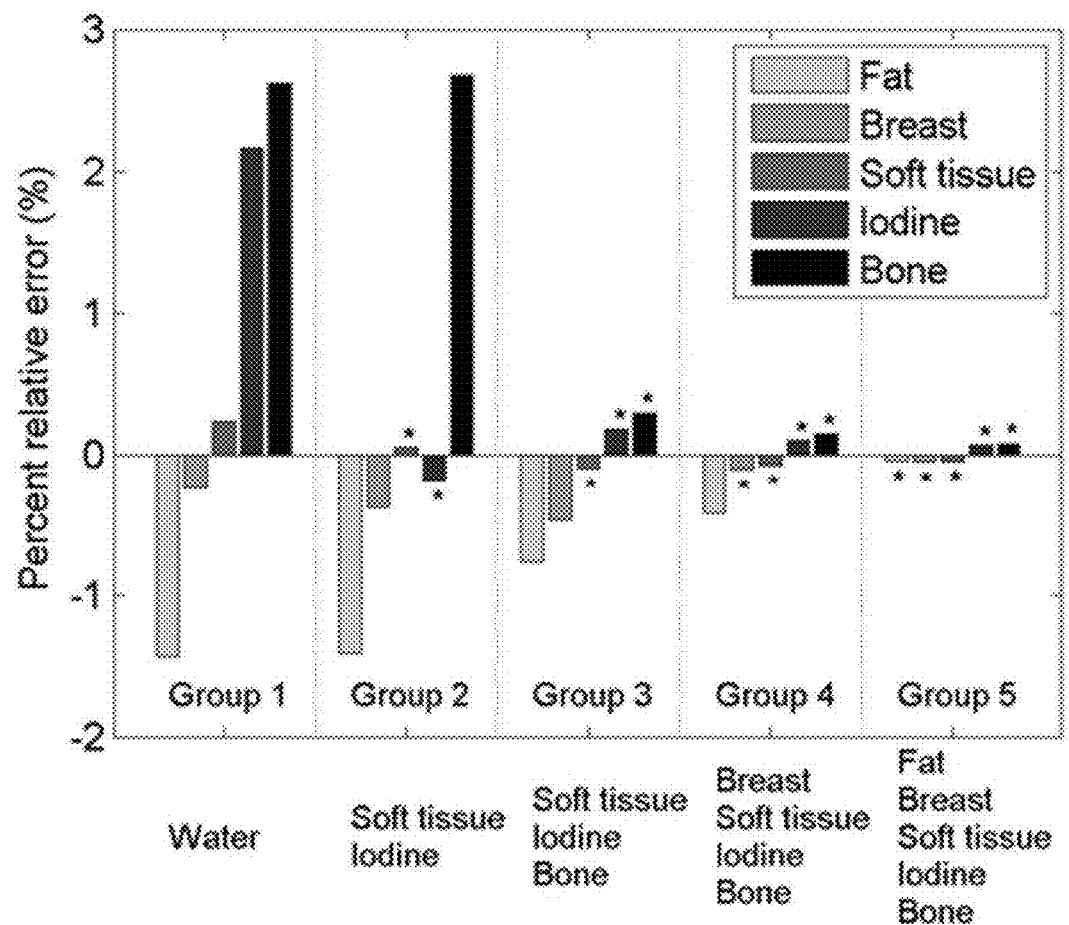
FIG. 17 is a graph of simulation results of the base material transition test.

The results of the base material transition test are plotted in FIG. 17, which illustrates a graph of simulation results of the base material transition test. The columns without stars indicate that the corresponding materials are not base materials. The columns with stars indicate that the corresponding materials are base materials. Referring to the indices of Table 13, when only water was used as the base material (group 1), the attenuations of soft tissue and breast had small relative errors. However, other materials yielded relatively large errors due to the large difference in attenuation with water. Adding soft tissue and iodine as base materials (group 2) reduced their relative errors, especially for the iodine. With the addition of bone (group 3), the relative error associated with bone was further reduced. The relative error of fat was also reduced because the strong BH effect due to bone was suppressed. Adding breast as a base material (group 4) reduced the relative error of breast to a negligible level. Note that fat also showed a small improvement as in this case fat was interpreted as low density breast tissue instead of low density soft tissue as the attenuation property of fat is closer to that of the breast. Finally, adding fat as a base material (group 5) reduced fat's relative error to a negligible level as well.

Figure 18A:
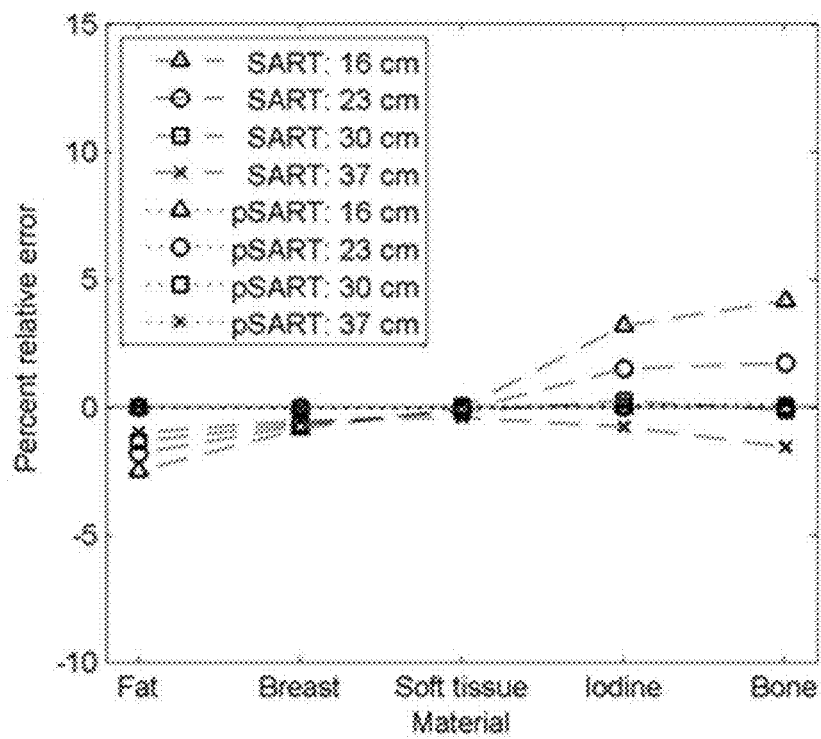
FIGS. 18A and 18B illustrate graphs of phantom size test results and spectrum type test results.
Figure 18B:
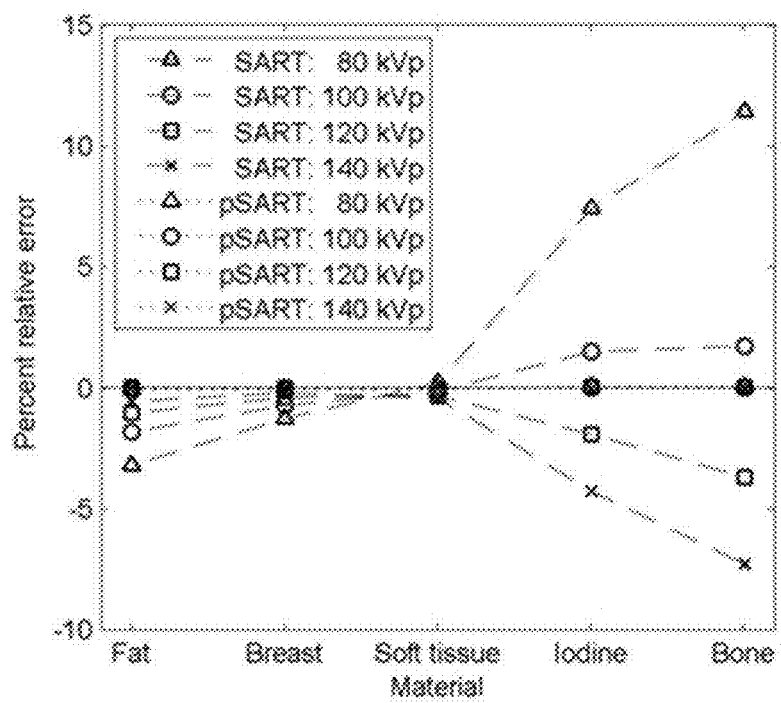

The effects of the phantom size and spectrum type are presented in FIGS. 18A and 18B, which illustrate graphs of phantom size test results (FIG. 18A) and spectrum type test results (FIG. 18B). Percent relative errors are plotted for different materials (fat, breast tissue, soft tissue, 8 mg/ml iodine, and 1200 mg/cm3 bone) and reconstruction algorithms (dashed line: SART; dotted line: pSART). For SART, soft tissue maintained low relative percent errors due to water correction; fat and breast tissue were continuously underestimated for all phantom sizes and spectra; Iodine and bone showed more complicated nonlinear changes—they were overestimated for certain size phantoms or spectra, but underestimated for others. The large variation due to the spectrum (i.e., [−7.5%, 12.1%]) compared to that due to the phantom size (i.e., [−2.5%, 4.5%]) indicated that spectrum had a larger influence on the accuracy of voxel values. However, compared to SART, pSART yielded negligible relative errors (i.e., [−0.1%, 0.1%]) for all materials in the two tests and showed good reconstruction stability across phantom size and spectrum type.

Figure 19A:
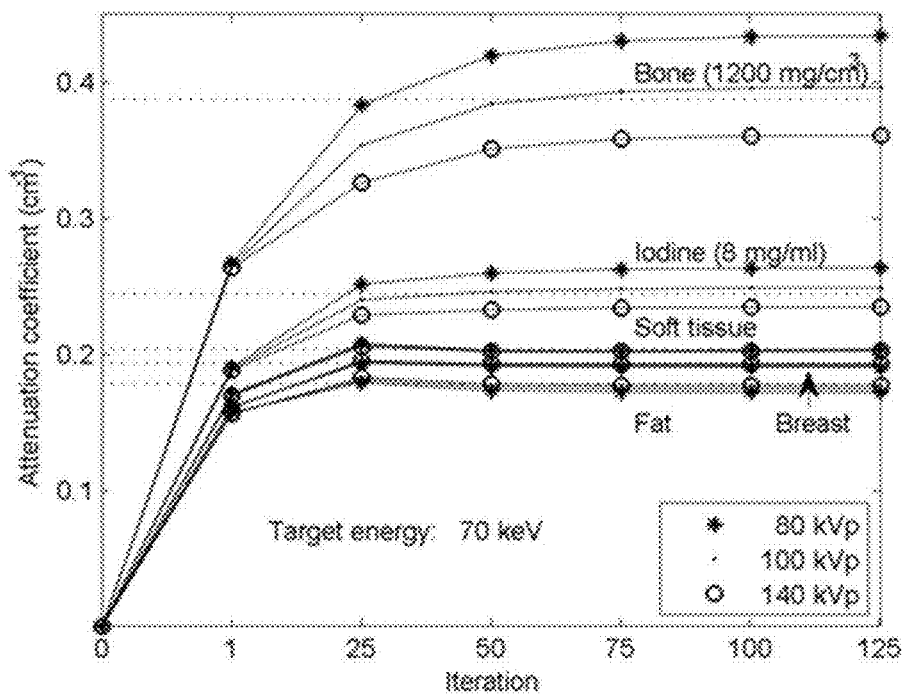
FIGS. 19A-19C illustrate graphs showing convergence test results for different spectra.
Figure 19B:
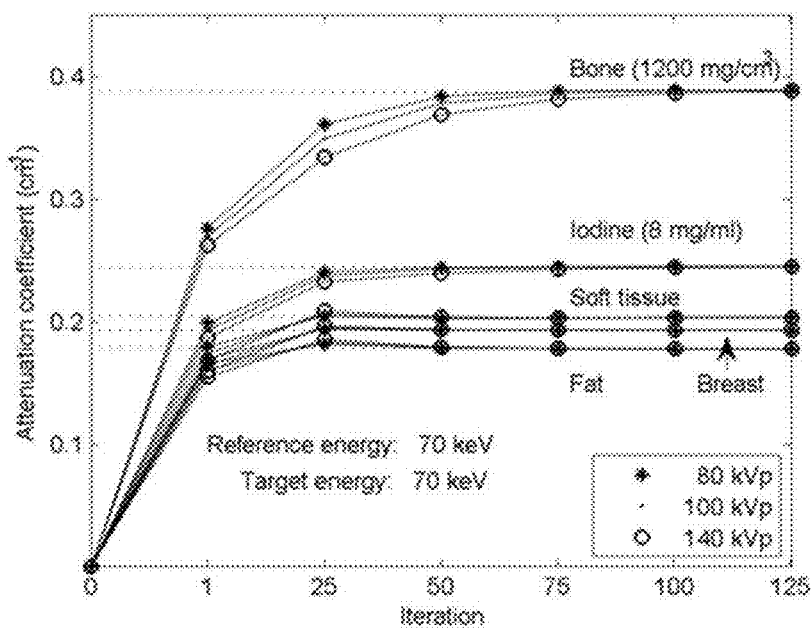
Figure 19C:
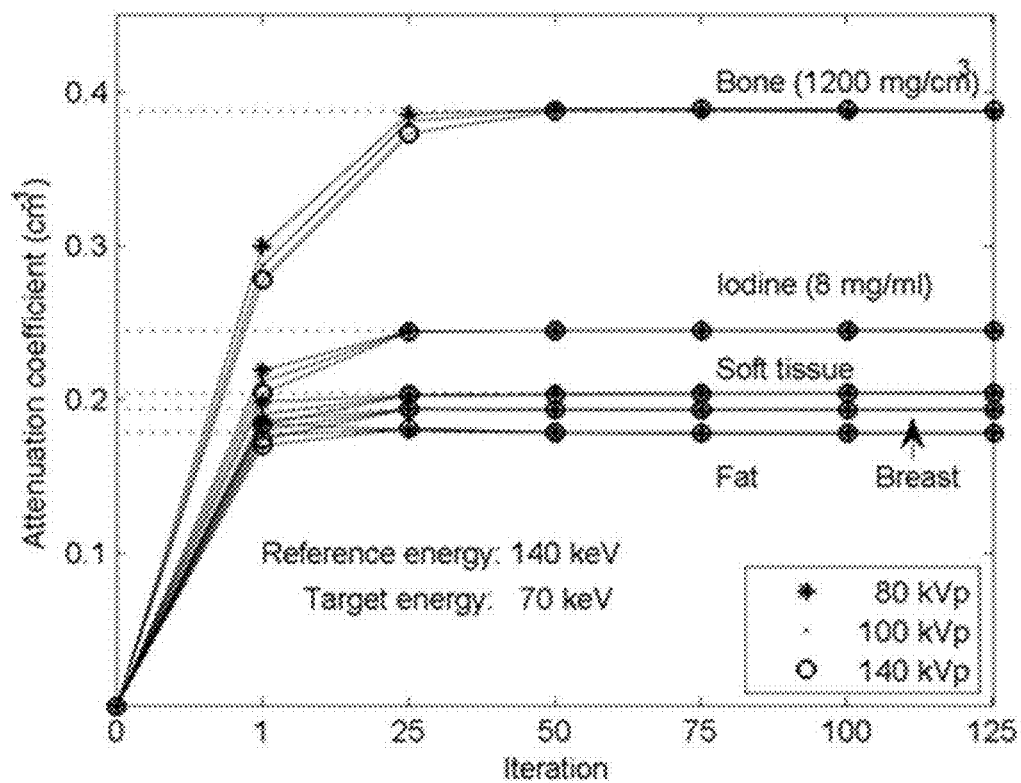

The results of the convergence test for different spectra are illustrated in FIGS. 19A-19C, which illustrate graphs showing convergence test results for different spectra (asterisk: 80 kVp; dot: 100 kVp; circle: 140 kVp) of the (a) SART algorithm, (b) pSART algorithm at reference energy $E_0=70$ keV, and (c) pSART algorithm at reference energy $E_0=140$ keV. Attenuation convergence curves are plotted for the materials in the 23 cm diameter phantom (from bottom to top: fat, breast tissue, soft tissue, 8 mg/ml iodine, and 1200 mg/ml bone) under three different x-ray spectrum (star: 80 kVp; dot: 100 kVp; circle: 140 kVp). For SART (FIG. 19A), the curves did not change after 100 iterations. However, because of nonlinear BH effect, none of the reconstructed attenuation values of bone and iodine converged to the theoretical values. The reconstructed attenuation values of fat and breast tissue were close to the theoretical values, but their relative errors (about −1.1% to −3.2%) were still significant. Soft tissue values were relatively accurate because of similar attenuation properties with water.

In FIG. 19B, the three kVp spectrum datasets were reconstructed by pSART. Similar with SART, the values did not change after 100 iterations. However, different from SART, the attenuation values reconstructed by pSART converged to the expected values associated with the target energy. Besides, the dataset of the low kVp spectrum possessed fastest convergence speed among the three datasets.

FIG. 19C depicts the attenuation convergence curves of the same spectra but at higher reference energy of 140 keV. One significant improvement was faster convergence speed for all spectrum datasets. Instead of requiring more than 100 iterations at the reference energy of 70 keV, the attenuation values reached the expected attenuation values at the 50-th iteration.

SART generally needed approximately 100 iterations to reconstruct a dataset of 1152 projections and each iteration cost about 4s. For pSART, each iteration costs about 5s, but by selecting higher reference energy, the number of iterations could be reduced to 50 leading to a shorter computational time than that of SART (Table 15). This implies remarkable reconstruction efficiency of the proposed algorithm.

TABLE 15

Comparison between SART and pSART in terms of computational time.

| | Iterations | Time/Iteration | Total Time |
|---|---|---|---|
| SART | 100 | 4 sec | 7 min |
| pSART | 50 | 5 sec | 4 min |

Figure 20:
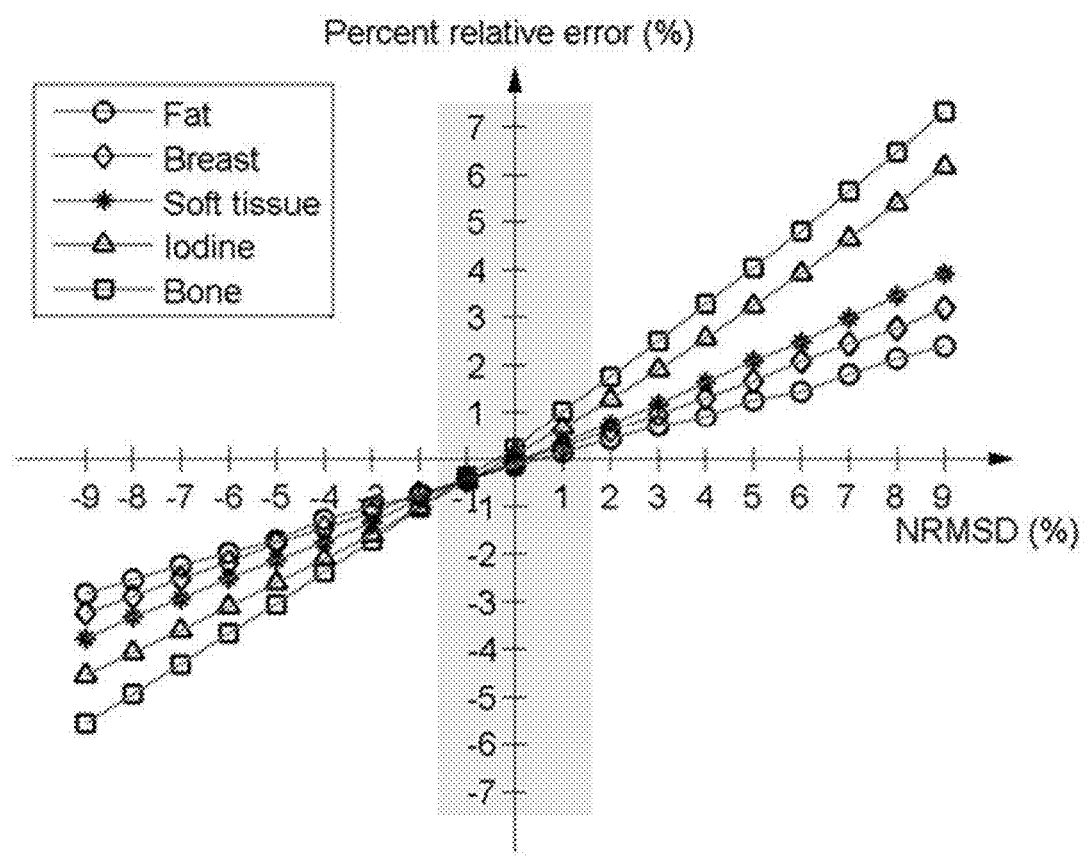
FIG. 20 illustrates a graph showing spectrum mismatch results.

The results of the spectrum mismatch test are shown in FIG. 20, which illustrates a graph showing spectrum mismatch results. Percent relative errors of different body tissues were derived based on different mismatch spectra (80 kVp), the NRMSDs of which ranged from −9% to 9%. The projection data were simulated by using the 23 cm diameter phantom. For the softened mismatch spectra (i.e., NRMSD <0%), the attenuation values for all body tissues were underestimated (i.e., relative errors <0) due to the increased photon number in the low energy range. The reverse was the case for the hardened spectra. The relative error range was increased from [−0.1%, 0.1%] to [−5.1%, 4.5%] for the spectrum with largest NRMSD of −9% and 9%. We recently proposed a robust spectrum measurement technique, which showed that an experimental accuracy of +1.6% is readily achievable. Therefore, the relative error range could be reduced down to [−0.9%, 1.5%], which was smaller than that of SART with the correct spectrum (i.e., [−1.9%, 2.1%]). If water calibration is available, the relative error range could be further reduced by subtracting the offset value associated with water. This finding shows that pSART can moderately tolerate the mismatch spectra.

Figure 21:
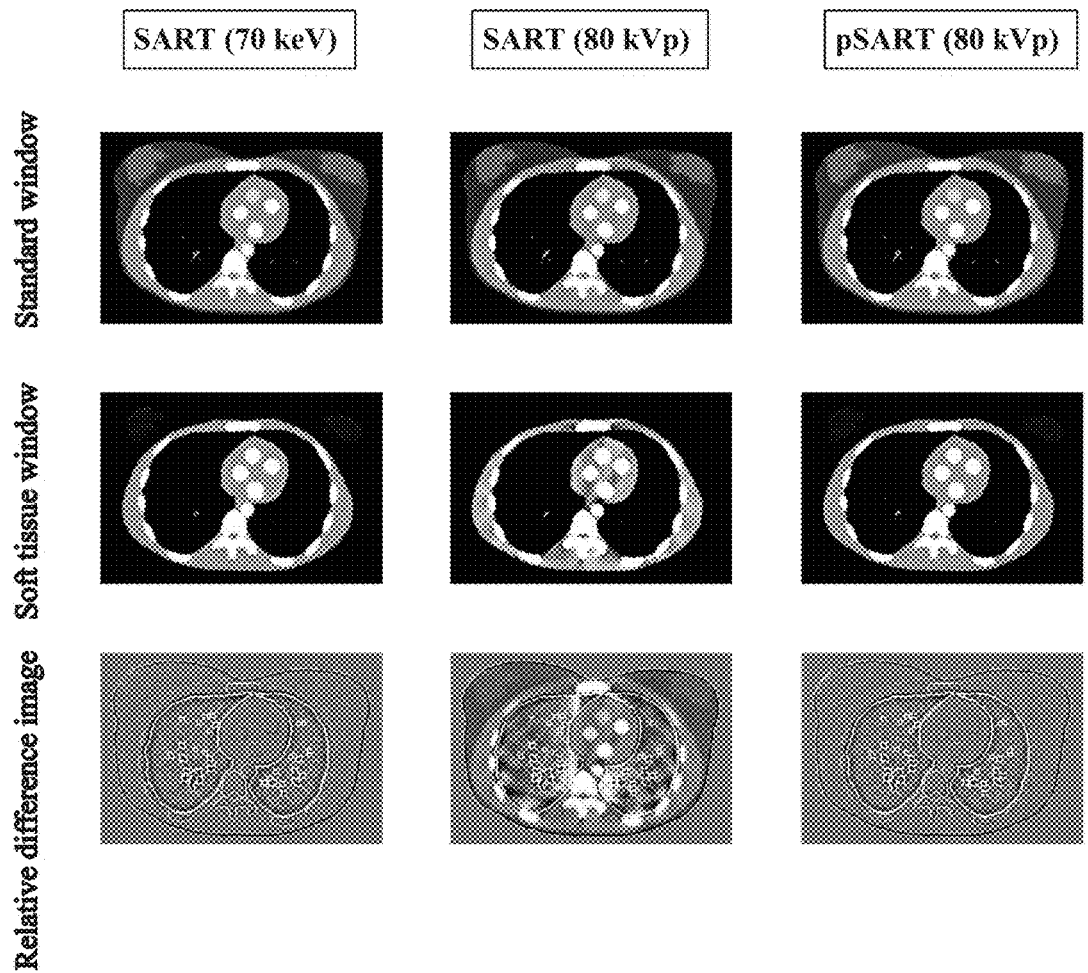
FIG. 21 illustrates images of reconstruction results of the anthropomorphic thorax phantom.

The reconstruction results of the anthropomorphic thorax phantom are shown in FIG. 21, which illustrates images of reconstruction results of the anthropomorphic thorax phantom. The images from the first column to the third column were reconstructed by the SART (70 keV), SART (80 kVp), and pSART (80 kVp), respectively. The images from the first row to the second row are shown in different windows, i.e., fat window (−25/350) and soft tissue window (50/100). The last row shows the relative difference images with window level 0%/20%. All of them were initialized with zero values and used 200 iterations. The images were 512×350 with a voxel size of 0.56×0.56 mm². The images simulated at 70 keV and reconstructed by SART are presented in the first column for reference. The images reconstructed by SART and pSART simulated with the same poly-energetic projection dataset (80 kVp) are presented in the second and third columns, respectively. To further facilitate visual comparison, the images are shown with the standard window (−25/350) in the first row and with the soft tissue window (50/100) in the second row. The relative difference between the reconstructed images and the phantom (FIG. 14) are shown in the last row with a window/level of 0%/20%. All of them were initialized with zero values and used 200 iterations to reach full convergence. The images in the first column (FIG. 20) were reconstructed by FBP (70 keV). Using a mono-energetic spectrum, no BH artifact was present. The difference image in the third row had approximately average zero values. The bright/dark boarders around the high frequency edges were due to the partial volume effect.

For the SART (80 kVp) algorithm, the BH effect resulted in dark streaking artifacts around the dense bones and also in the heart region. For example, in the soft tissue window, the dark streaks significantly changed the original uniform soft tissue on the two sides of the sternum. In the heart region, the streaking artifacts were induced by both the bones and the iodinated inserts. In addition to the visible artifacts, voxel value inaccuracies could be visually appreciated in its difference image. In the lung region, streaks due to the dense bones created non-uniformities that could be readily observed. Consistent with the results showed in the last subsection, fat and breast tended to be underestimated, and bones and iodinated inserts tended to be overestimated. The relative errors of the soft tissue were relatively small due to the water correction except for voxels between the high attenuation materials.

The images in the last column were acquired at 80 kVp and reconstructed by pSART. In comparison with SART (80 kVp), there were no apparent streak artifact, and the image appearance was almost the same with that of our reference image (SART, 70 keV). Other than the partial volume artifacts, the difference image in the last row had an average zero value, which indicates the high reconstruction accuracy of the pSART algorithm.

level was equal to −100 HU, and window width was equal to 100 HU. The images were 512×512 with a voxel size of 0.5×0.5 mm².

With SART, due to the poly-energetic spectrum, strong streak artifacts (the upper arrow in FIG. 23A) between the Teflon insert and the 8.5 mg/ml Iodine insert were visible in the reconstructed image. Ring artifacts caused by the iodine inserts (the lower arrow in FIG. 23A) also deteriorated the image quality. The quantitative results (Table 9) showed that the relative errors across the materials spread in a large range, i.e., [−2.0%, 4.1%]. The errors of the estimated concentrations of the iodine inserts could be as large as 1.9 mg/ml for the 8.5 mg/ml iodine insert (Table 10). In contrast, the image reconstructed by pSART (FIG. 23B) was free of artifacts. The errors across the materials were reduced to a small range [−0.4%, 0.3%] and the iodine concentrations were accurately determined with absolute errors less than 0.2 mg/ml.

TABLE 8

Relative errors in terms of the attenuation coefficient for different materials in the cylindrical phantom.

|  | Polyethylene | Polystyrene | Acrylic | Iodine Teflon | Iodine 2.2 mg/ml | Iodine 4.3 mg/ml | Iodine 6.4 mg/ml | Iodine 8.5 mg/ml |
| --- | --- | --- | --- | --- | --- | --- | --- | --- |
| SART | −2.0% | −1.6% | −0.7% | 2.0% | 1.4% | 2.3% | 3.2% | 4.1% |
| pSART | −0.3% | −0.2% | −0.2% | 0.3% | −0.2% | −0.2% | −0.3% | −0.4% |

Figure 22A:
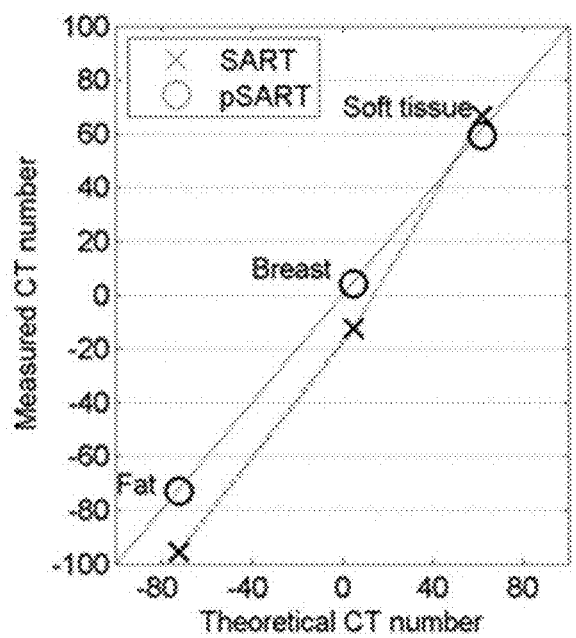
FIGS. 22A-22C are graphs showing the measured CT numbers of different materials in the images reconstructed by SART (80 kVp) and pSART (80 kVp) against the theoretical CT numbers.
Figure 22B:
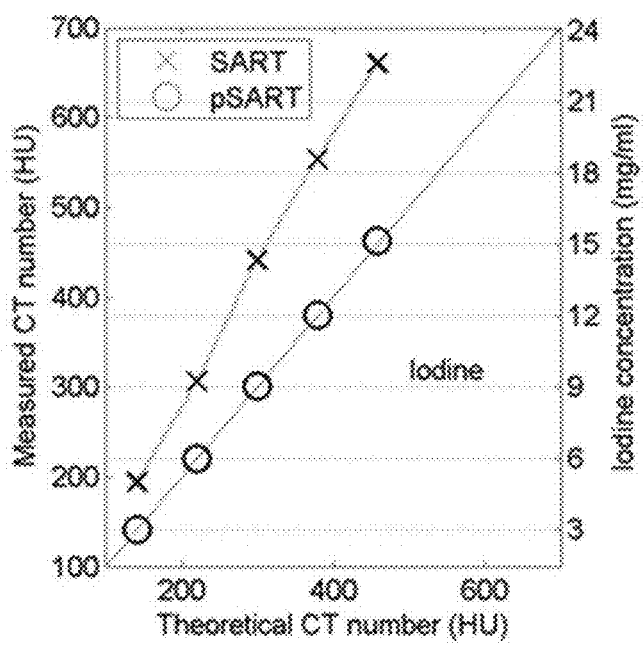
Figure 22C:
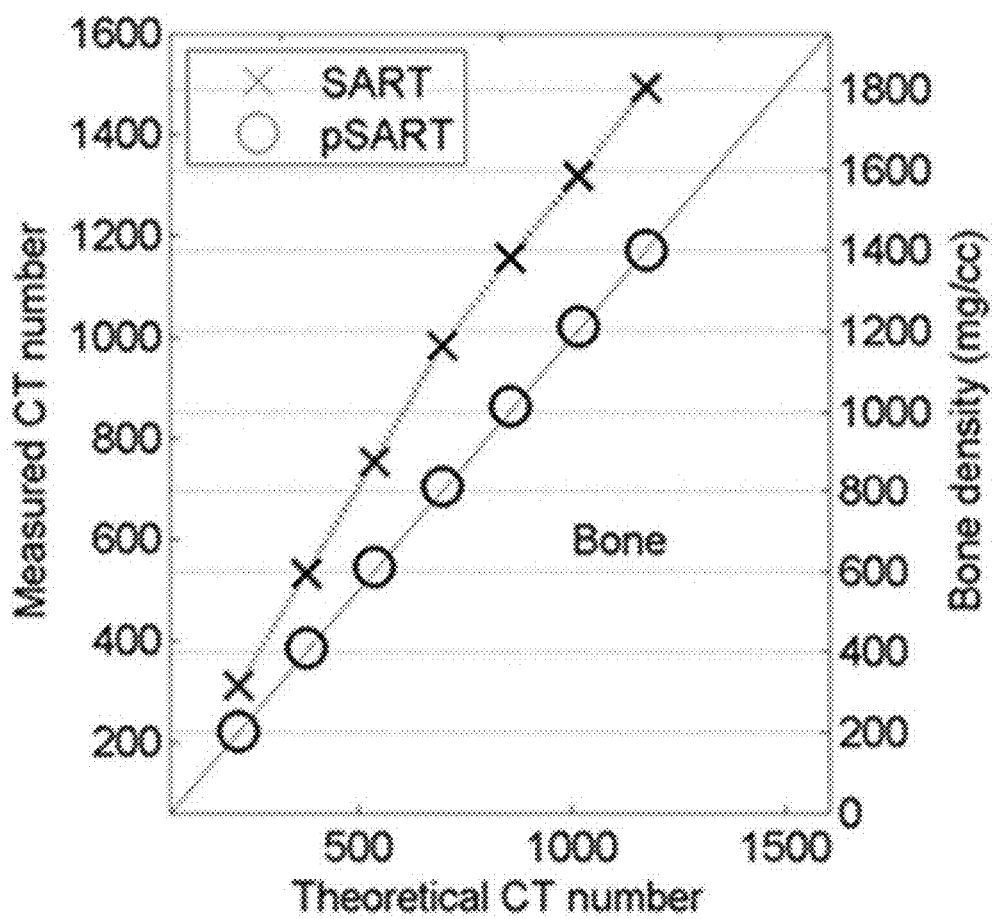

For quantitative comparison, FIGS. 22A-22C are graphs showing the measured CT numbers of different materials in the images reconstructed by SART (80 kVp) and pSART (80 kVp) against the theoretical CT numbers. Measured CT numbers of different materials from images reconstructed by SART (crosses) and pSART (circles) were plotted against the theoretical CT numbers for fat, breast, and soft tissue (see FIG. 22A), iodinated inserts of different concentrations (see FIG. 22b), and bones of different densities (see FIG. 22). In FIG. 22A, the CT numbers of fat and breast of the SART algorithm were about 20 HU lowers than the theoretical values. The soft tissue was close to the theoretical value because of the water correction, but still deviated slightly from the expected value. In contrast, the results of pSART showed good agreement with the theoretical values. In FIG. 22B, the results of various iodinated inserts were plotted, and the iodine concentration scale was added to the right-y axis for reference. For SART, Iodinated inserts were constantly overestimated, and the discrepancy could be as large as 8 mg/ml for the 15 mg/ml insert. Therefore, iodine calibration was indispensable to the SART algorithm. In comparison, as the attenuation properties of iodine had been modeled into the pSART algorithm, the measured values of pSART were in accordance with the expected values for all inserts. Thus, no iodine calibration was required. The quantitative results of various density bones were presented in FIG. 22C, and the bone density scale was added to the right-y axis for reference. For the SART, the bones were also constantly over-estimated, and the inaccuracy in the bone density estimation could be as large as 400 mg/cm³ for the 1400 mg/cm³ bone. However, the proposed algorithm accurately reconstructed the density values of all bones.

Figure 23A:
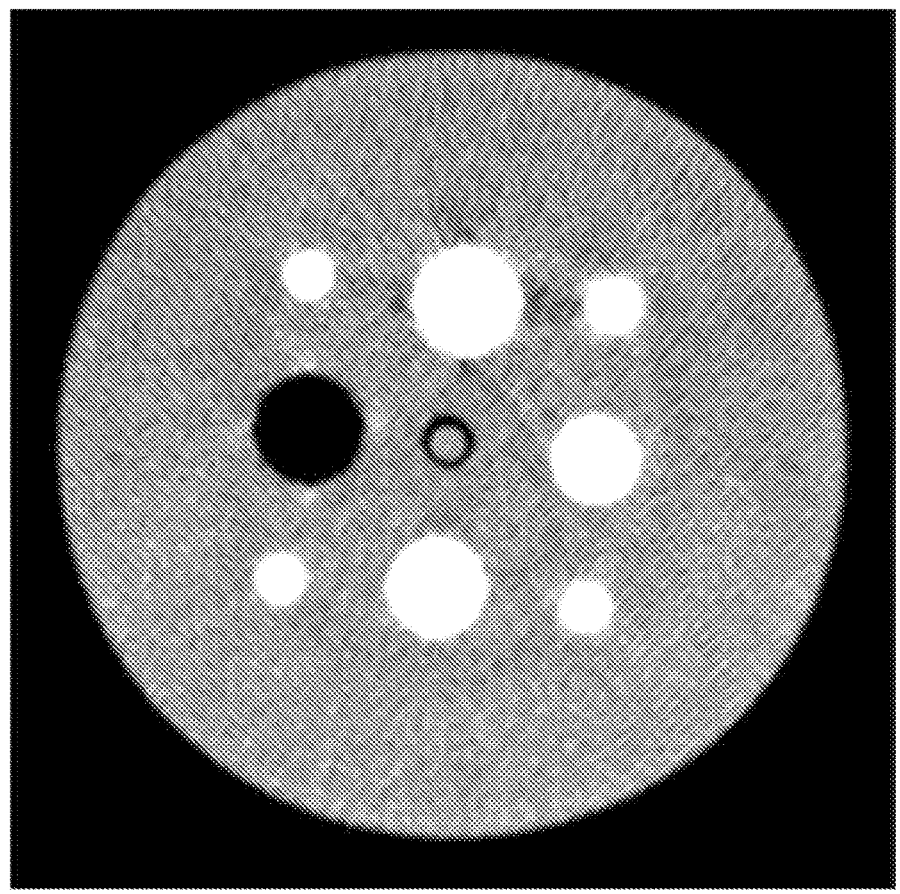
FIGS. 23A and 23B are images reconstructed by water-corrected SART.
Figure 23B:
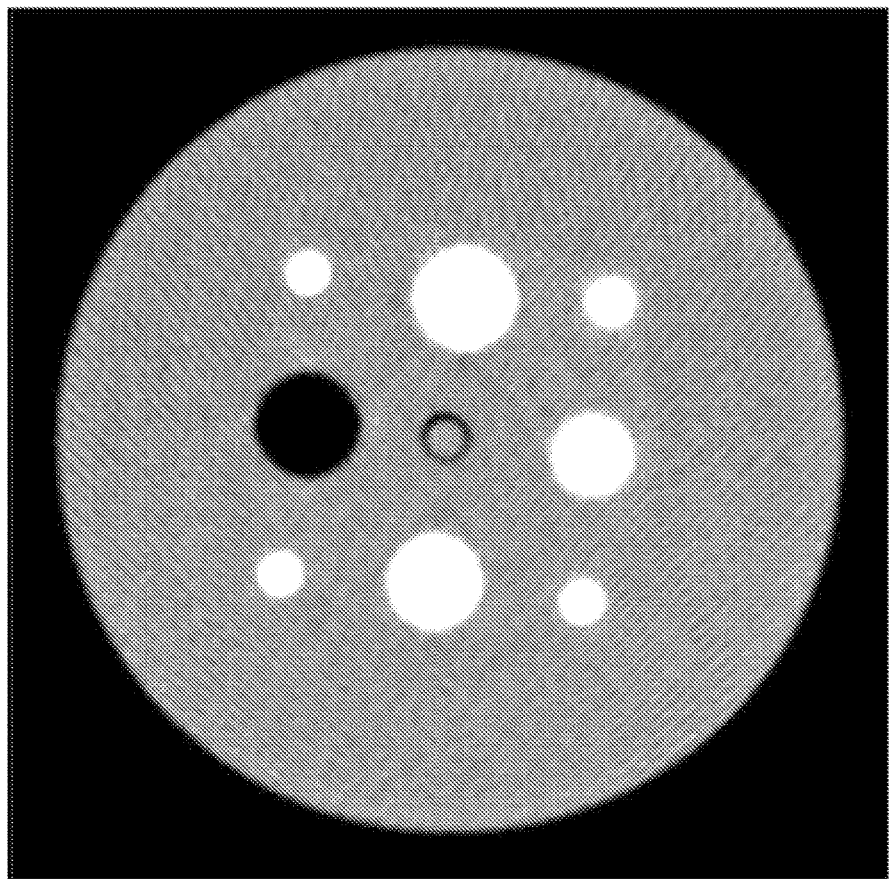

Reconstruction results of the Mercury phantom using a clinical CT scanner are shown in FIGS. 23A and 23B, which are images reconstructed by water-corrected SART (see FIG. 23A) and pSART (see FIG. 23B) from the same projection dataset, which was acquired with the 22 cm diameter Mercury phantom and 100 kVp spectrum. Window

TABLE 9

Iodine concentrations evaluated by SART and pSART.

|  | Iodine 2.2 mg/ml | Iodine 4.3 mg/ml | Iodine 6.4 mg/ml | Iodine 8.5 mg/ml |
| --- | --- | --- | --- | --- |
| SART | 2.8 | 5.3 | 7.8 | 10.4 |
| pSART | 2.1 | 4.2 | 6.2 | 8.3 |

An efficient poly-energetic SART reconstruction algorithm (pSART) was developed and is described herein. A cylindrical phantom was used to investigate the reconstruction characteristics of the proposed algorithm. The simulation results indicated that beam hardening artifacts were completely removed, and all materials converged to the expected attenuation coefficients with absolute relative errors less than 0.1% for different phantom sizes (16, 23, 30, 37 cm) and spectra (80, 100, 120, and 140 kVp). The base material transition test indicated the importance of incorporating the correct attenuation information for the materials presented in the scanned objects. The convergence test results indicated that the reconstructions with low kVp data or high reference energies converged faster and required less number of iterations. Finally, the spectrum mismatch test showed that the range of relative errors across materials only increased from [−0.1%, 0.1%] (derived with the correct spectrum) to [−0.9%, 1.5%] for the spectra with NRMSDs of ±1.6% expected from experimental measurements. This error range was smaller than that of SART with the correct spectrum (i.e., [−1.9%, 2.1%]), which indicated that pSART could moderately tolerate spectral inaccuracies associated with experimental limits.

A realistic anthropomorphic phantom with detail anatomical structures was used to quantitatively investigate the reconstruction ability of pSART in comparison with SART. The reconstruction results showed that pSART could completely eliminate the BH artifacts and the CT numbers could be accurately reconstructed for all body tissues, bones with different densities, and iodinated inserts with different concentrations. The experiment performed on a clinical CT scanner showed that, compared with SART, pSART was able to reconstruct an artifact-free image. The quantitative results further showed that the absolute relative errors of the voxel values estimated by pSART were less than 0.4%, which enables one to accurately determine the iodine concentrations with absolute errors less than 0.2 mg/ml.

In accordance with the present disclosure, diverse base materials, including fat, breast, soft tissue, bone, and iodine, may be modeled into the reconstruction process, and the subtle differences of bones of different densities and iodine voxels of different concentrations are accurately modeled by the presently disclosed algorithm. Thus, beam hardening artifacts and also significantly improve the CT number accuracy. Further, the present subject matter does not require advanced segmentation techniques or registration techniques to precisely segment the images into regions of soft tissue, bone, and iodine. There is only a need to coarsely segment the images into two types of regions, i.e., non-bone regions and non-iodine regions, which reduces the computational complexity and is easily achieved by the current anatomical based segmentation methods. As no registration is involved, our method does not suffer from patient motion artifacts. Further, when using low kVp spectra and high reference energies, the reconstruction efficiency of the poly-energetic algorithms (e.g., pSART) in terms of convergence speed surpasses that of their corresponding mono-energetic algorithms (e.g., SART).

In previous literature, if K-edge materials are absent, the material in each voxel can be decomposed into two bases (i.e., photoelectric component and Compton component) or two distinct materials (e.g., water and bone). This decomposition approach can quantitatively reconstruct an object of unknown composition. However, as it doubles the solution space, the object has to be scanned by a dual energy scanner to obtain more information, thus increases the cost and the complexity of the scanning technology. In comparison, pSART assumes that the scanned object is composed of known base materials. The well-defined attenuation properties of the base materials are incorporated into the reconstruction process as prior information. After segmenting the images into non-iodine region and non-bone region, the attenuation property of each voxel can be uniquely indexed by its attenuation at a reference energy ($E_O$). As such, the size of the solution space in this work is the same as that of the SART algorithm. Overall, pSART can be applied on a CT to reconstruct artifact-free image.

In accordance with embodiments, a segmentation-free, poly-energetic, dynamic perfusion imaging algorithms (pDP) are provided for providing improved perfusion imaging. Dynamic perfusion imaging can provide the morphologic details of the scanned organs as well as the dynamic information of blood perfusion. However, due to the poly-energetic property of the x-ray spectra, beam hardening effect results in undesirable artifacts and inaccurate CT values. The imaging algorithms provide herein can address such difficulties.

Dynamic perfusion is typically composed of two phases, i.e., a pre-contrast phase and a post-contrast phase. In the pre-contrast phase, the attenuation properties of diverse base materials (e.g., in a thorax perfusion exam, base materials can include lung, fat, breast, soft tissue, bone, and metal implants) can be incorporated to reconstruct artifact-free pre-contrast images. If patient motions are negligible or can be corrected by registration, the pre-contrast images can then be employed as a priori information to derive linearized iodine projections from the post-contrast images. With the linearized iodine projections, iodine perfusion maps can be reconstructed directly without the influence of various influential factors, such as iodine location, patient size, x-ray spectrum, and background tissue type. A series of simulations were conducted on a dynamic iodine calibration phantom and a dynamic anthropomorphic thorax phantom to validate the proposed algorithm.

In dynamic CT perfusion imaging, iodinated contrast agent is administrated to a patient through intravenous injection as a way to raise the radiopacity and to enhance the visibility of vascular structures and organs. By recording the change of the CT numbers of the pre-selected ROIs during the passage of the iodine bolus, time-attenuation curves (TACs) and time-concentration curves (TCCs) can be obtained, from which blood flow (BF), blood volume (BV), and mean transit time (MTT) can be derived to diagnose different diseases. For example, cardiac myocardial perfusion imaging can help detect coronary artery disease (e.g., infarcted or ischemic myocardium), assess left and right ventricular function, and evaluate for structural heart disease. Lung perfusion CT can help identify pulmonary emboli and differentiate between benign and malignant nodules. Researches in breast perfusion imaging shows that breast cancers can be distinguished from normal mammary glands based on the perfusion values.

Beam hardening effect is one of the major influential factors that limit the quality and accuracy of the dynamic perfusion imaging. When x-rays pass through materials, low energy photons are preferentially absorbed, which increases the mean energy of the x-rays. This phenomenon leads to various artifacts in reconstructed images, such as cupping and streaking. In perfusion imaging, the K-edge contrast enhancement agents (such as iodine) can dramatically absorb low-energy photons and cause artifacts stronger than that in non-contrasted CT. For example, in myocardial perfusion imaging, BH artifacts can result in underestimated attenuation of affected tissue that may be misinterpreted as a perfusion defect. The HU deviation due to BH can be as large as 40 HU, which makes the quantitative evaluation of iodine perfusion challenging.

Currently, the CT perfusion imaging algorithm widely used in clinical practice is based on water-corrected FBP algorithms. This approach requires pre-calibrated iodine concentration curves across different spectra and phantom sizes, so that the errors of measured TACs or TCCs can be reduced. This approach takes the advantage of FBP's fast speed, but is susceptible to streak artifacts induced by high attenuation materials, such as bone, iodine, and metal.

Some efforts have been made to account for the attenuation properties of bone and iodine, but with limited success. For example, an image-based beam hardening correction algorithm has been proposed to incorporate the attenuation properties of water, bone and iodine in terms of effective density. However, a pre-requisite of this method is to accurately segment these three base materials into distinct regions. Another developed a method to distinguish the three regions by measuring the voxel dynamics, but they used a series of threshold-based segmentation techniques, and the voxels containing low concentration or low dynamic iodinated contrast agent could be potentially mis-interpreted as soft tissue or bone minerals. Besides, both of the two methods are limited to myocardial perfusion exam, as they only modeled the attenuation properties of blood-iodine mixture. Errors may arise in other perfusion exams, such as lung or breast perfusion exams.

The disclosed poly-energetic dynamic perfusion imaging algorithm (pDP) does not require segmentation. Assuming minimal or correctable patient motions, pre-contrast images are used as a priori information to derive linearized iodinated projections from post-contrast projections. With the linearized iodinated projections, artifact-free iodine maps can be reconstructed directly. As diverse base materials (e.g., lung, fat, breast, soft tissue, bone, metal implant, and iodine) are incorporated, pDP enables quantitative iodine map reconstruction independent of various influential factors such as iodine location, patient size, spectrum, and background tissue type.

Figure 24:
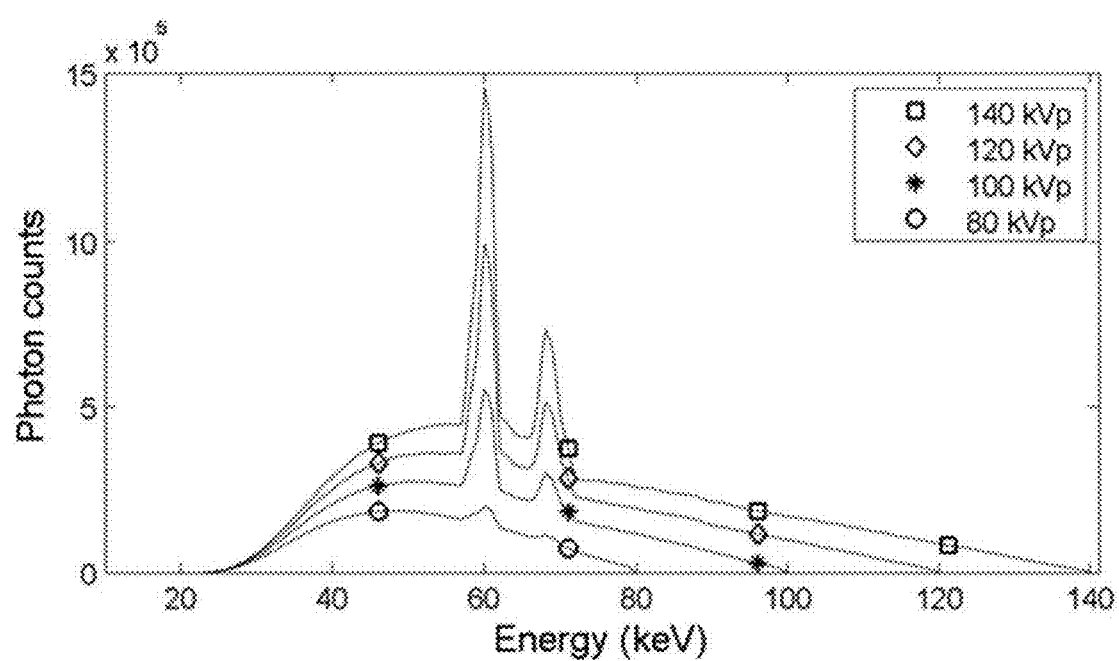
FIG. 24 illustrates a plot of example spectra utilized in accordance with embodiments of the present disclosure.

Symbols and definitions used through this paper are summarized in Table 11. The spectra used in this work are plotted in FIG. 24, which illustrates a plot of example spectra utilized in accordance with embodiments of the present disclosure.

Figure 25:
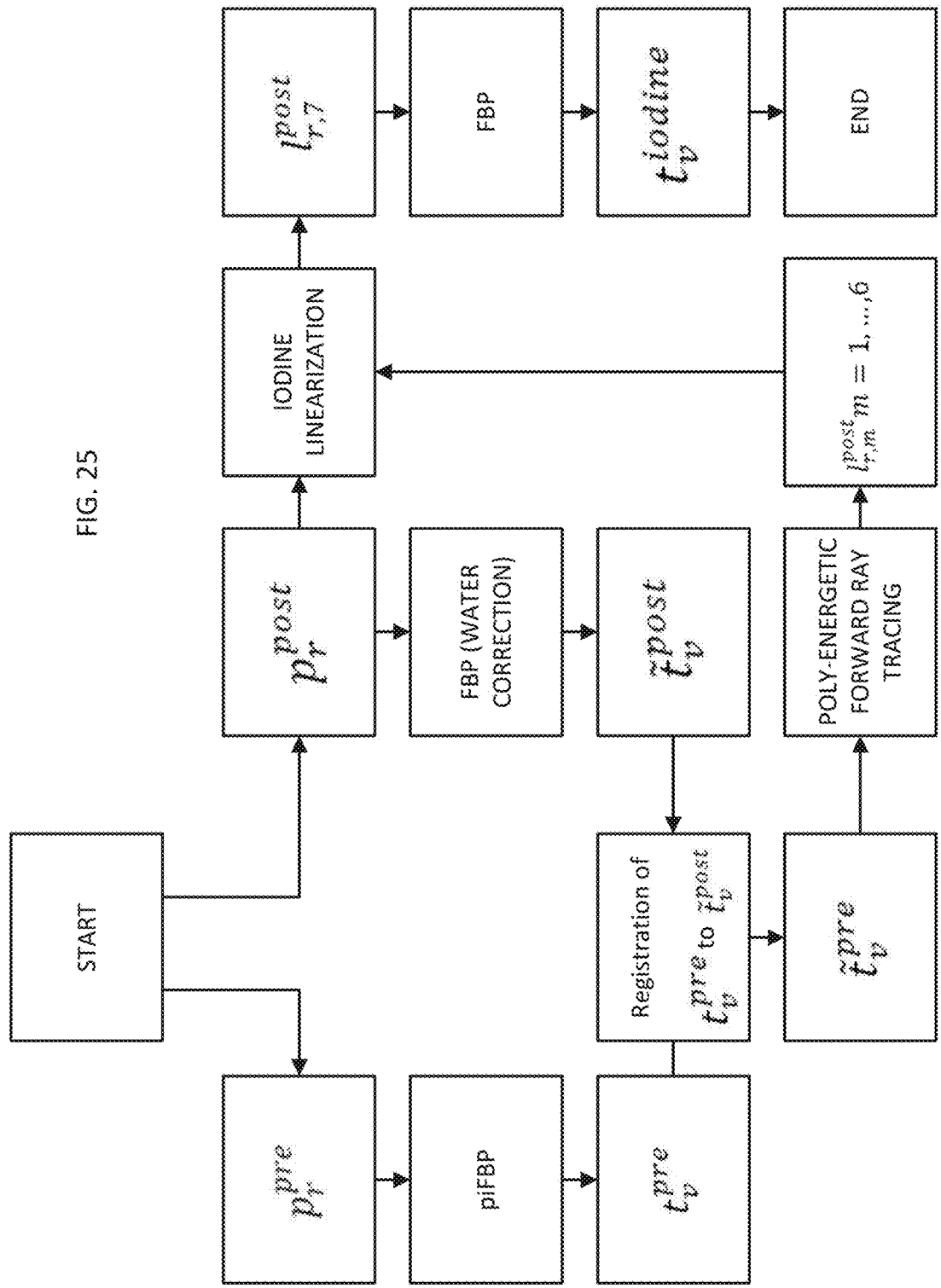
FIG. 25 illustrates a flow chart of an pDP algorithm in accordance with embodiments of the present disclosure.

FIG. 25 illustrates a flow chart of a pDP algorithm in accordance with embodiments of the present disclosure. Here, $r=1, \ldots, N_R$ is the r-th ray from the x-ray source to the detector element, $v=1, \ldots, N_V$ is the v-th voxel of the target volume, and $N_R$ and $N_V$ are the total numbers of the x-ray paths and target voxels, respectively. With the pre-contrast measurements $p_r^{pre}$, the pre-contrast images $t_v^{pre}$ are first reconstructed using poly-energetic iterative FBP (piFBP). Note that the derivation of the iodine map reconstruction described herein relies on the theory, symbols, and equations, previously detailed for piFBP. A summary of these materials is provided herein.

With the post-contrast measurements $p_r^{post}$ intermediate post-contrast images $\tilde{t}_v^{post}$ are reconstructed as references to register pre-contrast images $t_v^{pre}$ as a way to offset patient motions and to obtain motion-free pre-contrast images $\tilde{t}_v^{pre}$, with which the accumulated effective lengths $l_{r,m}^{post}$ of all body tissues are computed based on the acquisition parameters of $p_r^{post}$ and are used as a priori information to derive the linearized iodine projections ($l_{r,7}^{post}$). Here, $m=1, \ldots, N_M$ is the base material index, $N_M$ is the total number of the base materials, and the material index of iodine is $m=7$. In this way, the linearized iodine projections $l_{r,7}^{post}$ can be reconstructed into artifact-free iodine maps ($t_v^{iodine}$) by a standard FBP algorithm. Disclosed herein in detail is the post-contrast iodine map reconstruction method.

TABLE 101

Symbols and definitions.

| Symbols | Definitions |
|---|---|
| $\mathcal{B}$ | Filtered back projection (FBP) operator |
| $\mathcal{F}(\mathcal{F}_w)$ | Logarithmic poly-energetic forward projection operator (with water correction) |
| $I_e$ | X-ray photon intensity at the e-th energy bin |
| $I(\varepsilon)$ | X-ray photon intensity at energy level $\varepsilon$ |
| N | Total number of the voxels in the measured ROI |
| $N_E$ | Total number of the spectrum energy bins |
| $N_M$ | Total number of the base materials |
| $N_R$ | Total number of the x-ray paths from x-ray source to detector modules |
| $N_V$ | Total number of the voxels of the volume |
| S | Smoothing operator |
| $Y_{rs}$ | CT Measurement through the r-th x-ray with the s-th incident spectrum |
| $a_{vr}$ | Contribution of the v-th voxel to the r-th ray |
| e | Index for spectrum energy bins |
| $l_{mr}^{pre}/$ $l_{mr}^{post}$ | Accumulated effective length of the m-th material along the r-th ray in the pre-/post-contrast phase |
| m | Index for the base materials |

TABLE 101-continued

Symbols and definitions.

| Symbols | Definitions |
|---|---|
| $\bar{p}^{pre}$ ($\bar{p}_w^{pre}$) | Column vector of estimated logarithmic poly-energetic measurements (after water correction) in the pre-contrast phase |
| $p_r^{pre}/$ $p_r^{post}$ | Logarithmic measurement along the r-th ray in the pre-/post-contrast phase |
| $\bar{p}_r^{pre}/$ $\bar{p}_r^{post}$ | Estimated logarithmic measurement along the r-th ray in the pre-/post-contrast phase |
| r | Index for the x-ray paths |
| $t^{pre}$ | Column vector of voxels of the target volume in terms of the attenuation coefficient at $\varepsilon$ in the pre-contrast phase |
| $t_v^{pre}/$ $t_v^{post}$ | Attenuation coefficient of the v-th voxel at reference energy $E_0$ in the pre-/post-contrast phase |
| $t_v^{iodine}$ | Iodine map in the post-contrast phase |
| $\tilde{t}_v^{pre}$ | Intermediate pre-contrast image obtained by registering $t_v^{pre}$ to $t_v^{post}$ |
| $\tilde{t}_v^{post}$ | Intermediate post-contrast image reconstructed from post-contrast projections as motion correction reference |
| $t(\vec{x})$ | Attenuation coefficient at location $\vec{x}$ at reference energy $E_0$ |
| v | Index for the voxels |
| $\varepsilon$ | Energy level within the spectrum range |
| $\varepsilon_0$ | Reference energy, at which the mono-energetic image will be reconstructed |
| $\mu(\vec{x}, \varepsilon)$ | Attenuation coefficient at location $\vec{x}$ at reference energy $\varepsilon$ |
| $\mu_{me}$ | Attenuation coefficient of the m-th base material at the e-th energy bin |
| $\mu_m(\varepsilon)$ | Attenuation coefficient of the m-th base material at energy $\varepsilon$ |
| $\rho_m$ | Density of the m-th base material |
| $\rho_v$ | Density of the v-th voxel |

The forward projection model for the poly-energetic x-ray beam is given by $$\bar{p}_r^{pre} = -\ln(\int I(\varepsilon) \exp[-\int_{L_r} \mu(\vec{x}, \varepsilon) dl] d\varepsilon), \quad (37)$$

where $\bar{p}_r^{pre}$ ($r=1, \ldots, N_R$) is the estimated logarithmic measurement along the r-th ray line $L_r$ in the pre-contrast phase, $I(\varepsilon)$ is the spectrum (normalized to unit area), and $\mu(r,\varepsilon)$ is the unknown spatial- and energetic-related attenuation map of the object. In order to reduce the free degrees of the attenuation map $\mu(r,\varepsilon)$ and to quickly evaluate this nonlinear double integral, we propose the following adaptive base material decomposition method.

Figure 26A:
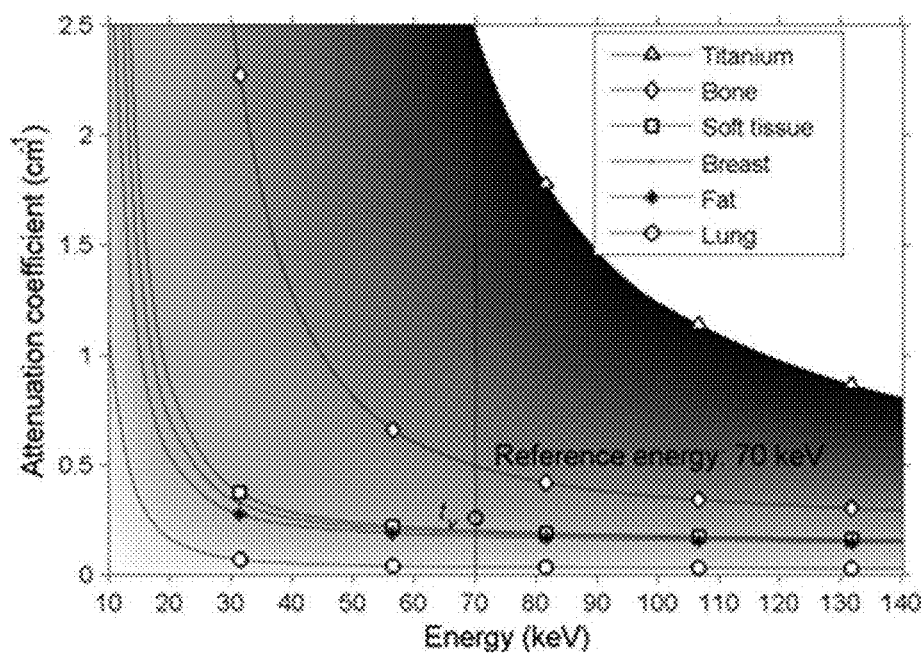
FIGS. 26A and 26B are graphs showing plots of attenuation coefficient curves of base materials in a pre-contrast phase.
Figure 26B:
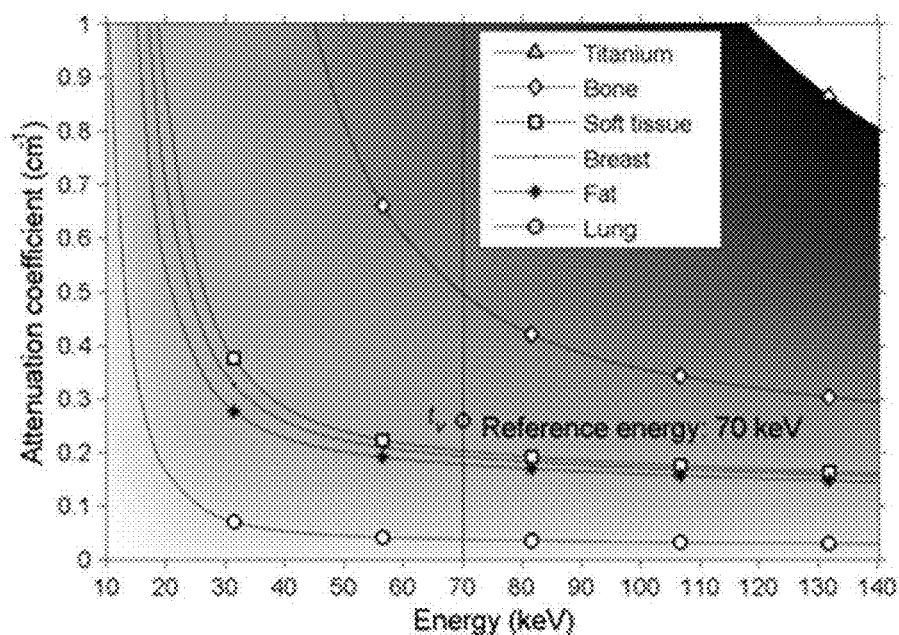

It is assumed herein that the object is comprised of $N_M$ known base materials, and the mixture in each voxel can be decomposed to iodine and two other base materials. The base material set can be chosen based on the CT exams. For example, in thorax perfusion CT exam, the base material set can include air (m=0), lung (m=1), fat (m=2), breast (m=3), soft tissue (m=4), bone (m=5, 1920 mg/cc water-calcium solution), metal implant (m=6, e.g., titanium), and iodine (m=7). The attenuation coefficient curves of the base materials in the pre-contrast phase are plotted in FIGS. 26A and 26B. Particularly, the figures show attenuation coefficient curves of the base materials for chest CT exam. FIG. 26A shows a plot with large attenuation coefficient range [0.0, 2.5] to facilitate the appreciation of the relative relationship between the high attenuation curves and the low attenuation curves. FIG. 26B shows a plot with small attenuation coefficient range [0.0, 1.0] to facilitate the appreciation of the relative relationship of the low attenuation curves. The gray gradient indicates the interpolated attenuation curves along the 70 keV reference energy line.

Body tissues like lung, fat and breast can be approximated with water, but because of the differences in attenuation property, their CT numbers can deviate significantly from the real values. In contrast, the base material set disclosed herein contains a wide range of base materials, so that gradation of attenuation coefficients for various tissue types can be broadly sampled. As a common biocompatible metal implant material, titanium is also selected as a base material in this work to test the metal artifact reduction ability of the proposed algorithm.

For the convenience of incorporating the base material set into the forward projection process, we define each indexed voxel of $t_v^{pre}$ ($v=1, \ldots, N_V$) as the attenuation coefficient at a reference mono-energetic energy of $\varepsilon_0$ (e.g. $\varepsilon_0$=70 keV). Based on the value of $t_v^{pre}$, each voxel of mixture is adaptively decomposed to two adjacent base materials. Note that in the pre-contrast phase, iodine does not exist, so the base material indices are only limited to m=0, ..., 6. For example, if $t_v^{pre}$ (the circle in FIGS. 27A and 27B) is within the bone interval, i.e., $[\mu_4(\varepsilon_0), \mu_5(\varepsilon_0))$, where $\mu_m(\varepsilon_0)$ is the attenuation coefficient of the m-th base material at the reference energy $\varepsilon_0$, the attenuation coefficient curve for the v-th voxel can be estimated as $$\mu(t_v^{pre}, \varepsilon) = \frac{\mu_5(\varepsilon_0) - t_v^{pre}}{\mu_5(\varepsilon_0) - \mu_4(\varepsilon_0)}\mu_4(\varepsilon) + \frac{t_v^{pre} - \mu_4(\varepsilon_0)}{\mu_5(\varepsilon_0) - \mu_4(\varepsilon_0)}\mu_5(\varepsilon). \tag{38}$$

As the base material bone (1920 mg/ml) used here is the mixture of water and calcium element, the bone density in the v-th voxel can be computed as $$\rho_v = \frac{t_v^{pre} - \mu_4(\varepsilon_0)}{\mu_5(\varepsilon_0) - \mu_4(\varepsilon_0)} \times 1920 \text{ mg/cc}. \tag{39}$$

The above adaptive decomposition strategy can be applied to the other intervals (i.e., $[\mu_i(\varepsilon_0), \varepsilon_{i+1}(\varepsilon_0))$, i=1,2,3) to account for the gradual changes of the attenuation coefficient curves. Therefore, a general decomposition equation for the v-th voxel can be expressed as $$\mu(t_v, \varepsilon) = \sum_{m=0, \ldots, 5} \chi_{[\mu_m, \mu_{m+1}]}(t_v^{pre}) \left[ \frac{\mu_{m+1}(\varepsilon_0) - t_v^{pre}}{\mu_{m+1}(\varepsilon_0) - \mu_m(\varepsilon_0)}\mu_m(\varepsilon) + \frac{t_v^{pre} - \mu_m(\varepsilon_0)}{\mu_{m+1}(\varepsilon_0) - \mu_m(\varepsilon_0)}\mu_{m+1}(\varepsilon) \right], \tag{40}$$

where the step function $\chi_{[a,b)}$ is defined as $$\chi_{[a,b)}(t) = \begin{cases} 1 & t \in [a, b) \\ 0 & t \notin [a, b) \end{cases}. \tag{41}$$

For easy observation, the interpolated attenuation curves along the 70 keV reference energy line with Equation 40 is plotted in FIGS. 26A and 26B with a gray gradient color. To reduce the computational time, the base material interval indices and the corresponding effective lengths for every voxel can be calculated and stored in matrices before each iteration, with which the accumulated effective lengths of all base materials can be computed through one forward ray tracing as $$\int_{L_r} \mu(t(\vec{x}), \varepsilon) dl \approx \sum_{v=1, \ldots, N_V} a_{rv} \mu(t_v^{pre}, \varepsilon) = \sum_{m=0, \ldots, 6} l_{rm}^{pre} \mu_m(\varepsilon), \tag{42}$$

where $a_{rv}$ denotes the elements of the system matrix, and $l_{rm}^{pre}$ denotes the accumulated effective length of the m-th material for the r-th ray, $$l_{rm}^{pre} = \sum_{v=1, \ldots, N_V} a_{rv} \chi_{[\mu_m, \mu_{m+1}]}(t_v^{pre}) \times \tag{43}$$

$$\begin{cases} \frac{\mu_{m+1}(\varepsilon_0) - t_v^{pre}}{\mu_{m+1}(\varepsilon_0) - \mu_m(\varepsilon_0)} & m = 0 \\ \frac{\mu_{m+1}(\varepsilon_0) - t_v^{pre}}{\mu_{m+1}(\varepsilon_0) - \mu_m(\varepsilon_0)} + \frac{t_v^{pre} - \mu_{m-1}(\varepsilon_0)}{u_m(\varepsilon_0) - \mu_{m-1}(\varepsilon_0)} & m = 1, \ldots, 5, \\ \frac{t_v^{pre} - \mu_{m-1}(\varepsilon_0)}{u_m(\varepsilon_0) - \mu_{m-1}(\varepsilon_0)} & m = 6 \end{cases}$$

With the accumulated effective length $l_{rm}^{pre}$, the poly-energetic forward projection equation (Eq. 37) can be easily calculated as $$\bar{p}_r^{pre} = -\ln\left( \int I(\varepsilon) \exp\left[ -\int_{L_r} \mu(t(\vec{x}), \varepsilon) dl \right] d\varepsilon \right) \tag{44}$$

$$\approx -\ln\left( \sum_{e=1, \ldots, N_E} I_e \exp\left[ -\sum_{m=0, \ldots, 6} l_{rm}^{pre} \mu_{me} \right] \Delta e \right),$$

where $I_e$ denotes the e-th energy bin (e=1, ..., $N_E$) of the x-ray spectrum and $N_E$ is the total number of the discrete energy bins. For simplicity, Equation 44 can be expressed in a vector notation as $$\bar{p}^{pre} = \mathcal{F} t^{pre}, \tag{45}$$

where $\bar{p}^{pre}$ is the column vector of the estimated logarithmic poly-energetic detector values, $t^{pre}$ is the column vector of the target volume in terms of the attenuation coefficient at reference energy $\varepsilon_0$, and F is the logarithmic poly-energetic forward projection operator.

With the poly-energetic forward projection operation described above, the poly-energetic iterative FBP algorithm with a smoothing operator (piFBP) can be written as $$\begin{cases} t^{pre(0)} = \mathcal{B} p_w^{pre} \\ t^{pre(k+1)} = t^{pre(k)} + c\mathcal{S}\mathcal{B}(p^{pre} - \mathcal{F} t^{pre(k)}) \end{cases}, \tag{46}$$

where B is the filtered back projection (FBP) operator, $p_w^{pre}$ is the column vector of the water corrected logarithmic poly-energetic measurements, k is the iteration index (k≥0), and c is the relaxation parameter. In this example, the relaxation parameter c was set to one. As BH artifacts are mainly low frequency signals, a smoothing operator S was added to suppress the noise of the correction volume and to improve the convergence stability. In this work, a smoothing kernel of 5×5 pixels Gaussian low pass filter (mean=0 and sigma=1.05) was favored to provide sufficient noise suppression.

The enhancement of the post-contrast projections with respect to the pre-contrast ones is mainly due to the introduced iodine contrast agent. As the attenuation property of the iodine solvent is similar to that of soft tissue or blood, it can be assumed that the increase of the voxel values is only caused by iodine element, i.e., $$t_v^{post} = \tilde{t}_v^{pre} + t_v^{iodine}, \quad (47)$$

where $\tilde{t}_v^{pre}$, $t_v^{iodine}$, and $t_v^{post}$ are the v-th voxel values of the motion corrected pre-contrast images, the iodine maps, and the post-contrast images, respectively. With Equations 40 and 47, the energy-dependent attenuation coefficient for the v-th voxel of the post-contrast images can be expressed as $$\mu(t_v^{post}, \varepsilon) = \sum_{m=0,\ldots,5} \chi_{[\mu_m, \mu_{m+1}]}(t_v) \left[ \frac{\mu_{m+1}(\varepsilon_0) - \tilde{t}_v^{pre}}{\mu_{m+1}(\varepsilon_0) - \mu_m(\varepsilon_0)} \mu_m(\varepsilon) + \frac{\tilde{t}_v^{pre} - \mu_m(\varepsilon_0)}{\mu_{m+1}(\varepsilon_0) - \mu_m(\varepsilon_0)} \mu_{m+1}(\varepsilon) \right] + \frac{t_v^{iodine}}{\mu_7(\varepsilon_0)} \mu_7(\varepsilon). \quad (48)$$

With the above equation, the linear integral along the r-th ray can be approximated by the accumulated effective lengths $(l_{rm}^{post}, r=1, \ldots, N_R)$ of the base materials $(m=0, \ldots, 7)$ as $$\int_{L_r} \mu(t(\vec{x}), \varepsilon) dl \approx \sum_{v=1,\ldots,7} a_{rv} \mu(t_v^{post}, \varepsilon) = \sum_{m=1,\ldots,6} l_{rm}^{post} \mu_m(\varepsilon) + l_{r,7}^{post} \mu_7(\varepsilon). \quad (49)$$

As $l_{rm}^{post}$ (m=1, . . . ,6) can be calculated with $\tilde{t}_v^{pre}$ (Eq. 43) based on the post-scan acquisition parameters, the proposed method does not require the post-contrast projections to be geometrically identical to the pre-contrast projections. The effective length of iodine $(l_{r,7}^{post})$ is defined as $$l_{r,7}^{post} = \sum_{v=1,\ldots,N_V} a_{rv} \times \frac{t_v^{iodine}}{\mu_7(\varepsilon_0)}. \quad (50)$$

With $l_{rm}^{post}$ (m=1, . . . ,6) and $p_r^{post}$ the accumulated lengths of iodine $(l_{r,7}^{post})$ can be numerically computed by solving the following nonlinear equations using bisection method $$p_r^{post} = -\ln\left( \int I(\varepsilon) \exp\left[ -\int_{L_r} \mu(t^{post}(\vec{x}), \varepsilon) dl \right] d\varepsilon \right) \quad (51)$$

$$\approx -\ln\left( \sum_{e=1,\ldots,N_E} I_e \exp\left[ -\sum_{m=1,\ldots,6} l_{rm}^{post} \mu_m(\varepsilon) - l_{r,7}^{post} \mu_7(\varepsilon) \right] \Delta \varepsilon \right).$$

To suppress noise, a projection space denoising operation can be applied to $l_{r,7}^{post}$ by using a 5×5 pixels Gaussian low pass filter (mean=0, sigma=0.8). As $l_{r,7}^{post}$ is linearly related to $t_v^{iodine}$ (Eq. 14), standard FBP algorithm can be used directly to reconstruct the iodine map. The iodine concentration of the v-th voxel can be further computed as $$c_v = \frac{t_v^{iodine}}{\mu_7(\varepsilon_0)} \times 4933 \text{ mg/cm}^3, \quad (52)$$

where 4933 mg/cc is the density of the iodine element. With $\tilde{t}_v^{pre}$ and $t_v^{iodine}$, synthesized post-contrast images can then be computed by Equation 47. As the attenuation curve of iodine is incorporated, the BH effect due to iodine can be effectively eliminated.

Note that the previous algorithms are limited to myocardial perfusion, as they assume that iodine can only be mixed with blood. In contrast, by allowing for any types of tissue-iodine mixtures, our method can be applied to other organ perfusion exams, such as in lungs or breasts. By choosing suitable base materials, the disclosed algorithm can be further applied to cerebral, renal, and hepatic perfusion exams. For example, for the cerebral perfusion imaging exams, the base materials can include fat, white matter, gray matter, bone, and tooth. This adaptive base material selection method can be readily implemented based on the CT exam type and organ segmentation techniques. Thus, accurate artifact-free pre-contrast images can be reconstructed and used as a priori information to linearize the iodine projections.

A fan beam was simulated with an equiangular arc detector. The simulation parameters are listed in Table 12. Quantum noise corresponding to $4.0 \times 10^5$ photons per detector pixel was added to the projection data. In this work, no inhomogeneous bow-tie filtering and scattering were taken into consideration. All simulations were conducted on a GPU Cluster with NVIDIA Tesla C1060 CPUs, which consists of 30 multiprocessors (each with eight SIMD processing cores) and 4 GB of memory.

TABLE 111

Simulation parameters used in the simulations.

| Parameter Name | Value |
| --- | --- |
| Source-to-detector distance | 1085.6 mm |
| Source-to-object distance | 595.0 mm |
| Number of detector bins | 736 |
| Detector size at iso-center | 0.60 × 0.60 mm² |
| Total photon number per detector bin | 4.0 × 10⁵ photons |
| Number of projections | 2304 projections |

A size-variable dynamic iodine calibration phantom (FIGS. 27A and 27B) was designed to compare the conventional FBP-based perfusion algorithm and the proposed pDP algorithm. In the pre-contrast phase (FIG. 27A), this phantom was composed of uniform soft tissue. In the post-contrast phase (FIG. 27B), five groups of iodine inserts with different concentrations (2, 6, 10, 14, 18 mg/cc) emerged from the soft tissue background. For each group, five iodine inserts with the same concentration were positioned at different radial distances. The size of this phantom was scaled to 16, 23, 30, and 37 cm diameters to simulate patients of different sizes. With this phantom, three tests, i.e., an iodine location test, a phantom size test, and an x-ray spectrum test, were performed to investigate the reconstruction stability of the algorithm. The parameters used in the three simulation tests are summarized in Table 13.

Figure 27A:
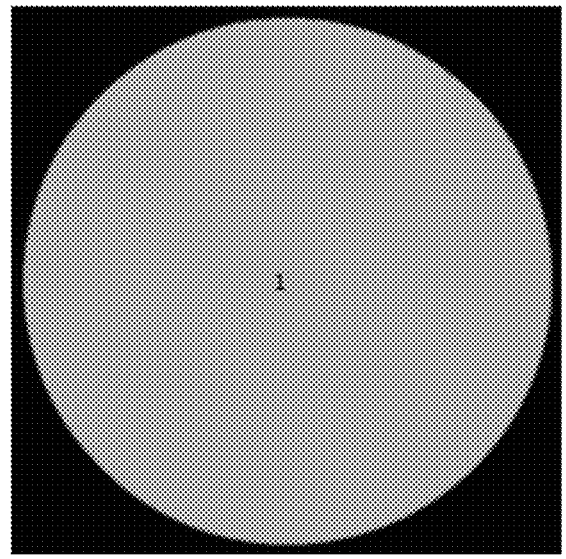
FIGS. 27A and 27B are images that provide definition of a dynamic calibration phantom.
Figure 27B:
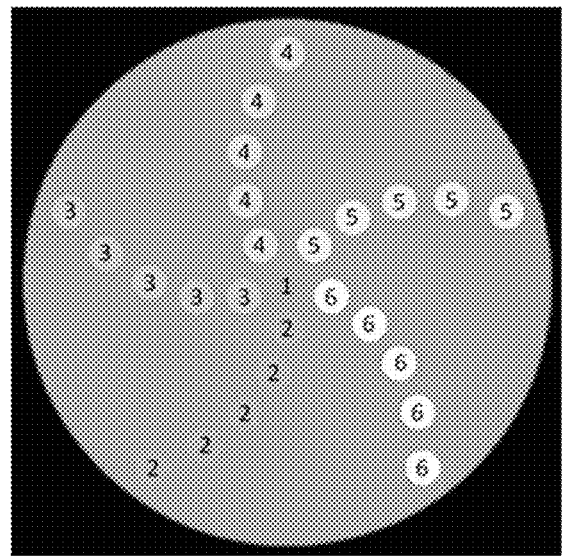

FIGS. 27A and 27B provide definition of the dynamic calibration phantom (1024×1024 pixels). In the pre-contrast phase, the phantom shown in FIG. 27A was only composed of uniform (1) soft tissue. In the post-contrast phase, the phantom shown in FIG. 27B was composed of (1) soft tissue, (2) 2 mg/cc iodine insert group, (3) 6 mg/cc iodine insert group, (4) 10 mg/cc iodine insert group, (5) 14 mg/cc iodine insert group, and (6) 18 mg/cc iodine insert group.

TABLE 112

Parameter summary of the simulation tests for the dynamic iodine calibration phantom.

| Simulation tests | Varying parameters | Fixed parameters | Individual parameters |
| --- | --- | --- | --- |
| Iodine location test | Radial distance of the iodine inserts | Spectrum: 80 kVp<br>Phantom size: 30 cm | FBP: water correction<br>pDP: $E_0$ = 70 keV |
| Phantom size test | Phantom size:<br>16, 23, 30, and 37 cm | Spectrum: 80 kVp | FBP: water correction<br>pDP: $E_0$ = 70 keV |
| X-ray spectrum test | X-ray spectrum:<br>80, 100, 120, 140 kVp | Phantom size: 30 cm | FBP: water correction<br>pDP: $E_0$ = 70 keV |

Figure 28A:
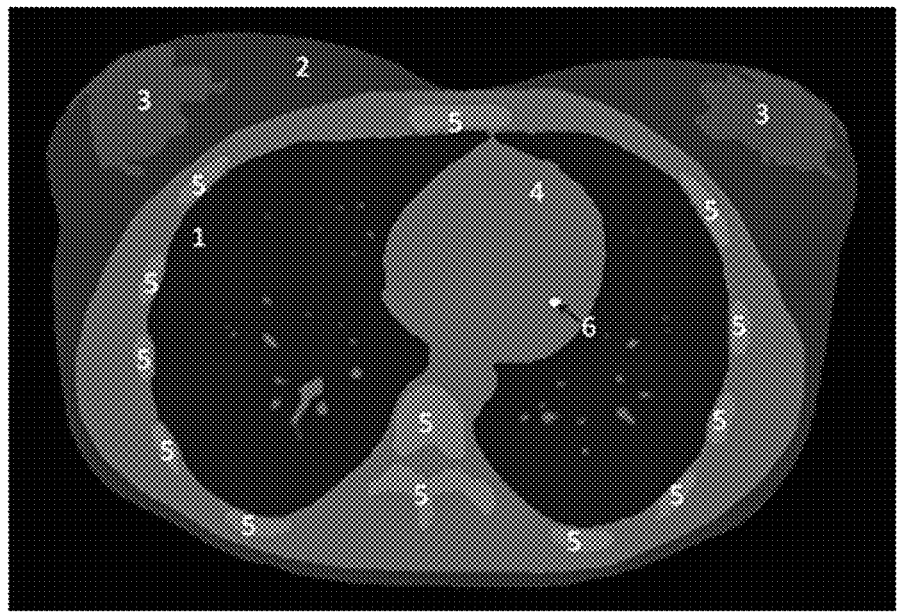
FIGS. 28A and 28B illustrate a definition of the dynamic anthropomorphic thorax phantom.
Figure 28B:
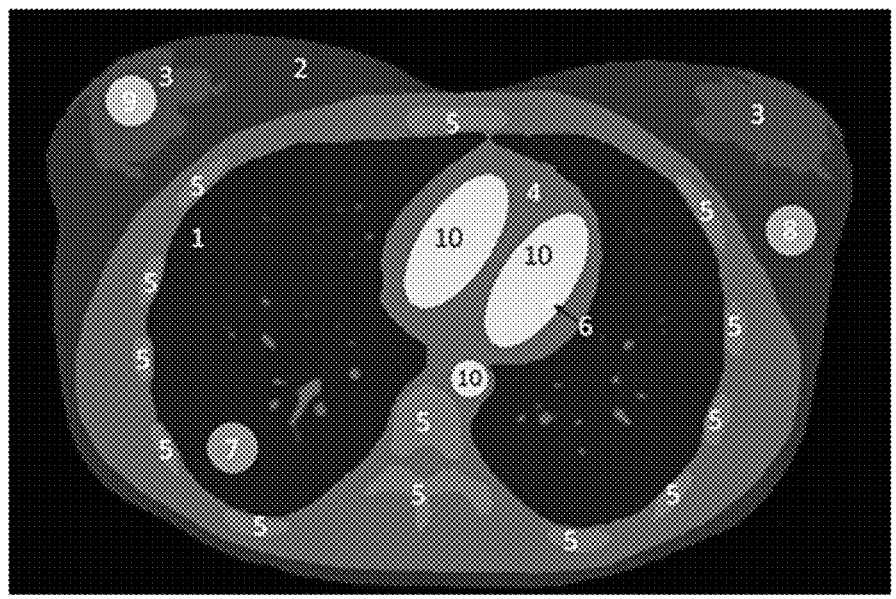

In order to further validate our reconstruction algorithm, real CT data from the database of The Cancer Imaging Archive (TCIA, http://www.cancerimagingarchive.net/) were used to create a more complex and realistic dynamic anthropomorphic thorax phantom (FIGS. 28A and 28B). The phantom was assumed idealized for tissue registration and contrast enhancement.

Figure 29:
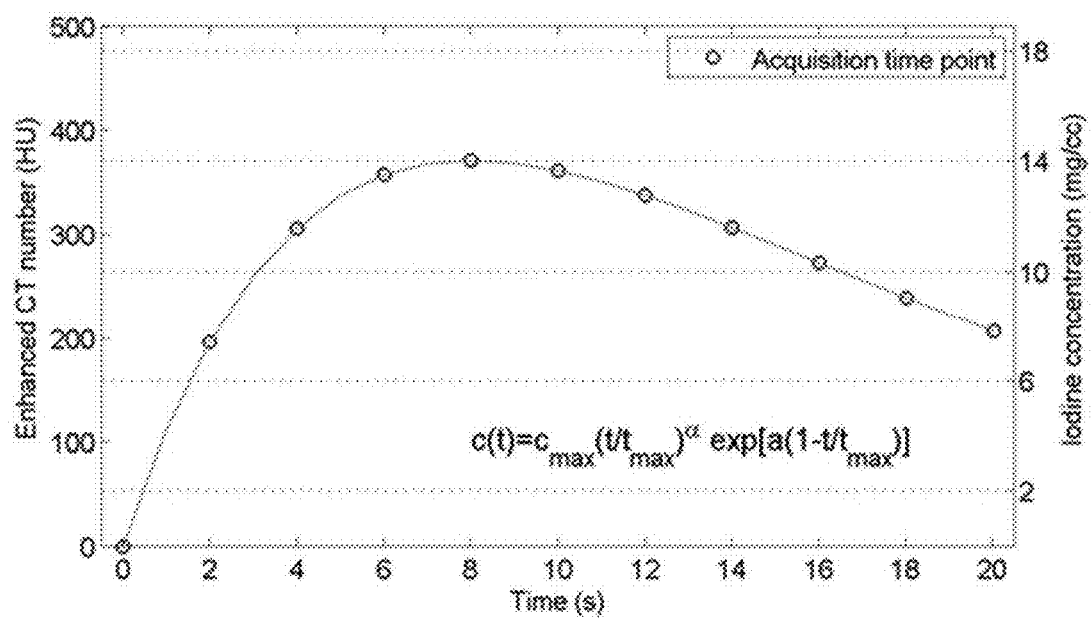
FIG. 29 illustrates a graph of the TAC of the different body tissue-iodine mixtures.

FIGS. 28A and 28B illustrate a definition of the dynamic anthropomorphic thorax phantom (2048×1400 pixels, 0.15× 0.15 mm2). In the pre-contrast phase shown in FIG. 28A, this phantom was composed of (1) lung, (2) fat, (3) breast, (4) soft tissue, (5) bone (1000 mg/cc), and (6) metal implant (titanium). In the post-contrast phase shown in FIG. 28B, iodine perfusion resulted in different iodine-body tissue mixtures, i.e., (7) lung-iodine mixture, (8) fat-iodine mixture, (9) breast-iodine mixture, and (10) soft tissue-iodine mixture. The TAC of those different body tissue-iodine mixtures is defined in FIG. 29, which illustrates a graph of the TAC of the different body tissue-iodine mixtures. The iodine concentration scale was added to the right-y axis for reference. Ten time points were sampled from 0s to 20s with 2s interval.

In the pre-contrast phase shown in FIG. 28A, this phantom was composed of diverse materials, i.e., (1) lung, (2) fat, (3) breast, (4) soft tissue, (5) bone (1000 mg/cc), (6) metal implant (titanium). In the post-contrast phase shown in FIG. 28B, iodine perfusion resulted in different tissue-iodine mixtures, i.e., (7) lung-iodine mixture, (8) fat-iodine mixture, (9) breast-iodine mixture, and (10) soft tissue-iodine mixture. In order to simulate the dynamic wash-in and wash-out kinetics, a gamma-variate function was employed to govern the concentration changes of the iodinated contrast agent as $$c(t)=c_{max}(t/t_{max})^a \exp[a(1-t/t_{max})] \quad (53)$$

The parameter a affects the rise and fall times of the function and was set to 1 in this work; the peak time $t_{max}$ was set to the 8 seconds for all tissues; the maximum iodine concentration $c_{max}$ at the peak time was set to 14 mg/ml for all tissues. In addition, a common set of regions of interest surrounding the left chamber (FIG. 30) was used to assess the effect of BH artifacts induced by iodinated contrast agent in both heart chambers and aorta. With this dynamic anthropomorphic thorax phantom, poly-energetic projections were simulated from 0s to 20s with a 2s interval. The projections were reconstructed by the conventional FBP algorithm and the proposed pDP algorithm. The simulation results were compared quantitatively.

Figure 30:
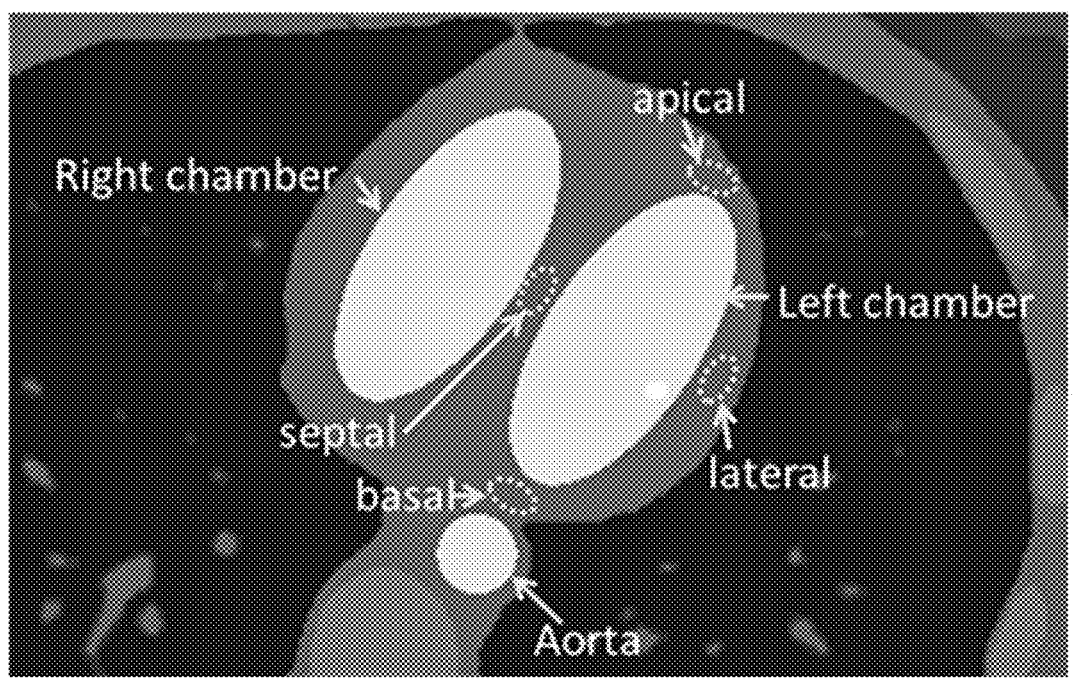
FIG. 30 is an image depicting anatomical structures in the heart region.

FIG. 30 depicts anatomical structures in the heart region. A set of ROIs (i.e., apical, septal, basal, and lateral) was used to evaluate the BH artifacts induced by iodine in both heart chambers and aorta.

Note that as this dynamic phantom was mainly used to validate the proposed algorithm, a single TAC was applied to all the body tissues. This choice enabled the comparison of the impact of iodine on the reconstruction values across different background tissues.

Figure 31:
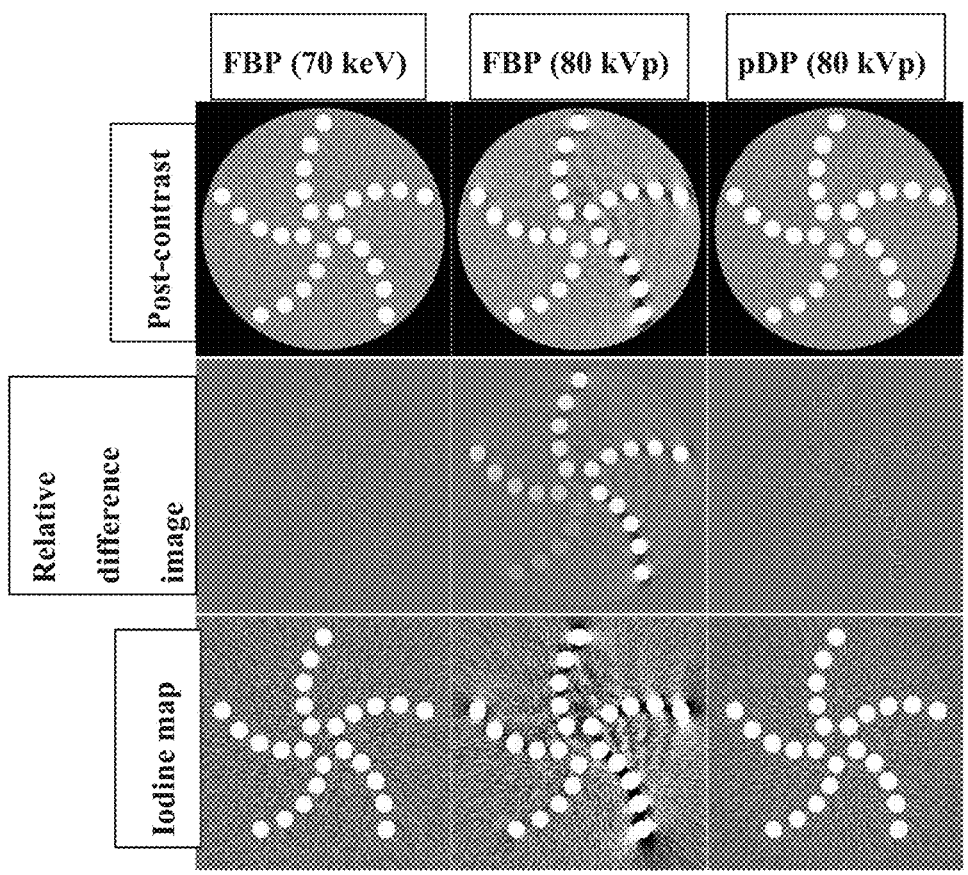
FIG. 31 shows reconstruction results of dynamic iodine calibration phantom in the post-contrast phase.

FIG. 31 shows the reconstruction results of the dynamic iodine calibration phantom in the post-contrast phase. The images in the first column were reconstructed by FBP (70 keV). Because of the mono-energetic spectrum, BH artifacts were not noticeable. The bright or dark boarders around the edges of the iodine inserts are due to the partial volume effect. The images in the first column were used as benchmarks for the rest of the comparisons. The percent relative difference image in the second row shows uniform zero values. The iodine map shown in the last row was obtained by subtracting the post-contrast image from the pre-contrast image, and it correctly retrieved all iodine inserts.

The post-contrast images reconstructed by FBP (80 kVp) are shown in the second column of FIG. 31, which illustrates reconstruction results of the dynamic iodine calibration phantom. The images from the first column to the third column were reconstructed by FBP (70 keV), FBP (80 kVp), and pDP (80 kVp), respectively. The images from the first row to the third row were post-contrast images (50/100), relative difference images (0%/20%), and iodine maps (0/40), respectively. Dark streak artifacts were readily visible. The percent relative difference image in the second row shows that iodine inserts were constantly over-estimated for all concentrations, which affects the accuracy of the quantitative perfusion assessment. By subtracting the post-contrast image from the pre-contrast image, we obtained the iodine map as presented in the last row. The BH artifacts were prominent in a narrow window level (0 HU/40 HU). As expected, the strength of the artifacts was positively correlated with the iodine concentration but inversely correlated with the distance between the iodine inserts. In addition, the strength of the artifacts was also positively correlated with the radial distance. For instance, for the 10 mg/cc iodine inserts, the shape of the iodine inserts near the center was round, but when approaching the phantom border, the shape was gradually deformed to an ellipse, the long axis of which was parallel to the shortest intersection line between the x-ray path and the phantom. This phenomenon was due to the cupping effect. For the iodine inserts close to the center, the x-rays from different directions were equally attenuated, so that the BH effect was isotropic and the shape of the iodine inserts could be preserved. However, for the iodine near the phantom boarder, BH effect was no longer isotropic. The directions with shorter intersection lines between the x-ray path and the phantom could induce stronger BH artifacts, because of the large amount of un-attenuated low energy photons. Water correction could not effectively eliminate this iodine-induced cupping effect.

The images in the last column of FIG. 31 were reconstructed by pDP (80 kVp). In comparison with FBP (80 kVp), the streaks caused by the iodine inserts were totally eliminated in the post-contrast image. The relative difference image in the second row had uniformly negligible values. The iodine map in the last row was nearly identical with the iodine map obtained by FBP (70 keV).

Figure 32A:
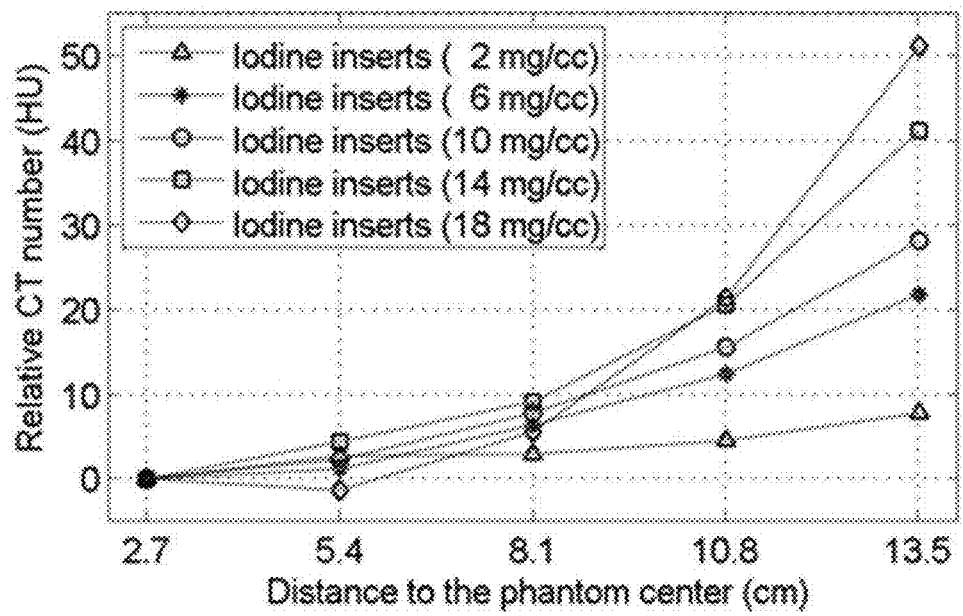
FIGS. 32A and 32B show the location test results of the dynamic iodine calibration phantom.
Figure 32B:
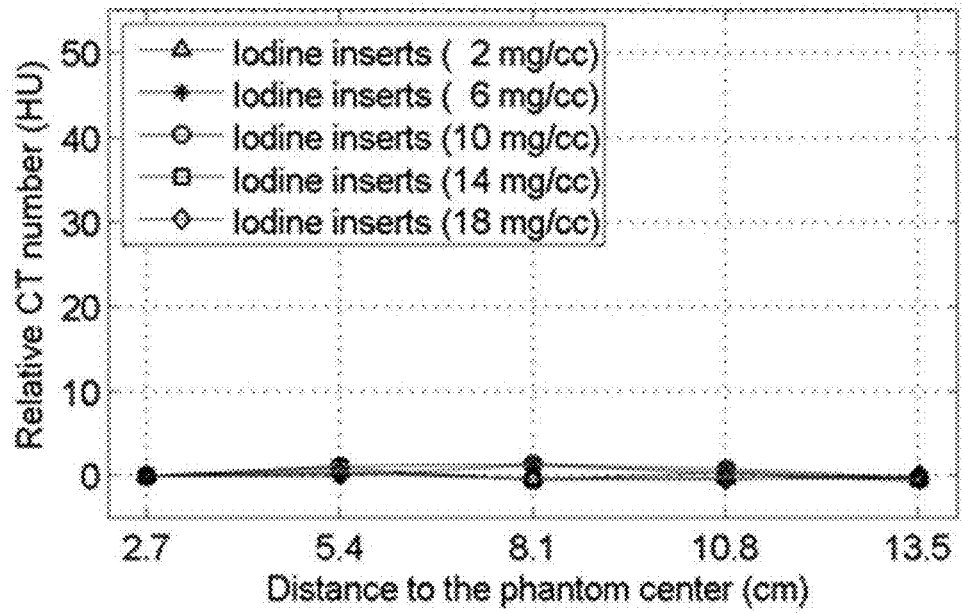

FIGS. 32A and 32B show the location test results of the dynamic iodine calibration phantom (30 cm and 80 kVp). For the iodine inserts within the same group, their relative CT numbers with respect to the iodine insert nearest to the phantom center were plotted against the radial distance for algorithms FBP (FIG. 32A) and pDP (FIG. 32B). To facilitate comparison, the CT numbers of the iodine inserts in the same concentration group were subtracted from the value of the innermost iodine insert to yield the relative CT numbers, which were then plotted against the radial distance. For FBP (FIG. 32A), the maximum intragroup difference of the iodine inserts was more than 50 HU. With regard to algorithm pDP, the maximum intragroup difference was reduced below 3 HU, which indicated that the cupping effect was eventually eliminated.

Figure 33:
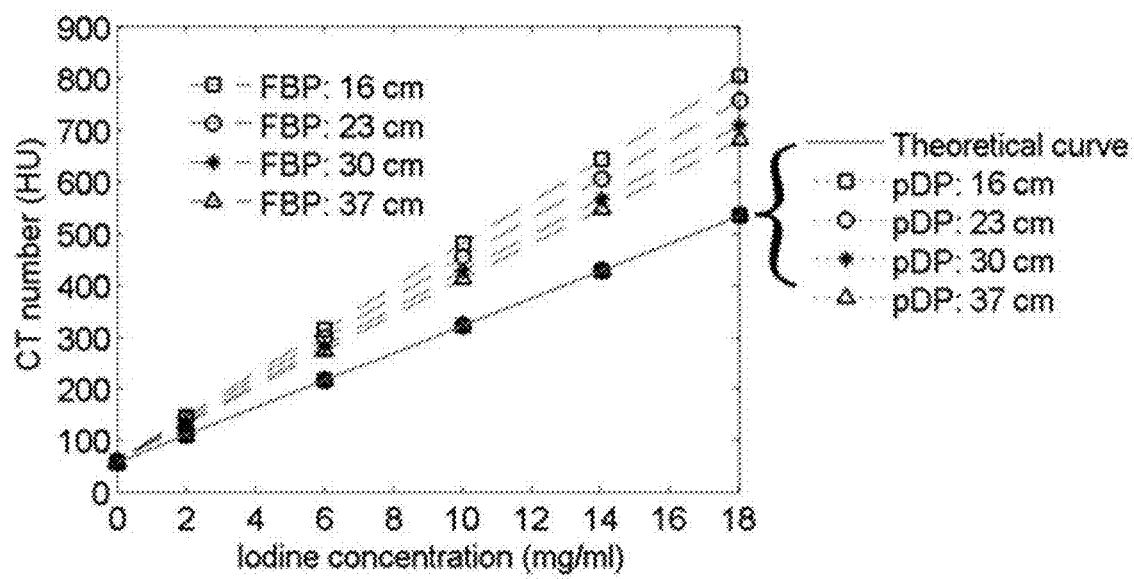
FIG. 33 is a graph showing attenuation-concentration curves derived from the phantom size test.

In the phantom size test, by varying the phantom size (16, 23, 30, 37 cm) under the same spectrum (80 kVp), a series of projection datasets were simulated and then reconstructed by FBP and pDP. For each reconstructed images, the CT numbers of the iodine inserts in the same group were averaged and plotted against their corresponding theoretical iodine concentrations (FIG. 33). Ideally, the theoretical iodine concentration curve should be y=26.46x+58.33, where x (mg/ml) represents the iodine concentration, 26.46 (HU·ml/mg) is the iodine concentration factor, 58.33 (HU) is the CT number of unenhanced soft tissue, and y (HU) represents the CT number. The theoretical curve was plotted in solid line as a reference. The FBP results were plotted in dashed line. Due to the BH effect, all the iodine concentration curves tended to be over-estimated and the slopes of those curves increased with decreased phantom size. In comparison, the curves derived from the pDP algorithm (dotted line in FIG. 33) perfectly overlapped with the theoretical curve. Linear regression method was performed to compute the iodine concentration curves with a correlation coefficient of greater than 0.999 (Table 14). The high agreement of our proposed algorithm indicated our algorithm was independent of the patient size.

FIG. 33 is a graph showing attenuation-concentration curves derived from the phantom size test. By varying the phantom size (square: 16 cm; circle: 23 cm; star: 30 cm; triangle: 37 cm), iodine concentration curves were plotted for different reconstruction algorithms (solid line: FBP; dotted line: pDP). All simulations in this test used the 80 kVp spectrum.

Table 113 shows linear regression results of the attenuation-concentration curves derived from the phantom size test and spectrum test. The parameters x (mg/ml) and y(HU) represent the iodine concentration and the CT number, respectively.

Figure 34:
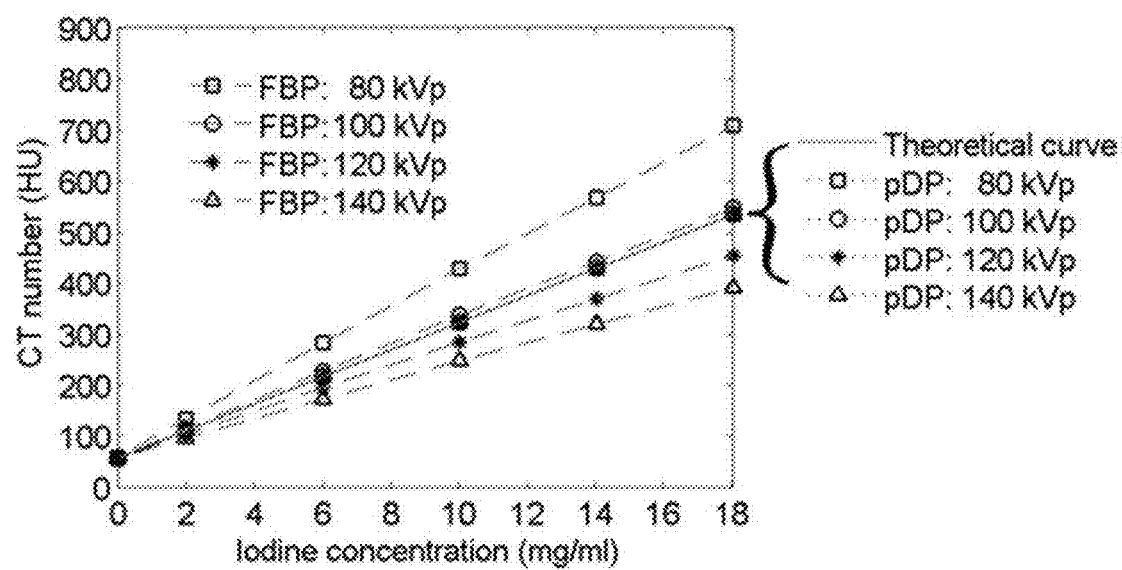
FIG. 34 is a graph showing iodine concentration curves derived from the spectrum test.

By varying the x-ray spectrum (80, 100, 120, 140 kVp), iodine concentration curves for algorithms FBP and pDP were computed and plotted in FIG. 34, which illustrates a graph showing iodine concentration curves derived from the spectrum test. By varying the x-ray spectrum (square: 80 kVp; circle: 100 kVp; star: 120 kVp; triangle: 140 kVp), iodine concentration curves are plotted for different reconstruction algorithms (solid line: FBP; dotted line: pDP). All simulations in this test used the 30 cm diameter phantom. For FBP, only the curve derived from the 100 kVp spectrum was close to the theoretical trend and that was only for the phantom at 30 cm diameter. In comparison, the curves derived from pDP accorded with the theoretical curves very well across x-ray spectrum. The accuracy of the agreements can be further quantitatively reflected by the linear regression results in Table 14.

Figure 35:
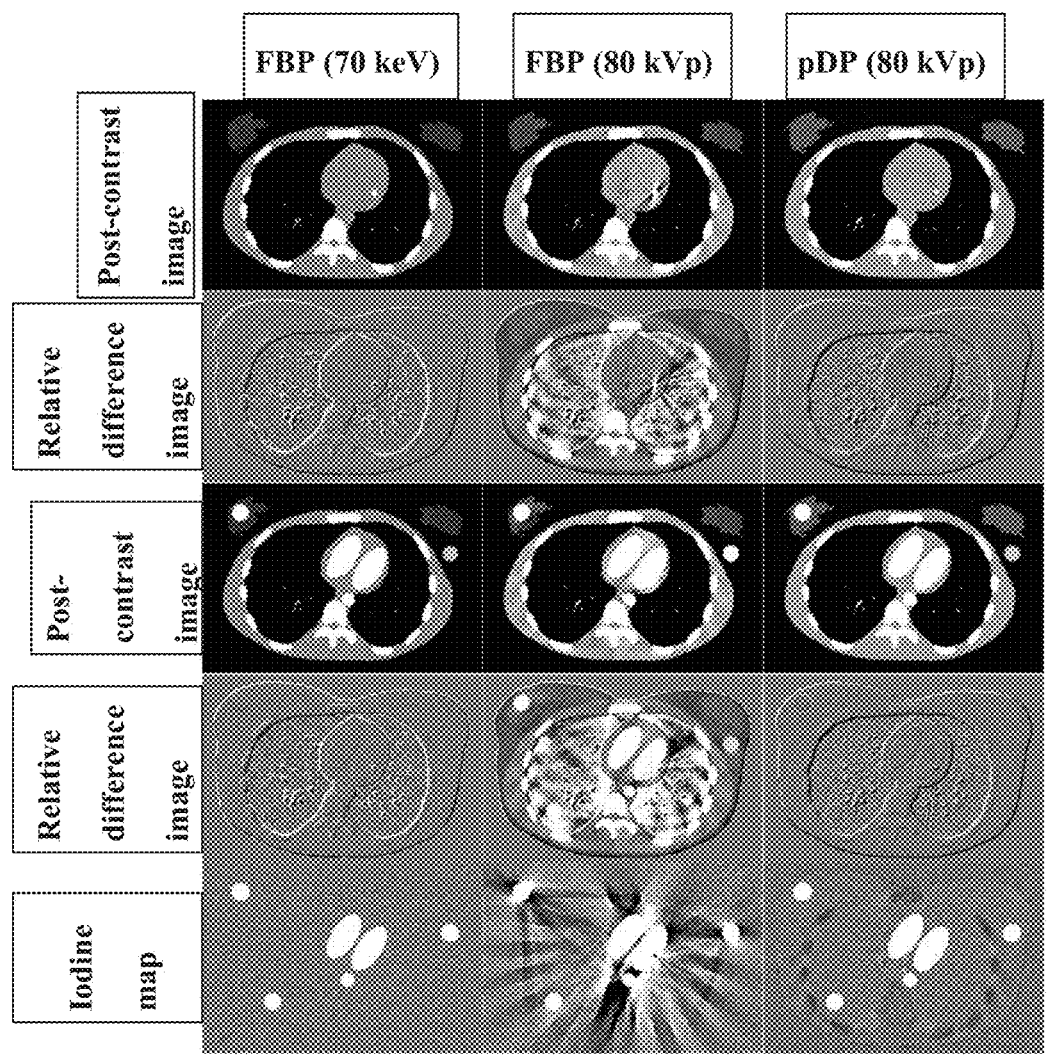
FIG. 35 are images showing reconstruction results of the dynamic anthropomorphic thorax phantom.

The reconstruction results of the dynamic anthropomorphic thorax phantom are shown in FIG. 35, which illustrates images showing reconstruction results of the dynamic anthropomorphic thorax phantom. The images from the first column to the third column were reconstructed by FBP (70 keV), FBP (80 kVp), and pDP (80 kVp), respectively. The images from the first row to the last row are pre-contrast images (−70/130), relative difference images (0%/20%) of the pre-contrast images, post-contrast images (−70/130), relative difference images (0%/20%) of the post-contrast images, and iodine maps (0/40), respectively. The images reconstructed by FBP with mono-energetic spectrum (70 keV) are presented in the first column as benchmark results. The images reconstructed by FBP and pDP from the same poly-energetic projection dataset (80 kVp) are presented in the second and third columns, respectively. The reconstructed images and relative difference images of the pre-contrast phase are shown in the first two rows; the reconstructed images and relative difference images of the post-contrast phase with the peak iodine concentration are shown in the third and fourth rows. The iodine maps are shown in the last row.

In the first column of FIG. 35, due to a mono-energetic spectrum, the images reconstructed by FBP (70 keV) were free of BH artifacts in the pre- and post-contrast images. The second column depicts the reconstruction results of FBP (80 kVp), where BH artifacts severely deteriorated the image quality. For instance, the metal implant in the pre-contrast image resulted in strong streaks in the heart region and obscured the heart detail. Bones around thoracic cage resulted in visible artifacts to the neighboring soft tissue. In the post-contrast images, other than the mentioned artifacts, the iodinate inserts lowered the attenuations of the breast tissue and the high concentrations of contrast in the left chamber blood pool and descending aorta severely impacted the attenuation density in myocardium. The relative images of the pre- and post-contrast images visually show the error distributions. Fat and breast tissues tended to be under-

TABLE 14

| Simulation tests | Spectrum/Phantom size | FBP | pDP |
| --- | --- | --- | --- |
| Phantom size test | 80 kVp/16 cm | y = 41.23x + 64.43 | y = 26.41x + 58.06 |
|  | 80 kVp/23 cm | y = 38.59x + 64.48 | y = 26.47x + 58.08 |
|  | 80 kVp/30 cm | y = 35.99x + 63.69 | y = 26.51x + 57.61 |
|  | 80 kVp/37 cm | y = 34.45x + 63.98 | y = 26.54x + 57.31 |
| Spectrum test | 80 kVp/30 cm | y = 35.99x + 63.69 | y = 26.51x + 57.61 |
|  | 100 kVp/30 cm | y = 27.12x + 62.09 | y = 26.50x + 58.15 |
|  | 120 kVp/30 cm | y = 21.97x + 61.28 | y = 26.51x + 58.40 |
|  | 140 kVp/30 cm | y = 18.45x + 60.87 | y = 26.50x + 58.67 | estimated, but bones and iodinated regions tended to be over-estimated. The iodine map in the last row was contaminated by the bright and dark streaks and the shape of some iodine inserts were not correctly reconstructed.

The images in the last row were reconstructed by pDP (80 kVp). In comparison with FBP (80 kVp), the artifacts induced by the bones, the metal implant, and the iodinated contrast agent were completed eliminated in both pre- and post-contrast images. The image appearance was almost the same with that reconstructed by FBP (70 keV). The relative difference images yielded uniformly negligible values. The iodine map in the last row correctly reflected the iodine distribution.

Figure 36A:
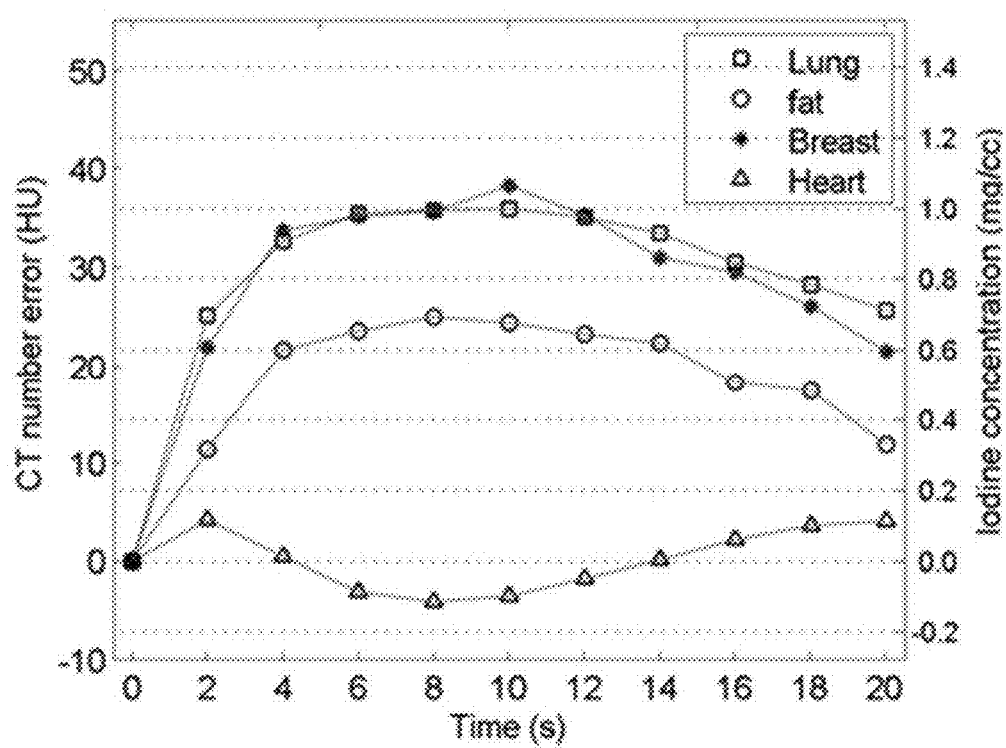
FIGS. 36A and 36B are graphs depicting the CT number error profiles of the iodine TACs/TCCs in different iodinated regions, i.e., lung, fat, breast, and heart.
Figure 36B:
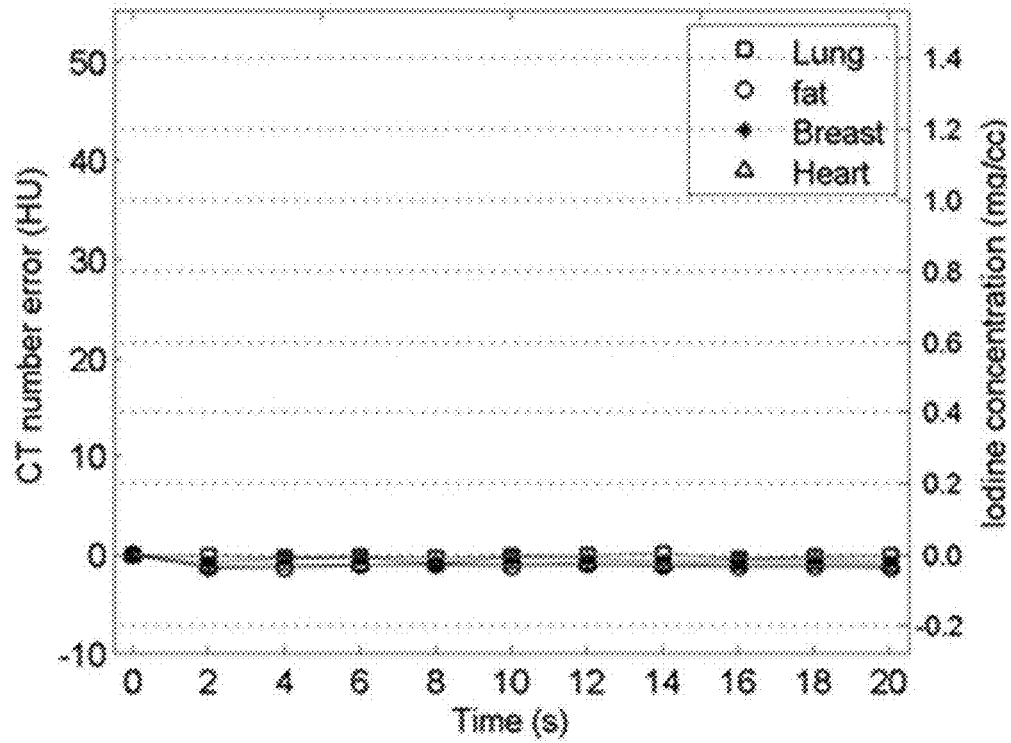
Figure 37A:
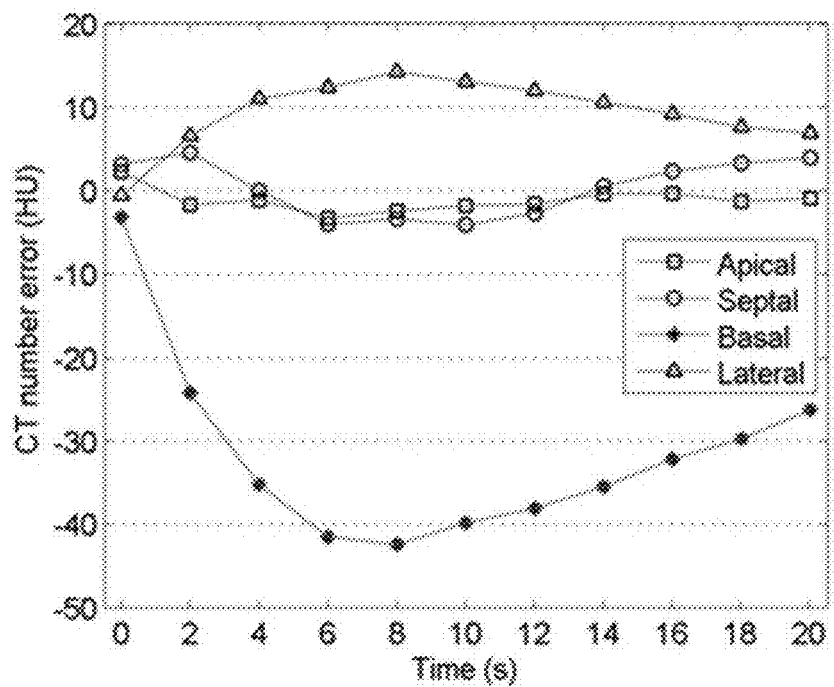
FIGS. 37A and 37B depict CT number error profiles of ROIs as defined in a dynamic anthropomorphic phantom.
Figure 37B:
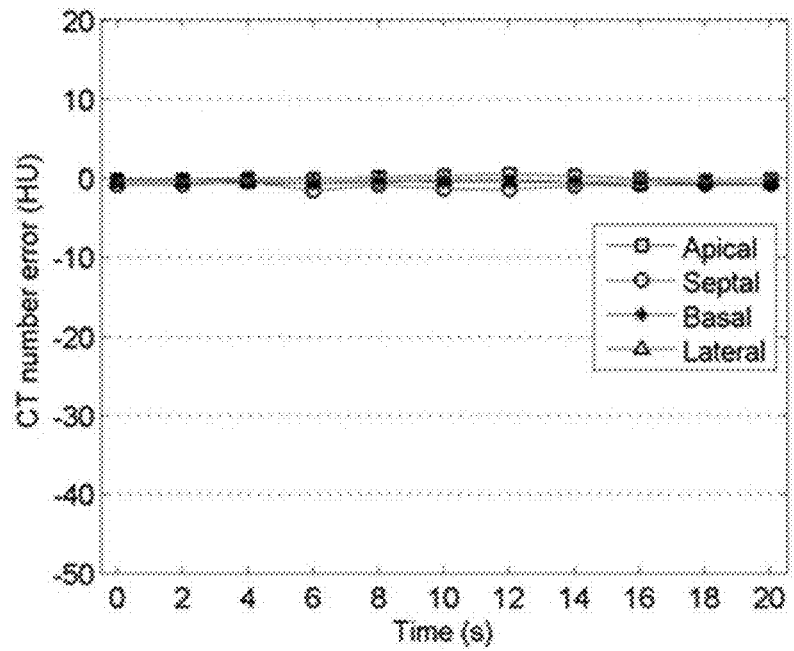

FIGS. 36A and 36B are graphs depicting the CT number error profiles of the iodine TACs/TCCs in different iodinated regions, i.e., lung, fat, breast, and heart. For FBP (FIG. 36A), as the average diameter of the dynamic anthropomorphic thorax phantom was approximately 30 cm, iodine concentration curve y=35.99x+63.69 (Table 14) was applied to reduce the errors of the CT numbers and the iodine concentrations. However, only the error profile of the iodinated heart was close to zero values, which benefited from the same background tissue with the iodine calibration phantom. CT number error profiles due to BH enhancement in the four ROIs as defined in FIG. 29 in the dynamic anthropomorphic thorax phantom for algorithms FBP (FIG. 36A) and pDP (FIG. 36B). Because the shape and the structure of the thorax phantom were different from those of the iodine calibration phantom, discrepancies were still observable. Among all the body tissues, as the attenuation property of the lung tissue deviated most from that of soft tissue, the error profile of lung yielded highest deviations. The error profile of breast tissue also had a similar error magnitude with that of lung, which was caused by the cupping effect (FIG. 36A). If iodine concentration curves were not applied, those curves would have had even larger errors. For FBP, the maximum error was more than 40 HU, i.e., 1.1 mg/cc in iodine concentration. Improvement in the error profiles was evident by using pDP algorithm, and all error profiles were close to zero values. FIGS. 37A and 37B depict the CT number error profiles of the four ROIs as defined in the dynamic anthropomorphic phantom (FIG. 30). For FBP (FIG. 36A), large deviations caused by BH effect could be observed in the basal wall of the left heart chamber and the maximum deviation was as large as −42 HU. The lateral wall also had relative large deviation, which was probably due to the metal artifacts. The BH enhancement of the other two ROIs was relatively small. By contrast, the BH across all ROIs disappeared with the case of pDP (FIG. 36B).

In accordance with embodiments, the disclosed subject matter can be used to model the attenuation properties of diverse base materials (e.g., lung, fat, breast, soft tissue, bone, implant metal, and iodine) in the reconstruction process. Because the attenuation properties of the tissue mixtures are computed by interpolating two predefined base materials, the presently disclosed subject matter does not result in ill-posed problems or unstable solutions, but can improve reconstruction accuracy and stability as shown in our previous studies via a base material transition test.

For each post-contrast phase, the iodine projections can be obtained by linearization and be used directly to reconstruct artifact-free iodine maps. As the reconstructed iodine maps can realistically reflect the iodine concentrations, it is not necessary to pre-compute the iodine concentration curves for different spectra and different sized phantoms.

The methodology is not limited to blood-iodine mixtures. The proposed perfusion algorithm can be applied to organ-based perfusion exams as well (e.g., lung, fat, and breast). Note that if certain patient anatomical information or material distribution information are reasonably assumed, adaptive base material decomposition can be employed to better decompose the tissue mixtures. For example, the breast tissue can be confined only in the breast region, and the base material set for this region can include fat, breast, soft tissue, and calcifications only. Doing so, the fat-soft tissue mixtures would not be mis-interpreted into breast related mixtures in the other body regions.

As no segmentation is required in our method, misinterpretations of the voxel types due to the threshold-based segmentation method can be avoided.

In experiments, two phantoms were used to validate the proposed algorithm, i.e., a dynamic iodine calibration phantom and a dynamic anthropomorphic thorax phantom. The dynamic iodine calibration phantom was used to investigate the reconstruction stabilities of the iodinated contrast agent in terms of various influential factors (i.e., iodine location, phantom size, and x-ray spectrum). The simulation results showed that, for the widely used FBP-based perfusion algorithm, the errors of the iodine concentration factor (HU·ml/mg) were in a large range (i.e., [−8.01, 14.77]), which indicated that the iodine concentration curve highly depended on these influential factors, making it necessary to apply the pre-calibrated iodine concentration curve to reduce the errors. In contrast, the disclosed methods can accurately model the attenuation properties of iodine, so that the error range was reduced to [−0.05, 0.08], effectively eliminating the BH effect.

A realistic dynamic anthropomorphic thorax phantom was utilized to further investigate the reconstruction performance of the proposed algorithm. The simulation results showed that, for FBP, the reconstructed images suffered from severe BH artifacts caused by bone, iodine, and metal implant. The strong artifacts seriously affected the accuracy of the CT numbers. For example, the deviation of the time-attenuation curves of the soft tissue around the left heart chamber was as large as −40 HU. Though iodine concentration curve was applied to the iodine inserts, the errors of the voxel values was still larger than 40 HU, which was equivalent to a 1.1 mg/ml deviation in iodine concentration. There are two major reasons for this large discrepancy. First, the strong cupping artifacts could significantly affect the iodinated tissues near the periphery the patient body. Second, as the iodine concentration curves were mainly derived from iodinated blood or soft tissue, the errors could be introduced when applying those curves to other iodinated tissues. For pDP, the BH artifacts due to bone and iodine were completely eliminated and the metal artifacts were also greatly reduced. The quantitative results showed that the time-attenuation curves of both soft tissue ROIs and different iodinated tissues could be accurately derived.

For the iodine map reconstructed in accordance with embodiments of the present disclosure, the values of the voxels originally containing bones were slightly less than zero (i.e., the darker region in the bone locations), which is due to the iteration cutoff in the pre-contrast image reconstruction. Because of only using four iterations, the bone inserts in the pre-contrast reconstructed images were about 0.1% overestimated. This overestimation, after being magnified by the large attenuation of bone, systematically decreased the accumulated lengths of iodine ($l_{r,7}^{post}$ in Eq. 15) and thus caused a negative bias in the iodine map images. This negative bias can be corrected either by reconstructing more accurate pre-contrast images using more iterations or simply by filtering negative voxels in the post-contrast images using thresholding method. As this negative bias does no impact iodine distributions, it was not corrected in experiments described herein.

Two smoothing kernels were used in accordance with the present disclosure. It was not necessary to optimize these filters, as the purpose of experiments described herein was to eliminate beam hardening effect and not to improve the noise properties of the images as affected by the choice of the smoothing kernels.

In accordance with embodiments, angle-dependent estimation techniques are disclosed herein. By use of the disclosed subject matter, the incident spectra across a wide range of angular trajectories can be estimated accurately with only a single phantom and a single axial scan in the absence of the knowledge of the bowtie filter.

The disclosed subject matter can use a uniform cylindrical phantom, made of ultra-high-molecular-weight polyethylene (UHMWPE) and positioned in an off-centered geometry. The projection data acquired with an axial scan have a twofold purpose. First, they serve as a reflection of the transmission measurements across different angular trajectories. Second, they are used to reconstruct the cross sectional image of the phantom, which is then utilized to compute the intersection length of each transmission measurement. With each CT detector element recording a range of transmission measurements for a single angular trajectory, the spectrum is estimated for that trajectory. A data conditioning procedure is used to combine information from hundreds of collected transmission measurements to accelerate the estimation speed, to reduce noise, and to improve estimation stability. The proposed spectral estimation technique was validated experimentally using a clinical scanner (Somatom Definition Flash, Siemens Healthcare, Germany) with spectra provided by the manufacturer serving as the comparison standard. Results obtained with the proposed technique were compared against those obtained from a second conventional transmission measurement technique with two materials (i.e., Cu and Al). After validation, the proposed technique was applied to measure spectra from the clinical system across a range of angular trajectories [−15°, 15°] and spectrum settings (80, 100, 120, 140 kVp).

At 140 kVp, the proposed technique was comparable to the conventional technique in terms of the mean energy difference (MED, −0.29 keV) and the normalized root mean square difference (NRMSD, 0.84%) from the comparison standard compared to 0.64 keV and 1.56%, respectively, with the conventional technique. The average absolute MEDs and NRMSDs across kVp settings and angular trajectories were less than 0.61 keV and 3.41%, respectively, which indicates a high level of estimation accuracy and stability.

An angle-dependent estimation technique of CT x-ray spectra from rotational transmission measurements is disclosed herein. Compared with the conventional technique, the proposed method simplifies the measurement procedures and enables incident spectral estimation for a wide range of angular trajectories. The proposed technique is suitable for rigorous research objectives as well as routine clinical quality control procedures.

With the improvements of the diagnostic imaging technologies, there are increasing demands for the accurate knowledge of the x-ray spectrum produced by a particular x-ray source. For example, in dose and risk estimations for computed tomography (CT), the x-ray spectrum can be used in Monte Carlo simulations to determine the energy deposition in a patient body. In poly-energetic reconstruction or dual energy reconstruction, the x-ray spectrum can be used as a priori information to reduce beam hardening artifacts and to implement quantitative imaging approaches. The x-ray spectrum can be measured for quality assurance purposes, as the spectrum of an x-ray source can drift from the expected values due to repeated usage.

Disclosed herein are transmission-measurement-based approaches for clinical CT scanners. Using a single cylindrical phantom and a single axial scan, incident spectra across a wide range of angular trajectories can be estimated without the knowledge of the bowtie filter characteristics. The method may utilize access to the raw data from the manufacturer. However, the measurements can be made without having the gantry in the stationary mode.

The transmission measurements can be expressed as an integral equation as $$Y(L) = \int_E I(E) e^{-\mu(E)L} dE \qquad , \qquad (54)$$
$$= \int_E N(E) \eta(E) E e^{-\mu(E)L} dE$$

where $Y(L)$ is the transmission measurement, $I(E)$ is the photon intensity at energy E, $\mu(E)$ is the attenuation coefficient of the phantom, and L is the x-ray intersection length through the phantom. As a conventional x-ray imaging CT system has energy-integrating detectors, $I(E)$ can be further broken into three components: the incident spectrum $N(E)$ (the objective of the characterization), the detector response $\eta(E)$, and the photon energy E. In this work, $\int I(E) dE$ is normalized to one, so the transmission measurement $Y(L)$ is equivalent to the transmission ratio.

Generally, the measurement expressed in Equation 54 follows a compound Poisson distribution. Previously developed statistical image reconstruction methods have used the assumption of simple Poisson statistics with acceptable results. Herein, the latter assumption was adopted, i.e., each measurement $Y(L)$ is assumed to follow a simple Poisson distribution with the mean intensity of $\int_E I(E)e^{-\mu(E)L} dE$ as $$Y(L) = \text{Poisson}\left\{ \int_E I(E) e^{-\mu(E)L} dE \right\}, \qquad (55)$$

or $$Y_m = \text{Poisson}\left\{ \sum_{s=1}^{N_S} A_{m,s} I_s \right\}, m = 1, \ldots, N_M, \qquad (56)$$

in the discretization form, where $N_M$ is the total number of transmission measurements, $N_S$ is the number of samplings of the spectrum, $A_{m,s}$ is the system matrix element computed from the phantom attenuation, the phantom thickness, and the size of the discretized spectral interval $\Delta E$ using the relation $$A_{m,s} = e^{-\mu_s L_m} \Delta E. \qquad (57)$$

Based on the simple Poisson assumption, the probability of obtaining $Y_m$ with the photon intensity spectrum $I_s$ can be computed as $$p(I \mid Y, A) = \prod_m \frac{\left(\sum_s A_{m,s} I_s\right)^{Y_m}}{(Y_m)!} e^{-\sum_s A_{m,s} I_s}, \quad (58)$$

where $I=(I_1, \ldots, I_{N_S})^T$, $Y=\{Y_1, \ldots, Y_{N_M}\}^T$, and $A=\{A_{m,s}\} \in R^{N_M \times N_S}$. In order to estimate $I_s$, one possible approach is to maximize the log-likelihood objective function of Eq. 5 through $$I = \arg\left\{\max_{A,Y} \ln P(I \mid A, z)\right\} \quad (59)$$

$$= \arg\left\{\max_{A,Y} \sum_m \left[Y_m \ln\left(\sum_s A_{m,s} I_s\right) - \sum_s A_{m,s} I_s\right] + c\right\},$$

where c is a constant. As a logarithmic function is concave, based on Jensen's inequality, Eq. 6 can be equivalently converted to $$I = \arg\left\{\max_{A,Y} \sum_{m,s} [Y_m \ln(A_{m,s} I_s) - A_{m,s} I_s] + c\right\}. \quad (60)$$

Since this objective function is not quadratic, an Expectation-Maximization (EM) approach is applied to solve this maximization problem. The resulting iteratively multiplicative update form is $$I_s^{(k)} = \frac{I_s^{(k-1)}}{\sum_m A_{m,s}} \sum_m \frac{A_{m,s} Y_m}{\sum_{s'} A_{m,s'} I_{s'}^{(k-1)}}, \quad (61)$$

where k indicates the k-th iteration. For the EM method, the main features of the spectrum (such as the characteristic x-rays of the x-ray tube and the K-edges of the detector) must be reflected in the initial guess ($I_s^{(0)}$). After each iteration, the sum of $\Sigma I_s^{(k)}$ is normalized to one. The iteration can be terminated when the averaged error is smaller than a threshold T as $$\frac{1}{N_M} \sum_{m=1}^{N_M} \left| Y_m - \sum_{s=1}^{N_S} A_{m,s} I_s^{(k)} \right| \leq T. \quad (62)$$

Usually, the iterative equation (Equation 61) converges within about $3.0 \times 10^3$ iterations for $T=10^{-5}$. The computational time is less than 2 s using Matlab running on a desktop computer (3 GB RAM and 2.5 GHz CPU). With $I_s$, the incident spectrum $N_s$ can be obtained by dividing the detector response $\eta_s$ and the energy $E_s$ as $$N_s = \frac{I_s}{\eta_s E_s}. \quad (63)$$

Because of the bowtie filter, the incident spectrum N(E) gradually changes as a function of beam angle. In order to fast and accurately sample the transmission measurements across a wide range of angular trajectories, we propose an off-centered acquisition geometry as shown in FIG. 37, which illustrates a diagram showing off-centered acquisition geometry for the angle-dependent estimation technique of x-ray spectrum.

Figure 38:
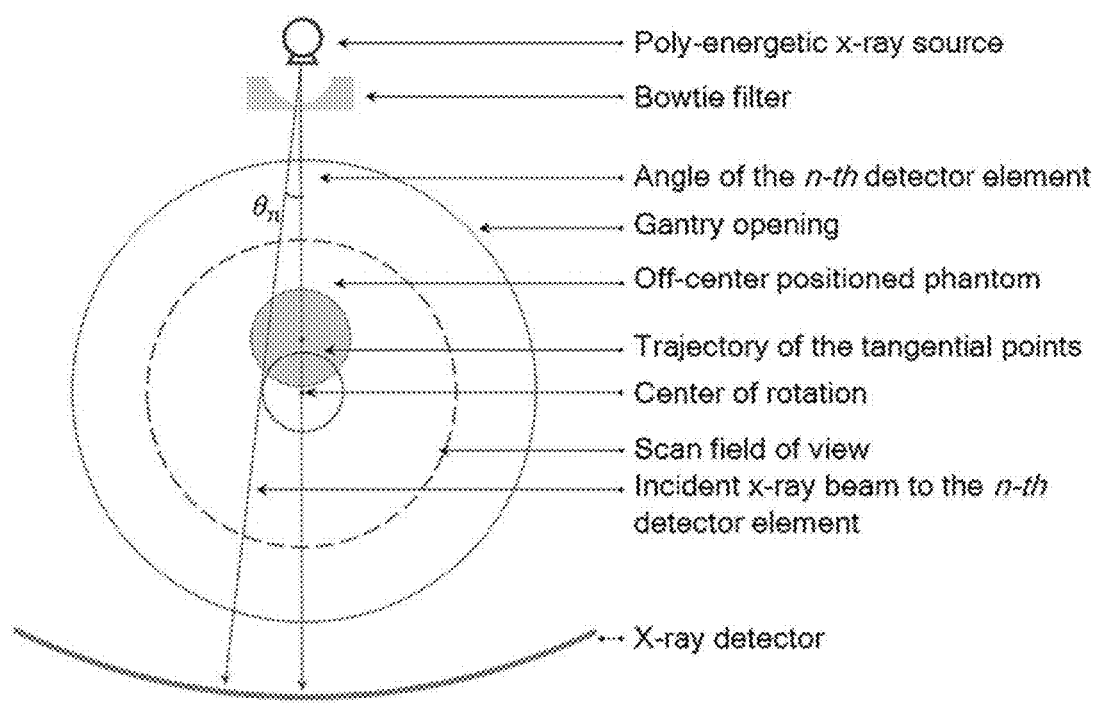
FIG. 38 is a diagram showing placement of a poly-energetic x-ray system.
Figure 39:
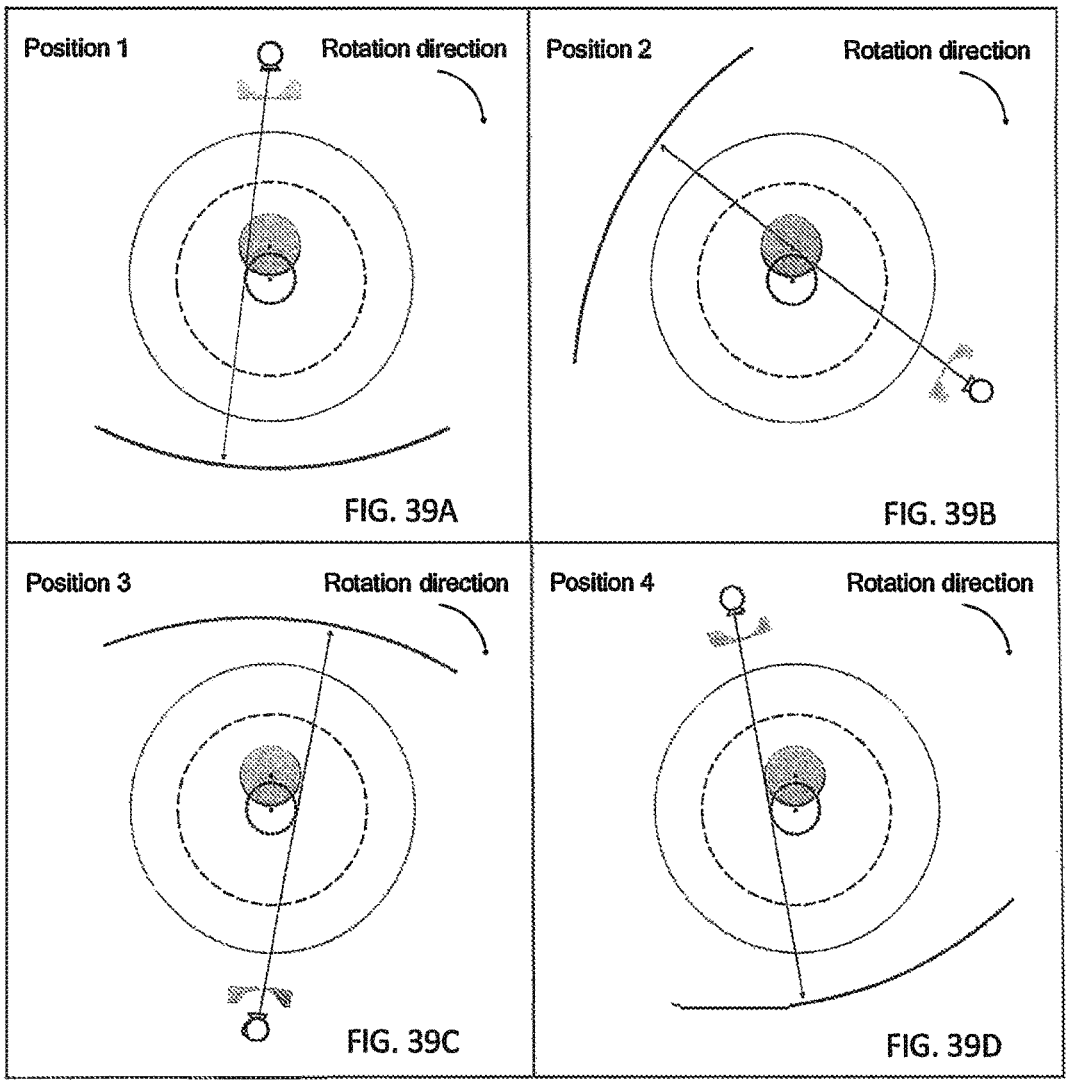
FIGS. 39A-39D illustrate schematic diagrams of the change of the attenuation path of the x-ray beam from the x-ray source to the n-th detector element during the CT scan in axial mode.

Using a cylindrical shaped phantom and targeting the transmission measurements of the n-th detector element, the x-ray beam from the x-ray source to the n-th detector element is always tangent to a circle (dotted line in FIG. 38) with its center located at the center of the gantry rotation. Based on this circle, one can trace the position of this x-ray beam and determine the corresponding intersection length during the rotation of the gantry as shown in FIGS. 39A-39D, which illustrate schematic diagrams of the change of the attenuation path of the x-ray beam from the x-ray source to the n-th detector element during the CT scan in axial mode. Starting from position 1 (FIG. 39A), the intersection length gradually increases to the maximum (i.e., the diameter of the phantom) at position 2 (FIG. 39B), decreases to zero at position 3 (FIG. 39C), and then starts to increase again from zero value at position 4 (FIG. 39D). Based on this off-centered geometry, the detectors from different angles can quasi-continuously record a series of transmission measurements with a large range of intersection lengths.

Figure 40:
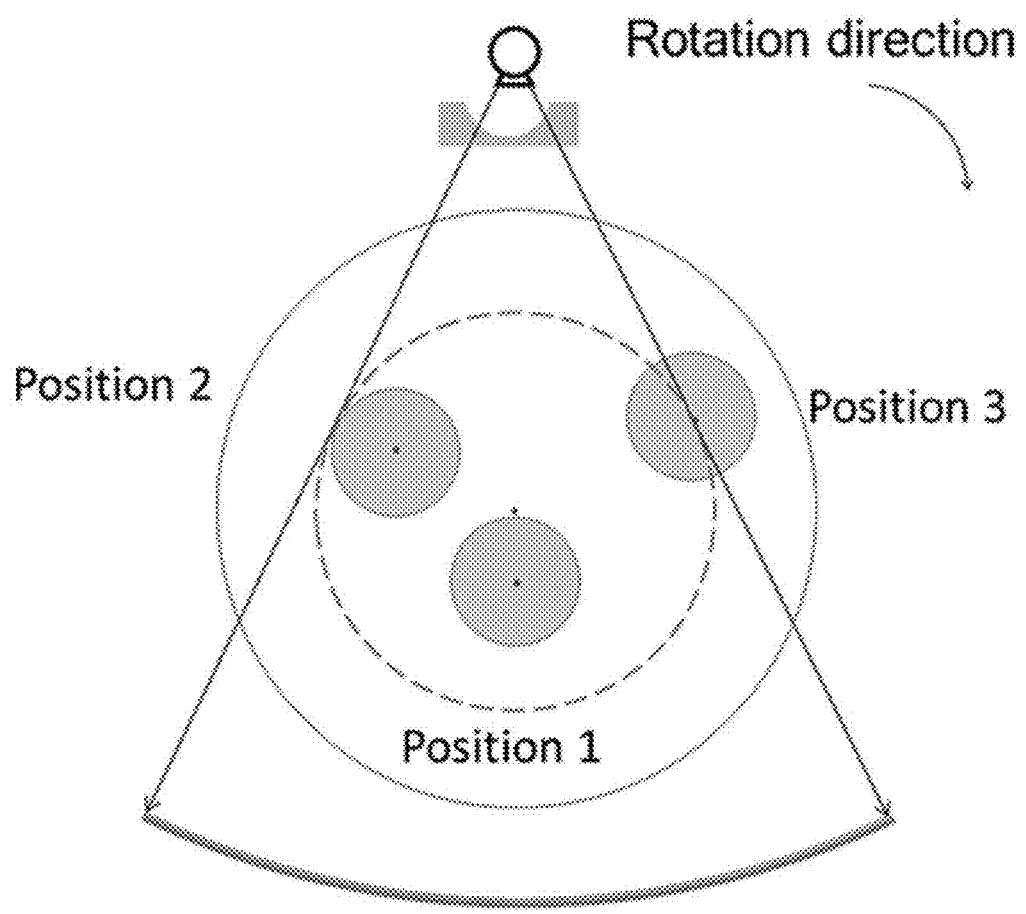
FIG. 40 illustrates a diagram of various possible off-centered positions.

FIG. 40 illustrates a diagram of various possible off-centered positions. At position 1, the distance between the center of the phantom and the rotation center is slightly larger than the radius of the phantom. At position 2, the phantom is tangent to the SFOV. At position 3, a part of the phantom is positioned outside of the SFOV. In order to make sure the ranges of the intersection lengths of the central detector elements can always start from zero, the phantom should be kept completely off from the center of rotation (e.g., position 1 in FIG. 40). With the increase of the distance between the phantom and the rotation center, the phantom can cover a larger range of angular trajectories. The furthest location to position the phantom is position 2 in FIG. 40, where phantom is tangent to the SFOV. When the detector is rotated to the closest location to the phantom during the CT scan, scatter radiation can increase proportionally (see our Monte Carlo simulation results provided herein). As a scanned object is usually positioned in the center, the built-in model-based correction techniques can effectively reduce the scatter radiation via tabulated tables. Therefore, it would be advantageous for the phantom to be positioned only slightly off-centered as in position 1 (FIG. 40), so that the scatter radiation pattern is more similar to that of the centered phantom and the scatter radiation across all projections can be readily corrected by the scanner's built-in scatter correction techniques. Positioning the phantom in position 2 provides a wider sampling of the angular trajectories but a larger impact of scatter radiation on the measurements. Note that phantom located beyond position 2 (e.g., position 3 in FIG. 40) can further result in truncated projections and the cross sectional image cannot be accurately reconstructed for the derivation of the intersection lengths using conventional FBP method. Dedicated reconstruction algorithms for truncated projections have to be employed to extend the CT SFOV for this case.

As the phantom is positioned within the SFOV and the CT scanner is operated in axial mode with the x-rays continuously on for a full rotation, the collected transmission data can be used to reconstruct the cross-sectional image of the scanned phantom. The voxel values that are larger than half of the attenuation of the scanned material can be set to unit one to facilitate deriving the intersection lengths via the forward ray tracing procedure. If the shape of the phantom is convex, a conventional backward ray tracing technique can be used to delineate the border of the phantom instead of using image reconstruction.

The phantom can be made of a material with moderate attenuation properties. Materials with large attenuations (such as metals) can be small in size, but the accuracy of the intersection lengths derived from the reconstructed image will suffer large errors due to the limited resolution of the CT detectors (0.6×0.6 mm² at iso-center). Materials with small attenuations provide for a larger phantom enabling smaller relative errors in intersection length measurement, but can lead to increased scatter radiation to the detectors. Plastic materials, such as ultra-high-molecular-weight polyethylene (UHMWPE; chemical formula: $(C_2H_4)_nH_2$, density: 0.937 g/cm³), have moderate attenuations. In experiments, a 160 mm diameter cylindrical phantom made of polyethylene was used to reduce transmission to 0.1 for the maximum path length through the phantom for a typical 140 kVp beam.

The off-centered acquisition geometry can collect hundreds of transmission measurements across a wide range of angular trajectories, which provides abundant experimental data. However, the large amount of data can make the estimation process time consuming, while the data are further contaminated by various sources of noise (such as quantum noise, instrumentation noise, or stochastic variations due to the phantom and the experimental condition). In order to accelerate spectral estimation speed, to reduce noise, and to improve estimation stability, the data is pre-processed before spectral estimation.

Generally, the transmission measurements can be fitted with polynomial functions. Equation 54 can be expanded in a Taylor series as $$Y(L) = \int_E I(E)e^{-\mu(E)L}dE, \qquad (64)$$

$$= \sum_k c_k L^k$$

where $$c_k = \int_E \frac{I(E)[E-\mu(E)]^k}{k!}dE. \qquad (65)$$

Figure 41:
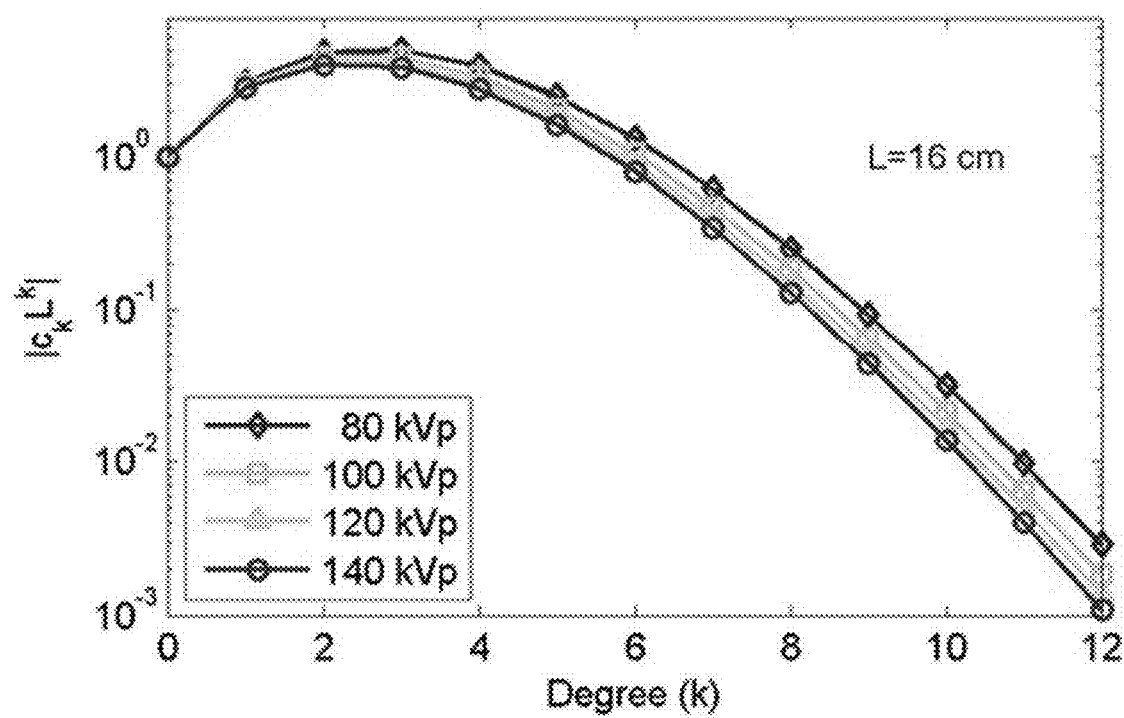
FIG. 41 shows a graph of an absolute value of the k-th term ($|c_k L^k|$) of an example equation.

Because the intersection length L can be very large (e.g., 160 mm), it is necessary to ensure that the Taylor series converges with a suitable truncation degree. In order to make this determination, the absolute value of the n-th term ($|c_k L^k|$, where L=160 mm) of Equation 64 is plotted in FIG. 41 as a function of polynomial degree (k) for different spectra. In this example, we used a polynomial function with a truncation degree of 11 to maintain errors to be less than $10^{-2}$. Particularly, FIG. 41 shows a graph of an absolute value of the k-th term ($|c_k L^k|$, where L=160 mm) of the Taylor series in Equation 64 as a function of polynomial degree (k) for different spectra.

One boundary condition that may be imposed to the polynomial function is that the transmission measurements $Y_m$ may always be 1 when x-ray beam is not attenuated (L=0). Because of the limited resolution of the detector and various sources of noise, when an x-ray path approaches the edge of the phantom, the derived intersection length might change dramatically and the fitted function may not necessarily satisfy this boundary condition. In order to force the polynomial functions through this fixed point, $c_0$ in Equation 64 is set to unity. In matrix notation, the equation for a polynomial fit is given by $$Y-1=Lc, \qquad (66)$$

where $1=[1, \ldots, 1]^T \in R^{N_M \times 1}$, L is the Vandermonde matrix generated by the $L_m$, i.e., $$L = \begin{bmatrix} L_1^1 & \cdots & L_1^{N_K} \\ \vdots & \ddots & \vdots \\ L_{N_M}^1 & \cdots & L_{N_M}^{N_K} \end{bmatrix}, \qquad (67)$$

and $c=[c_1, \ldots, c_{N_K}]^T \in R^{N_K \times 1}$ is the vector of unknown polynomial coefficients. In this work, the linear equation system of Eq. 13 is solved using a fixed point least square method as $$c=(L^T L)^{-1}L^T(Y-1). \qquad (68)$$

With the fitted polynomial function for each angular trajectory, 30 measurements equally distributed between L=0 were resampled, and the measured maximum intersection length for the spectral estimation.

The spectral estimation technique disclosed herein was validated on a CT scanner (Somatom Definition Flash, Siemens Healthcare, Germany). Details of the pre-bowtie spectra (140, 120, 100, and 80 kVp), the bowtie filter, and the detector absorption ratios were provided from the manufacturer. These spectra were measured with a spectroscopic x-ray detector using a Compton scattering method. The bowtie filter was used to derive the incident spectra along different angular trajectories from manufacturer-provided pre-bowtie spectra. The detector absorption ratios were used to convert the estimated photon intensities to incident spectra (Equation 63). The CT geometric information and the scan parameters used are specified in Table 15.

TABLE 145

CT geometric information and scan parameters used in this work.

| Parameter name | Value |
| --- | --- |
| Source-to-detector | 1085.6 mm |
| Source-to-object distance | 595.0 mm |
| Gantry opening | 780 mm |
| Number of detector columns | 736 |
| Fan angle | 49.95° |
| Detector size at iso-center | 0.60 × 0.60 mm² |
| Detector collimation | 2 × 1 mm |
| Bowtie filter | w3 |
| Tube current | 500 mAs |
| Exposure time | 1.0 s |
| Number of projections | 1152 projections for the proposed technique |

In order to reduce the potential influence of the quantum noise, a high mAs setting (i.e., 500 mAs) was used. The obtained two-row data were then averaged with respect to each column to further suppress the quantum noise.

A comparative experiment was conducted between the conventional technique and the proposed technique. For one technique, two materials (i.e., Al and Cu) were selected. For each material, nine metal filters of different thicknesses were used. The thicknesses of the metal filters were selected to ensure uniformly-distributed transmission measurements within the [0.0, 1.0] range (Table 16). Actual thicknesses of the metal filters were measured with a caliper. For this technique, the scanner was operated in the service mode, i.e., both the x-ray tube and the detector remained stationary. The metal filters were positioned in a proximate location to the x-ray tube to minimize the scatter radiation and the transmission measurements through the metal filters were acquired sequentially along the central axis of the beam.

TABLE 16

Technical description of the Al and Cu filters at 140 kVp.

| Material | Density (g/cm³) | | 1 | 2 | 3 | 4 | 5 | 6 | 7 | 8 | 9 |
|---|---|---|---|---|---|---|---|---|---|---|---|
| Al | 2.700 | L (mm) | 1.000 | 3.000 | 5.000 | 7.500 | 10.500 | 14.500 | 20.500 | 25.500 | 40.500 |
| | | Transmission Y(L) | 0.936 | 0.819 | 0.721 | 0.616 | 0.514 | 0.401 | 0.286 | 0.206 | 0.098 |
| Cu | 8.960 | L (mm) | 0.127 | 0.254 | 0.655 | 1.062 | 1.562 | 2.090 | 3.124 | 3.658 | 4.686 |
| | | Transmission Y(L) | 0.864 | 0.761 | 0.546 | 0.415 | 0.303 | 0.229 | 0.140 | 0.112 | 0.074 |

Figure 42A:
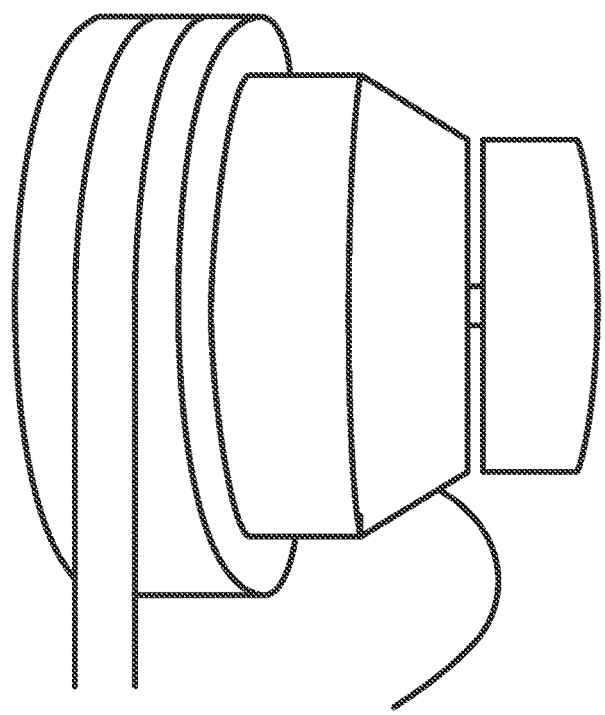
FIGS. 42A and 42B are images of the experimental setup in accordance with the present disclosure.
Figure 42B:
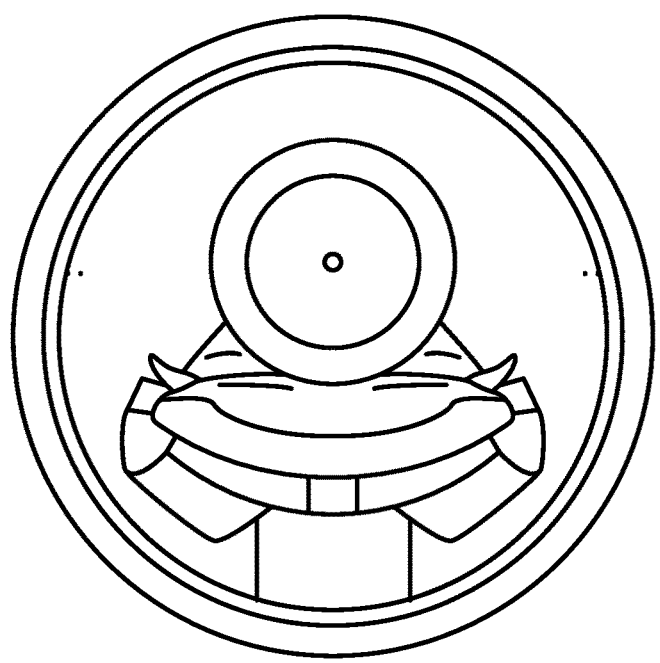

In a technique in accordance with embodiments of the present disclosure, a cylindrical phantom with a 160 mm diameter was used, which was made of uniform ultra-high-molecular-weight polyethylene. The experimental setup is shown in FIGS. 42A and 42B, which are images of the experimental setup in accordance with the present disclosure. In the first step shown in FIG. 42A, the scanning section of the phantom was extended beyond the patient table to avoid the influence of the patient bed in the followed CT scan. In the second step shown in FIG. 42B, the phantom was positioned off-center in the SFOV by adjusting vertically the patient bed. First, the scanning section of this phantom was extended beyond the patient table to avoid the influence of the patient bed (FIG. 42A). Second, this phantom was positioned off center in the SFOV by adjusting vertically the patient bed (FIG. 42B). With the proposed technique, the scanner was able to be operated in the axial mode. After measurement, raw data were exported from the scanner to an external computer, from which the transmission data were extracted for spectral estimation via a manufacturer-provided program. The beam-hardening corrections were excluded from the transmission data.

To reduce the influence of the scatter radiation, a 2×1 mm collimation was used. A Monte Carlo simulation with MC-GPU indicated that the scatter-primary ratios (SPRs) of position 1 in FIG. 40 were less than 0.008 for 140 kVp, consistent with the results of previous studies. As the SPRs of the transmission data were further reduced by the built-in scatter correction strategies of Somatom Flash Definition scanner (e.g., an anti-scatter grid), it was postulated that the actual SPRs of the transmission data can be less than that value estimated by the Monte Carlo simulation, and then inconsequential to the measurements. It was further demonstrated in a secondary analysis that the distance between the phantom and the detector had negligible influence on the transmission measurements (see FIG. 46).

Figure 43:
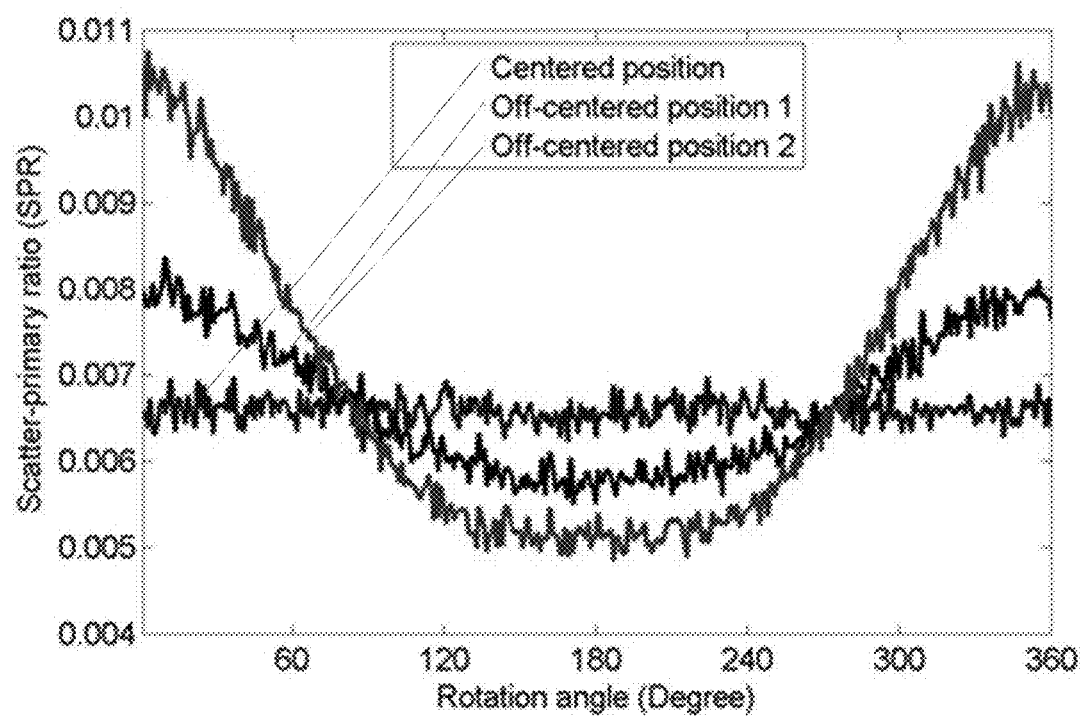
FIG. 43 depicts a graph showing Monte Carlo simulation results of the maximum scatter primary ratio as a function of rotation degree for three different phantom positions.

FIG. 43 depicts a graph showing Monte Carlo simulation results of the maximum scatter primary ratio as a function of rotation degree for three different phantom positions, i.e., the centered position, the off-centered position 1 in FIG. 40, and the off-centered position 2 in FIG. 40. The geometry of the Somatom Definition Flash scanner was simulated with a perfect detector (2×1 mm collimation) and without an anti-scatter grid using Monte Carlo simulation code MC-GPU. A cylindrical phantom made of polyethylene (160 mm in diameter and 250 mm in height) was imaged at 140 kVp.

Figure 44:
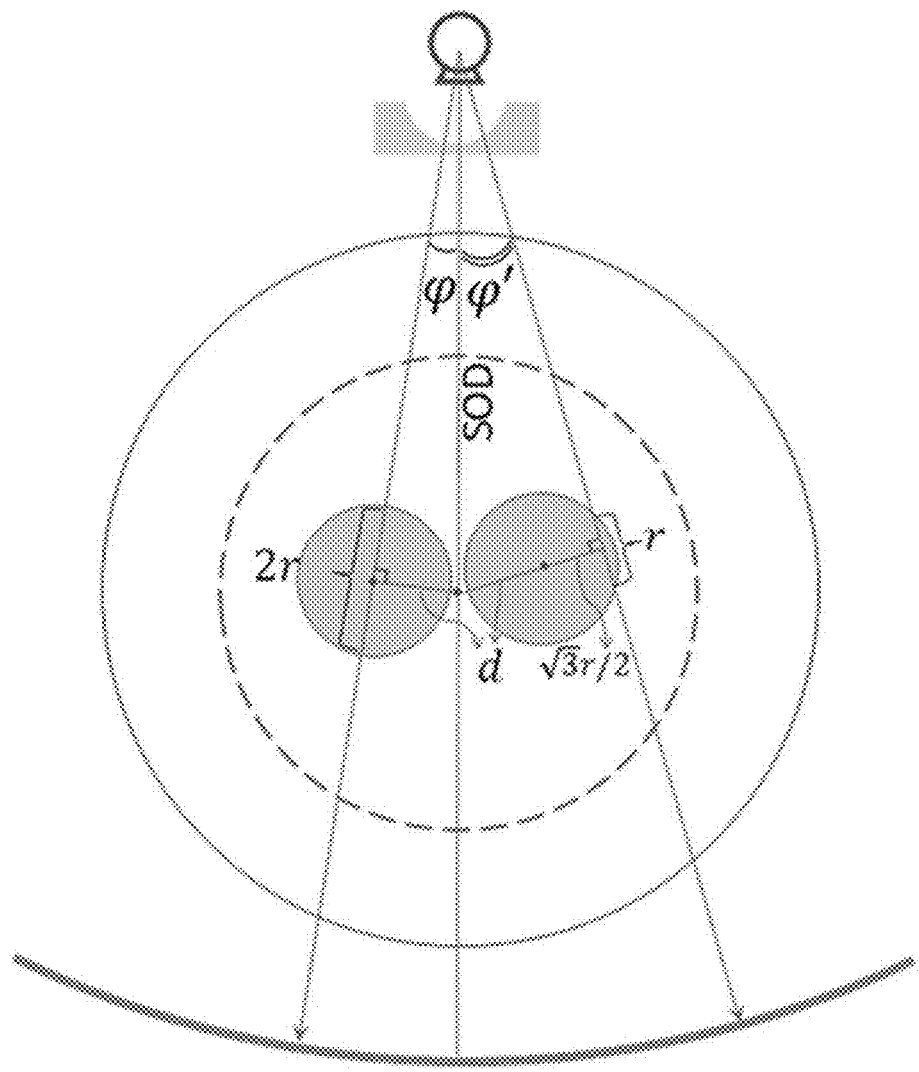
FIG. 44 illustrates a schematic diagram to show the maximum fan angles $\varphi$ and $\varphi'$ determined by the maximum intersection lengths of $2r$ and $r$, respectively.

The maximum fan angle of the estimated spectra depends on the phantom radius r and the distance d between the phantom center and the rotation center. If the x-ray path is required to pass through the phantom center to achieve the maximum intersection length of 2r (FIG. 44), the maximum fan angle would be $$\varphi = \pm \frac{180°}{\pi} \arcsin\left(\frac{d}{SOD}\right), \tag{69}$$

where SOD is the source-to-object distance (i.e., 595 mm). In that condition, based on our experimental setup (d=80 mm, i.e., position 1 in FIG. 40), the angular trajectories would be within $[\theta_{114}, \theta_{622}] = [-8°, 8°]$, where the subscript in $\theta_n$ indicates the detector index. However, results (in Table 4) indicate that it is possible to obtain spectra with good accuracy even if the maximum intersection length is reduced to r (FIG. 44). FIG. 44 illustrates a schematic diagram to show the maximum fan angles $\varphi$ and $\varphi'$ determined by the maximum intersection lengths of 2r and r, respectively. In that condition, the transmission measurements are reduced to about 0.2 and the maximum fan angle is extended to $$\varphi' = \pm \frac{180°}{\pi} \arcsin\left(\frac{d + \sqrt{3}\, r/2}{SOD}\right). \tag{70}$$

According to the above equation, the range of the angular trajectories was extended to $[\theta_{147}, \theta_{589}] = [-15°, 15°]$ for the geometry used in this experiment. The coverage of these results is less than the CT scanner's fan angle (i.e., [−25°, 25°]). The quarter detector offset was considered negligible assuming the angle of the central detector element to be zero, i.e., $\theta_{368} = 0°$.

The incident spectrum of the central detector element at 140 kVp was estimated by the conventional and the proposed technique. The results were compared in terms of the mean energy difference (MED) and the normalized root mean square deviation (NRMSD). The MED was defined as the mean energy of the estimated spectrum minus the mean energy of the manufacturer-provided spectrum. The NRMSD was defined as $$NRMSD = \frac{\sqrt{\sum_s (N_s - N_s^*)^2 / N_E}}{\max(N_s^*) - \min(N_s^*)}, \tag{71}$$

where $N_s^*$ is the expected spectrum, $N_s$ is the estimated spectrum, and $N_E$ is the total number of the energy bins. In addition, the incident spectra of the detector elements between −15° and 15° were estimated and were quantitatively compared with the incident spectra derived from the manufacturer-provided spectra. Note that as the manufacturer-provided spectra cannot be assumed to be the actual gold standard, the MED and NRMSD may not be interpreted as metrics of absolute accuracy.

Figure 45A:
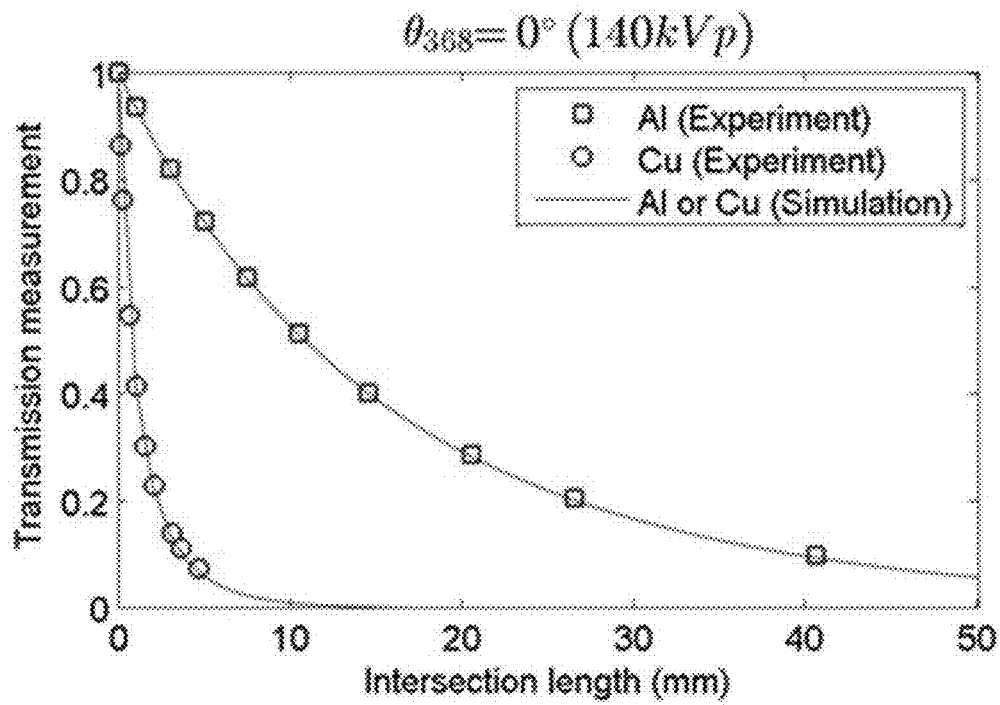
FIGS. 45A and 45B are graphs of a comparison of the experimental results and the simulated results in terms of the transmission measurement as a function of the intersection length for the central detector element at 140 kVp.
Figure 45B:
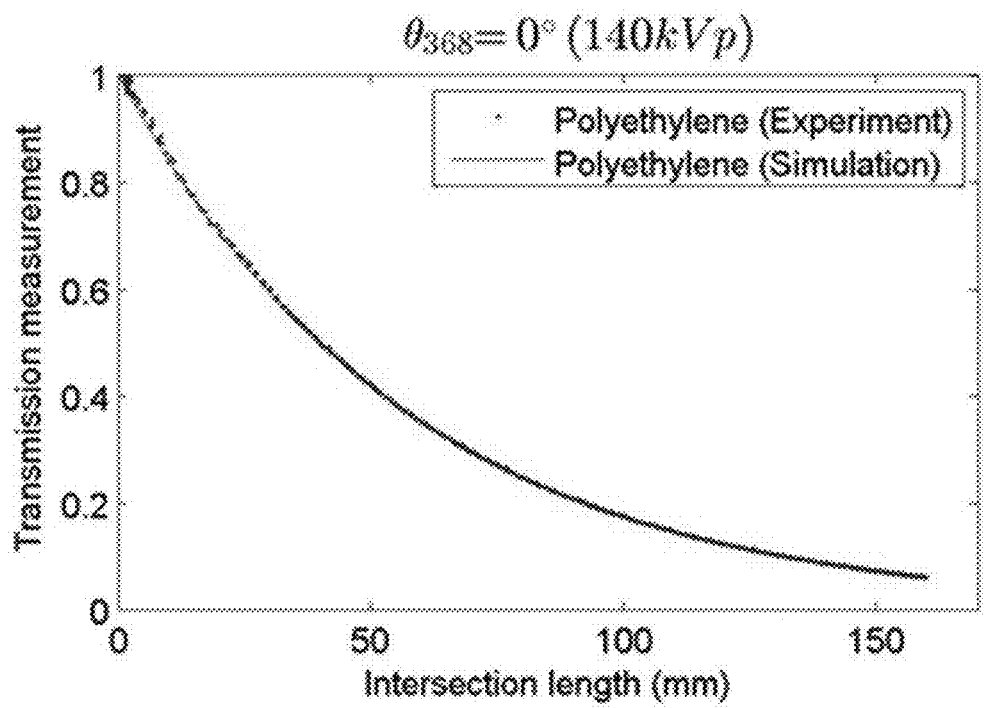

The transmission measurement results for the central detector element ($\theta_{368} = 0°$) at 140 kVp are plotted in FIGS. 45A and 45B, which illustrate graphs of a comparison of the experimental results and the simulated results in terms of the transmission measurement as a function of the intersection length for the central detector element ($\theta_{368} = 0°$) at 140 kVp.

FIG. 45A shows the results of the metal filters (i.e., Al and Cu) using the conventional technique, and FIG. 45B shows the results of the polyethylene phantom using the proposed technique. Due to the time consuming nature of the conventional technique, only a single-kVp spot-validation at 140 kVp was employed. Both of the experimental results in FIG. 45A and FIG. 45B yielded a good agreement with the simulation results (solid lines). However, due to the limited number of metal filters, FIG. 45A included fewer measurements. In contrast, the latter figure included more than 900 measurements, to which a high-degree polynomial function could be fitted to reduce the influence of noise and to more accurately represent the transmission measurements. The estimated error for polyethylene (too small to be visualized) was 0.002, determined by computing the standard deviation of the transmission measurements within the 1 mm interval centered at the intersection length of 137 mm.

Figure 46:
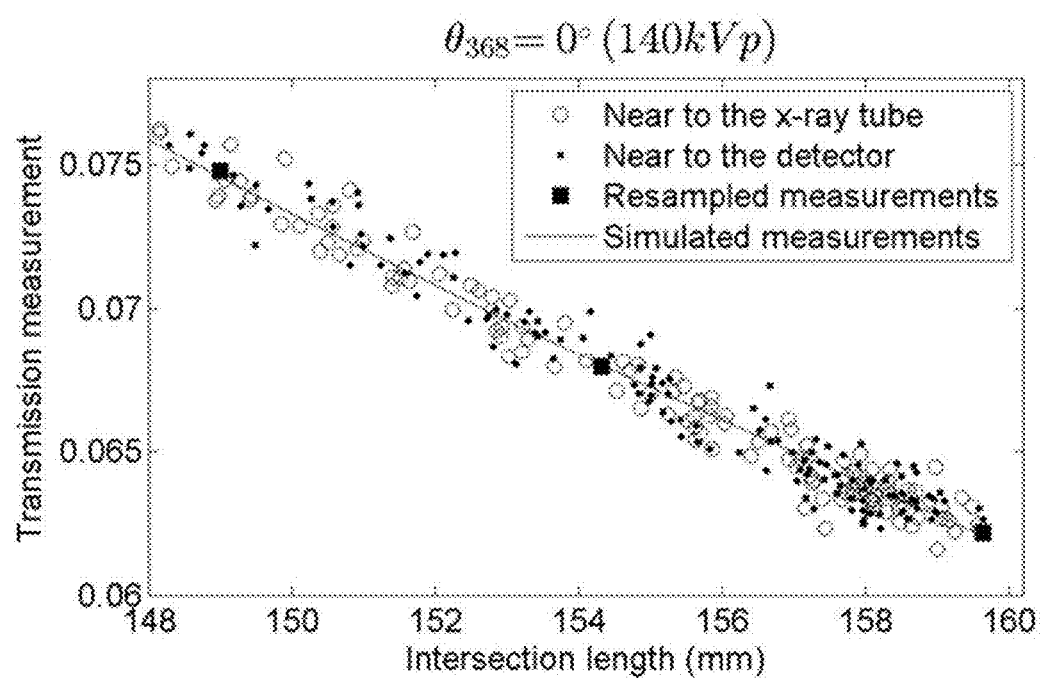
FIG. 46 is a graph showing the transmission measurements acquired by the central detector when the phantom was near to the x-ray tube (circles) and near to the detector (dots)

FIG. 46 is a graph showing the transmission measurements acquired by the central detector when the phantom was near to the x-ray tube (circles) and near to the detector (dots). The resampled measurements after data conditioning procedure were plotted as solid squares. The simulated measurements were plotted as a solid curve. shows the transmission measurements acquired by the central detector at different locations. The circles and dots indicate the data acquired when the phantom was near to the x-ray tube and the detector, respectively. Due to the built-in scatter reduction techniques (e.g., anti-scatter grid) and the narrow collimation, the influence of the scatter radiation on the measurements could be reduced to negligible levels; both datasets were close to the simulated data (solid line) with no notable difference. The fluctuation of the measured transmission measurements was mainly due to the quantum noise and the finite size of the detector (0.6×0.6 mm$^2$). The latter factor could impact the accuracy of the derived intersection lengths. With our data conditioning procedure, the resampled measurements (solid squares) had a good agreement with the simulated measurements and the fluctuation was significantly suppressed.

Figure 47A:
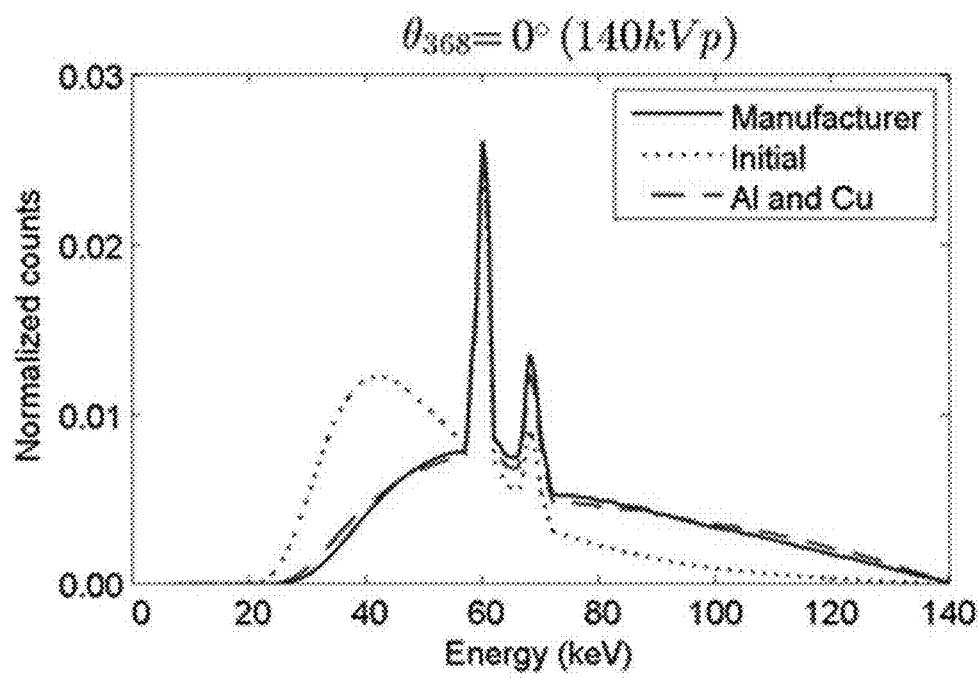
FIGS. 47A and 47B are graphs depicting a comparison of the central spectrum derived from the manufacturer-provided pre-bowtie spectrum, the central spectrum estimated with Al and Cu using the conventional technique, and the central spectrum estimated with polyethylene using the proposed technique.
Figure 47B:
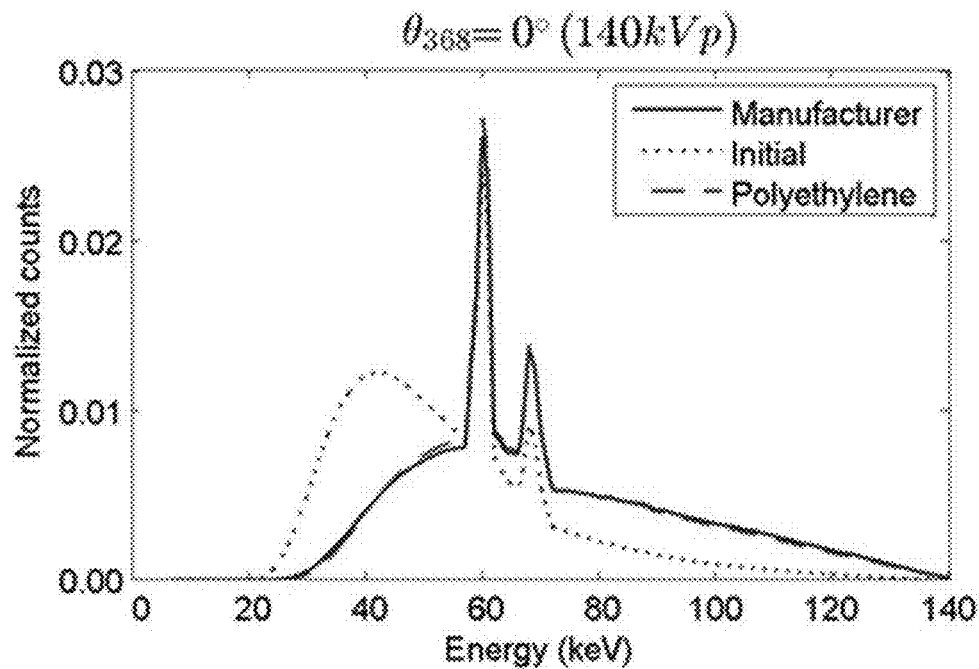
Figure 48A:
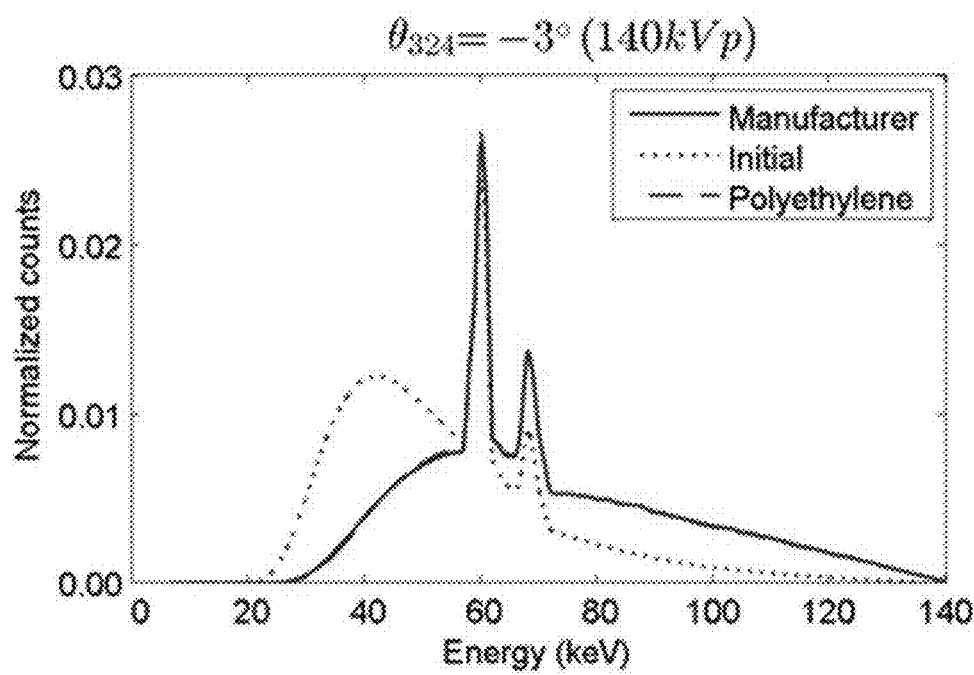
FIGS. 48A-48D are graphs showing a comparison of the spectra derived from the manufacturer-provided pre-bowtie spectra and the spectra estimated with polyethylene from different beam angles.
Figure 48B:
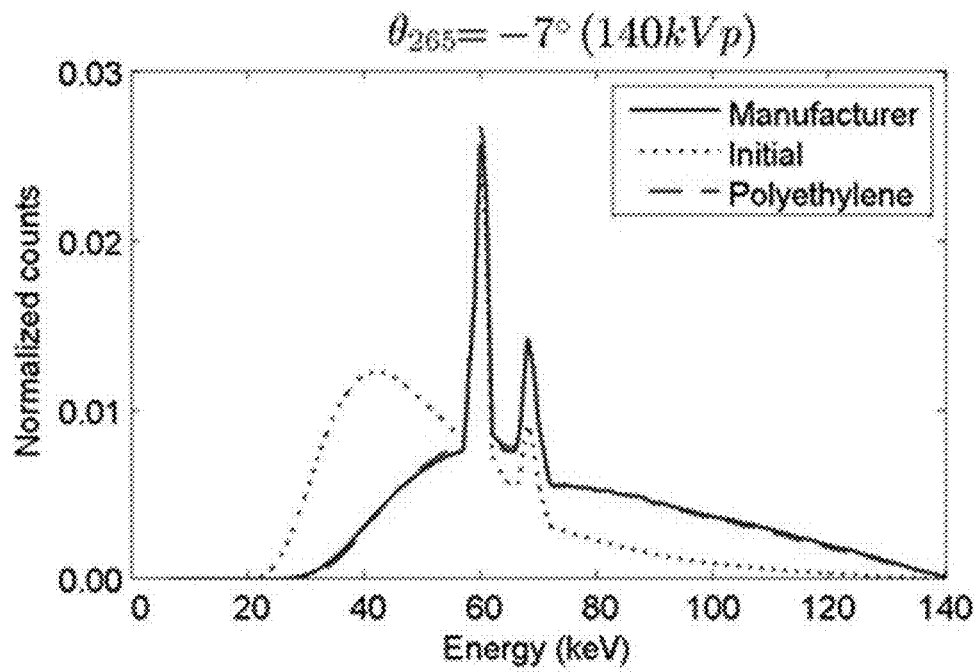
Figure 48C:
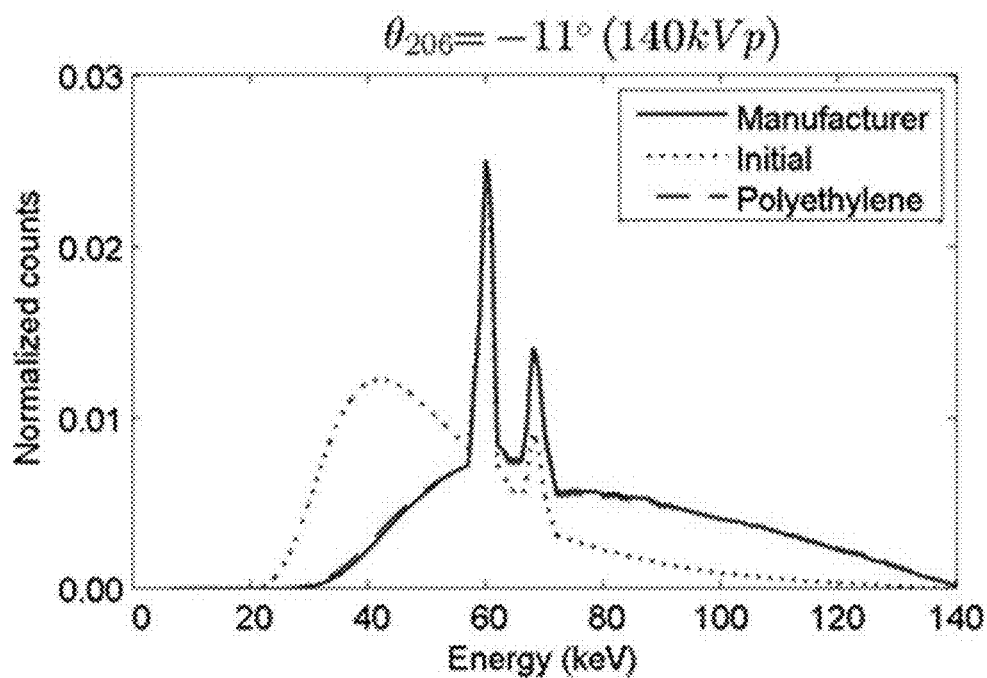
Figure 48D:
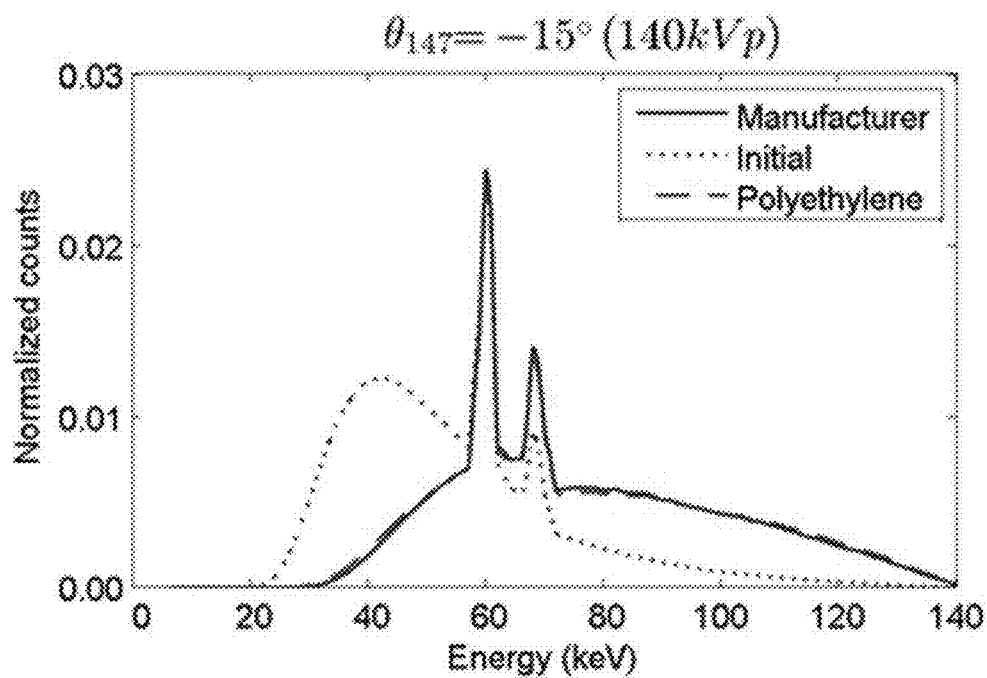

Using the corresponding transmission measurement (FIGS. 45A and 45B), the incident spectrum of the central detector element was estimated and compared with the initial spectrum and the manufacturer-provided spectrum. FIGS. 47A and 47B are graphs depicting a comparison of the central spectrum derived from the manufacturer-provided pre-bowtie spectrum (solid line), the central spectrum estimated with Al and Cu using the conventional technique (dashed line in FIG. 47A), and the central spectrum estimated with polyethylene using the proposed technique (dashed line in FIG. 47B). The same initial spectrum (dotted line) was used by the two techniques.

Table 17 shows a comparison of the two techniques in terms of MED and NRMSD for the incident spectrum of 140 kVp. The results show that the proposed technique (FIG. 47A) yielded spectral estimation comparable to those of the conventional technique (FIG. 47B). Detailed quantitative comparison in terms of MED and NRMSD (Table 17) shows a slightly closer correlation for our results with the manufacturer-provided spectrum.

It is notable that the NRMSD of the conventional technique here was 1.56%, which was much smaller than that in Duan's work (i.e., [4.7%, 8.6%]). This improvement might be due to the use of more reliable reference spectra in this work, which were provided by the manufacturer instead of being simulated with software. The MED value (0.64 keV) was slightly larger than those reported in Duan's work (i.e., [−0.23, 0.55]), but still within the statistical uncertainty.

TABLE 17

| Beam angle | Method | MED (keV) | NRMSD (%) |
|---|---|---|---|
| $\theta_{368} = 0°$ | Conventional technique | 0.64 | 1.56 |
|  | Proposed technique | −0.28 | 0.84 |

With use of techniques in accordance with the disclosed subject matter, the incident spectra for four non-central x-ray trajectories (i.e., $\theta_{324}=-3°$, $\theta_{265}=-7°$, $\theta_{206}=-11°$, $\theta_{147}=-15°$ were estimated and are plotted in FIGS. 48A-48D. Particularly, FIGS. 48A-48D illustrate graphs showing a comparison of the spectra derived from the manufacturer-provided pre-bowtie spectra (solid lines) and the spectra estimated with polyethylene (dashed lines) from different beam angles ((a) $\theta_{324}=-3°$, (b) $\theta_{265}=-7°$, (c) $\theta_{206}=-11°$, and (d) $\theta_{147}=-15°$). The same initial spectrum (dotted line) was used. The reference spectra were derived from the manufacturer-provided spectrum and the bowtie filter. The comparative results show that the estimated spectra accorded well with the reference spectra across different trajectories. The quantitative results in terms of MED and NRMSD are shown in Table 4. The results of the extended angular trajectories (i.e., $\theta_{206}$ and $\theta_{147}$) were within the statistical uncertainty of the results of the non-extended angular trajectories (i.e., $\theta_{324}$ and $\theta_{265}$).

In addition, the beam hardening effect could be observed in these figures, as the photon distribution gradually shifted from low energy to high energy with the increase of the absolute value of the beam angle. This phenomenon can be better appreciated in FIG. 48 where the incident spectra across a wide range of angular trajectories ($\theta_n \in [\theta_{147}, \theta_{368}]=[-15°, 0°]$) were estimated by the proposed technique. From FIGS. 48A-48D, different kVp settings (i.e., 140, 120, 100, and 80 kVp) were used. Particularly, FIGS. 48A-48D are graphs showing a comparison of the spectra derived from the manufacturer-provided pre-bowtie spectra (solid lines) and the spectra estimated with polyethylene (dashed lines) from different beam angles ((a) $\theta_{324}=-3°$, (b) $\theta_{265}=-7°$, (c) $\theta_{206}=-11°$, and (d) $\theta_{147}=-15°$). The same initial spectrum (dotted line) was used.

Table 18 shows a comparison of the estimated spectra from different beam angles in terms of MED and NRMSD for the incident spectrum of 140 kVp.

TABLE 18

| Beam angle | Maximum intersection length (mm) | MED (keV) | NRMSD (%) |
|---|---|---|---|
| $\theta_{324} = -3°$ | 160 | −0.20 | 0.45 |
| $\theta_{265} = -7°$ | 160 | −0.49 | 0.76 |
| $\theta_{206} = -11°$, | 148 | −0.11 | 0.68 |
| $\theta_{147} = -15°$ | 72 | −0.27 | 0.93 |

Figure 49A:
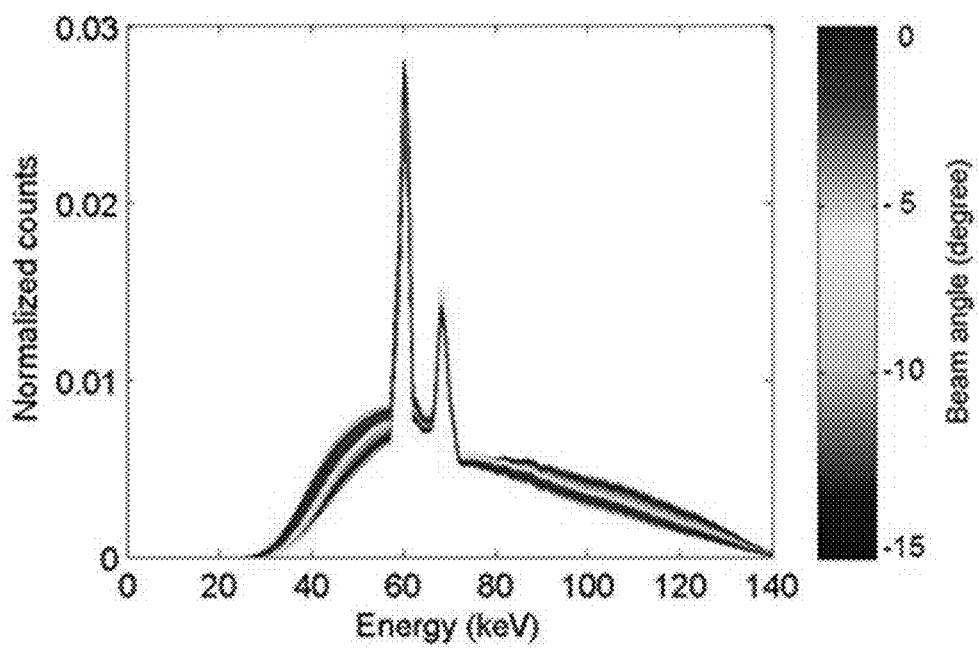
FIGS. 49A-49D depict plots of the estimated spectra from different beam angles with different kVp settings.
Figure 49B:
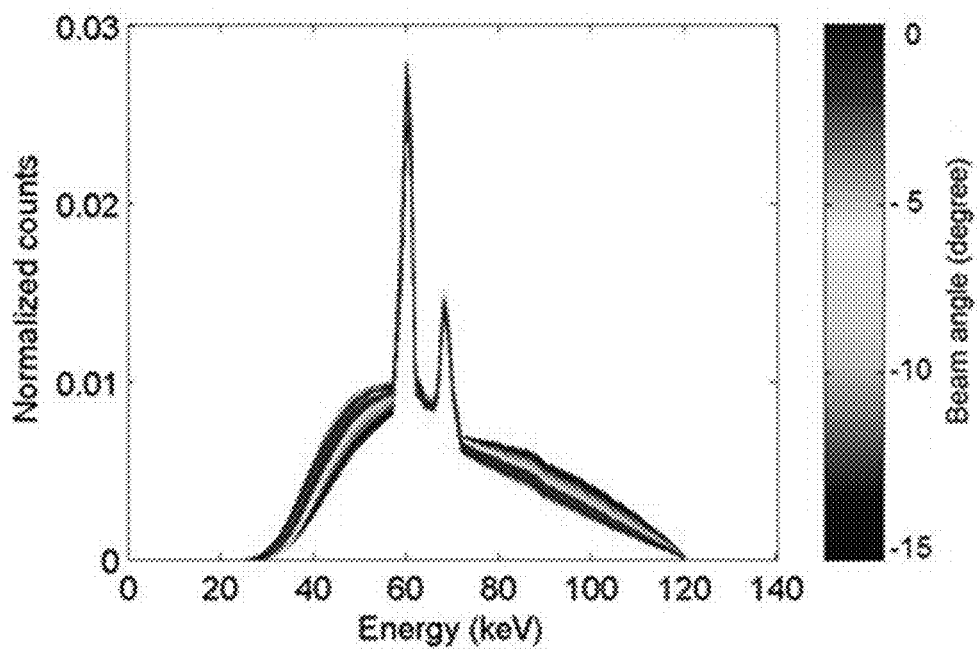
Figure 49C:
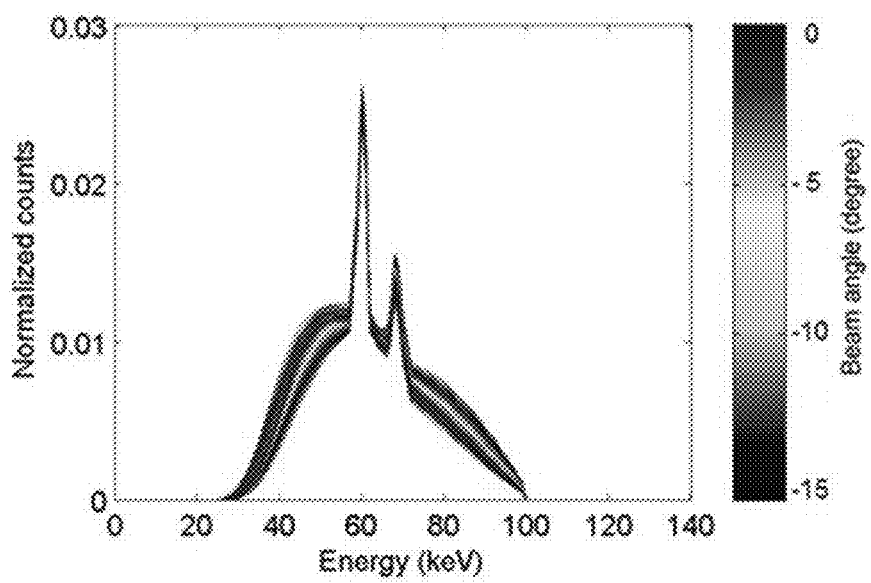
Figure 49D:
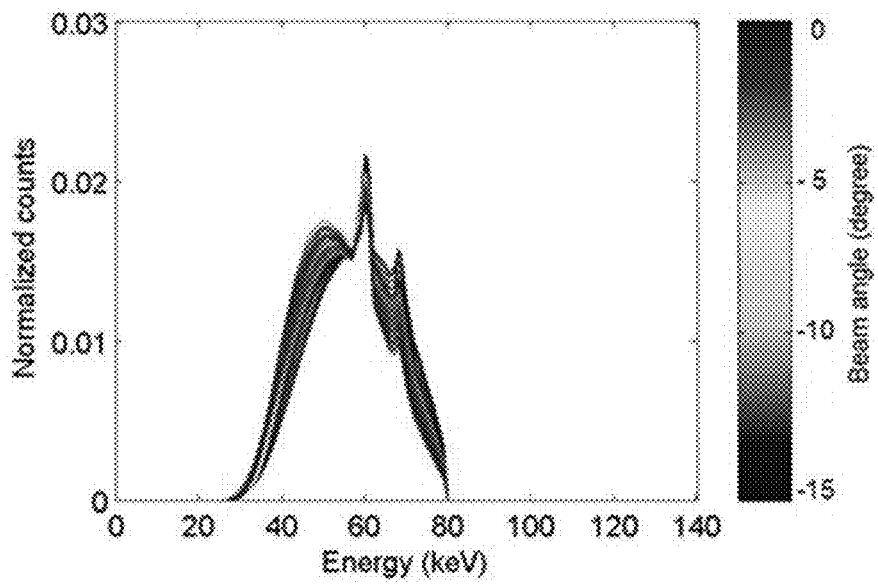

FIGS. 49A-49D depict plots of the estimated spectra from different beam angles ($\theta_n \in [\theta_{147}, \theta_{368}]=[-15°, 0°]$) with different kVp settings, i.e., 140 kVp, (FIG. 49A), 120 kVp (FIG. 49B), 100 kVp (FIG. 49C), and 80 kVp (FIG. 49D). The jet color map was used to differentiate spectra along different angular trajectories.

Figure 50:
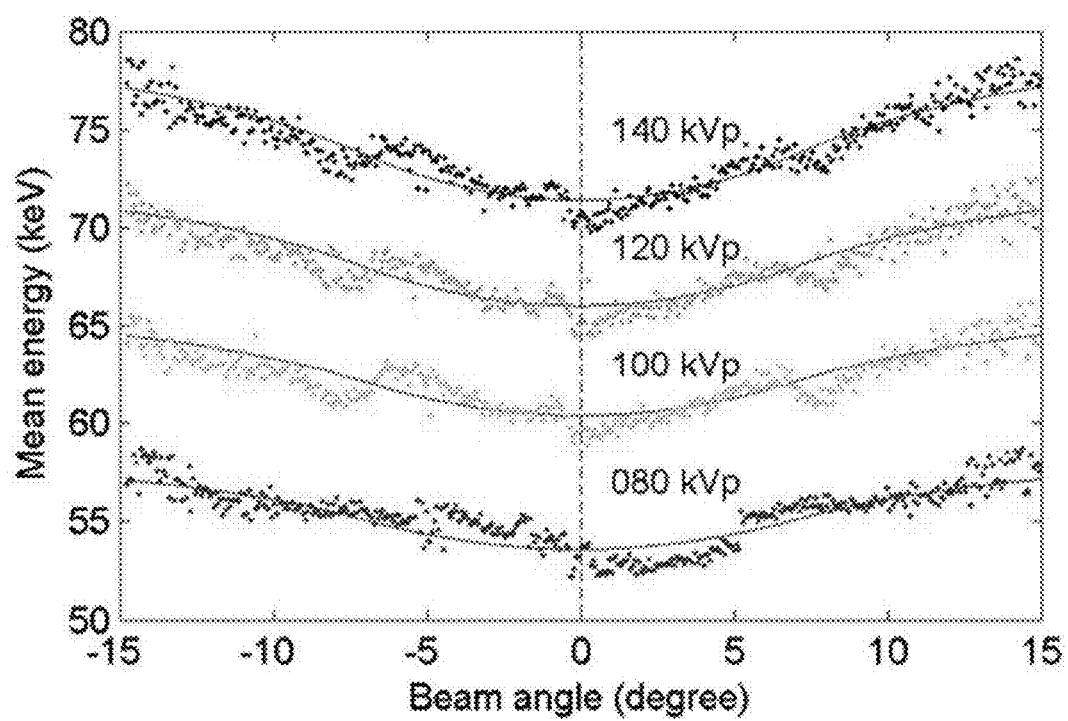
FIG. 50 is a graph showing plots of the mean energy of an incident spectrum as a function of a beam angle.

With the estimated spectra, their corresponding mean energies were evaluated as a function of beam angle (FIG. 50). The mean energies derived from the proposed technique (dots) had an excellent agreement with the mean energies derived from the manufacturer-provided pre-bowtie spectra (solid lines). FIG. 50 illustrates a graph showing plots of the mean energy of the incident spectrum as a function of the beam angle ($\theta_n \in [\theta_{147}, \theta_{589}] = [-15°, 15°]$). The solid lines were derived from the manufacturer-provided spectra; the dots were derived from the proposed technique. From top to bottom, the results were derived from different kVp settings, i.e., 140, 120, 100, and 80 kVp.

Quantitative analysis in terms of the averaged absolute MED, the standard deviation of the MEDs, the averaged NRMSD, and standard deviation of the NRMSDs across the beam angles between [−15°, 15°] for different kVp settings.

The estimation performance of different kVp settings was also assessed (Table 5). The averaged absolute MEDs across the beam angles between [−15°, 15°] of all x-ray tube spectra were less than 0.61 keV with standard deviation less than 0.74 keV. The averaged NRMSDs were less than 3.41% with standard deviation less than 2.02%. These quantities indicate the high estimation accuracy and stability of the proposed technique across different angular trajectories and kVp settings.

With the decrease of the kVp, the averaged NRMSD increased. This is likely due to the decrease in the maximum number of photons in the spectrum, (i.e., max($N_s^*$)=0.026, 0.025, 0.022, 0.016 for 140, 120, 100, 80 kVp, respectively), which magnified the NRMSD values via the normalization process in Equation 71. In addition, with decreased kVp, more photons were attenuated leading to increased contribution of the quantum noise and scatter radiation.

It was observed that the shape of the curves (FIG. 50) had an angle-dependent pattern at higher kVp settings (i.e., 140, 120, and 100 kVp). The mean energies along certain angular trajectories were systematically smaller (e.g., −8° and 8°) or larger (e.g., −6° and −1°) than the simulated mean energies. These patterns were probably caused by systematic errors.

TABLE 18

| Beam angle | Spectrum | Averaged absolute MED (keV) | Standard deviation of the MEDs (keV) | Averaged NRMSD (%) | Standard deviation of the NRMSDs (%) |
|---|---|---|---|---|---|
| [$\theta_{147}$, $\theta_{589}$] = [−15°, 15°] | 140 kVp | 0.53 | 0.66 | 0.89 | 0.64 |
| | 120 kVp | 0.57 | 0.69 | 1.08 | 0.75 |
| | 100 kVp | 0.59 | 0.71 | 1.60 | 1.04 |
| | 80 kVp | 0.61 | 0.74 | 3.41 | 2.02 |

Because of the limited number of the measurements, previous techniques do not have the data conditioning procedure. Therefore, diverse attenuation materials have to be adopted to reduce noise and to improve estimation stability. In comparison, the proposed technique can collect hundreds of transmission measurements for each angular trajectory. With the abundant transmission measurements, polynomial functions with the correct boundary condition can be used to fit the data, which helps reduce the influence of the dramatic change of the intersection lengths derived from the x-ray paths near the edge of the phantom. Therefore, this data conditioning procedure reduces noise and improves both the estimation accuracy and the estimation stability.

An experiment was conducted by comparing the conventional technique and the proposed technique. The results show that, for the incident spectrum of the central beam, the MED and the NRMSD of the proposed technique were both largely comparable to those of the conventional technique. The incident spectra across a wide range of angular trajectories were also estimated. The quantitative results show that the average absolute MED and averaged NRMSD of all kVp settings were smaller than 0.61 keV and 3.41%, respectively, which indicates the high accuracy and stability of the proposed technique across different angular trajectories and kVp settings.

Two types of systematic errors might contribute to the angle-dependent pattern in FIG. 50. The first one is the inherent systematic errors of the detector modules (e.g., gain error, nonlinearity error, and energy sensitivity difference, etc.), as it is impossible to produce identical detector modules in the manufacturing process. An additional possible cause might be due to the unexpected deviation of the bowtie filters.

In experiments, the manufacturer-provided spectra were used as reference spectra, which neglect the possible spectral characteristics of each individual x-ray system and thus cannot be used as a gold standard.

There are several ways by which the method developed in this study can be improved. First, one of the major sources of error in our method is the limited resolution of the detector. This error can be reduced using the flying focal spot technique (FFS), which can improve the resolution from 0.6×0.6 $mm^2$ to 0.3×0.3 mm. Second, while we use a high mAs setting and a data conditioning procedure to reduce the quantum noise, it is possible to further reduce the quantum noise by averaging multiple axial scans. Third, if we use position 2 in FIG. 40, the range of the angular trajectories can be extended to $\theta_n \in [\theta_{17}, \theta_{719}] = [-24°, 24°]$, which almost covers the whole detector range, i.e., [−25°, 25°]. This extension however requires certain accommodations. In order to avoid the influence of the scatter radiation for this position, we can only utilize the transmission measurements acquired near to the x-ray tube for spectral estimation. Fourth, it is straightforward to extend the proposed method to estimate the spectra along the cone-angle (i.e., z direction). However, with the increase of the cone angle, the scatter radiation will also increase and can potentially contaminate the transmission measurements and result in unreliable estimated spectra. If the knowledge of the bowtie filter (i.e., the attenuation properties and the geometry information of the bowtie filter) is available, spectra can be estimated with a narrow fan-beam collimation and then used to derive the spectra along the cone-angle with the knowledge of the bowtie filter. Furthermore, the knowledge of the bowtie filter can be incorporated into the system matrix, such that all measurements can be used to reconstruct a single pre-bowtie spectrum. That spectrum can be used to derive the spectra along any angular trajectory. As this technique uses more data and a prior known knowledge of the bowtie filter, it can potentially yield more precise estimation of the spectra.

Figure 51:
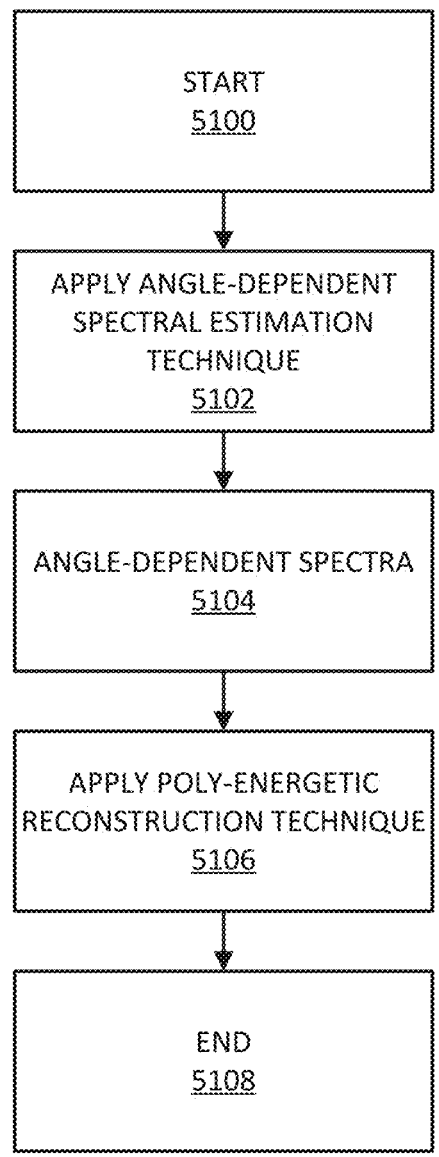
FIG. 51 is a flow chart of an example method for spectral estimation and poly-energetic reconstruction in accordance with embodiments of the present disclosure.

FIG. 51 illustrates a flow chart of an example method for spectral estimation and poly-energetic reconstruction in accordance with embodiments of the present disclosure. It is noted that the method may be implemented by a CT scanner or other suitable imaging equipment that is operably connected with a computing device. The computing device may include suitable hardware, software, and/or firmware for implementing the functionality of the example method or any other functions described herein. Referring to FIG. 51, the example method may start at step 5100.

The method of FIG. 51 includes applying 5102 an angle-dependent spectral estimation technique.

Further, the method of FIG. 51 includes applying 5106 a poly-energetic reconstruction technique using the estimated 5104 angle-dependent spectra. For example, piFBP, pSART, pDP, and other variations of poly-energetic reconstruction techniques that adopt the techniques proposed here. Subsequently, the method may end at step 5108.

Figure 52:
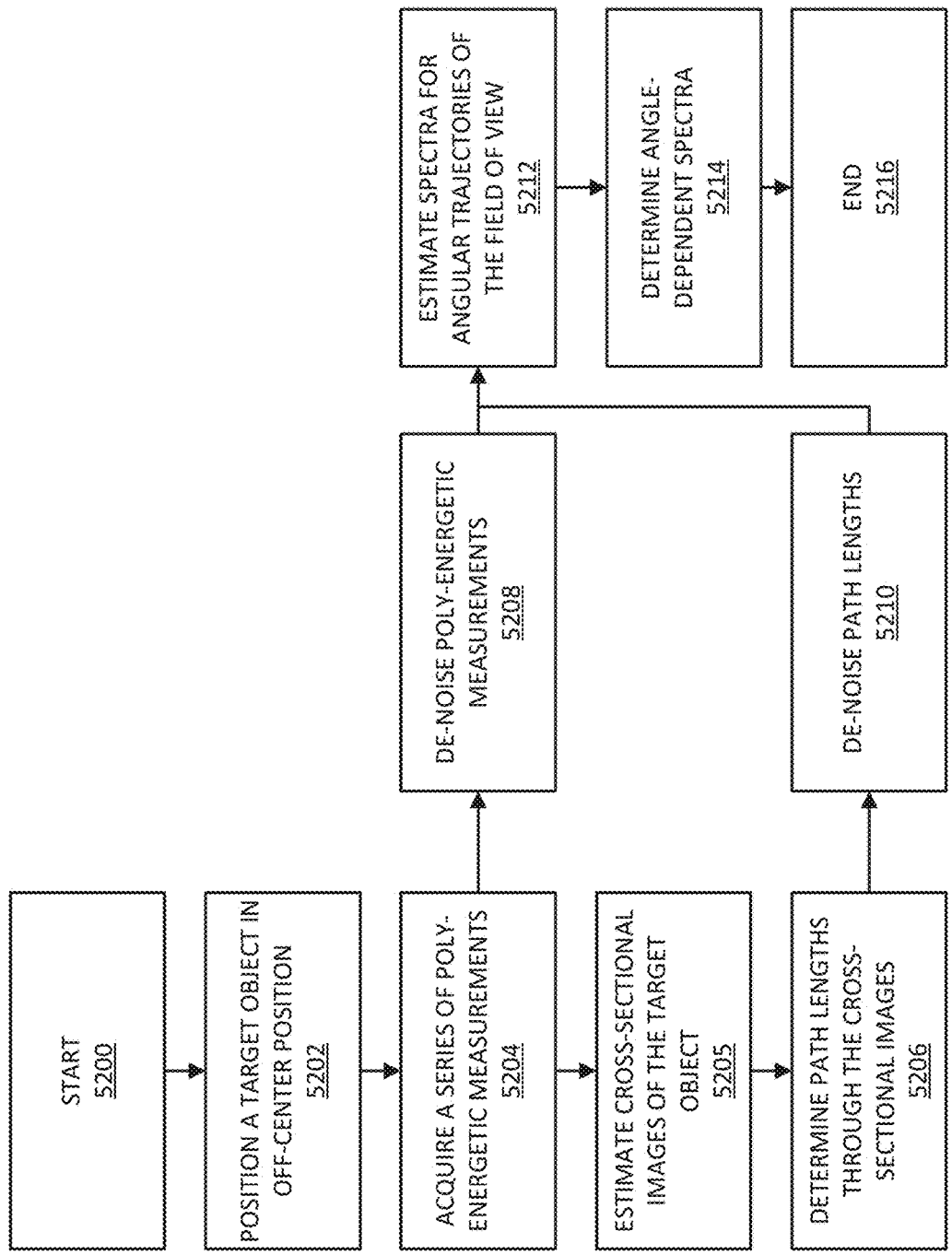
FIG. 52 is a flow chart of an example method for imaging a target object in accordance with embodiments of the present disclosure.

FIG. 52 illustrates a flow chart of an example method for imaging a target object in accordance with embodiments of the present disclosure. It is noted that the method may be implemented by a CT scanner or other suitable imaging equipment that is operably connected with a computing device. The computing device may include suitable hardware, software, and/or firmware for implementing the functionality of the example method or any other functions described herein. Referring to FIG. 52, the example method may start at step 5200.

The method of FIG. 52 includes positioning 5202 a target object in an off-center position. For example, the target objects can be made of but not limited to acrylic and Teflon.

Further, the method of FIG. 52 includes acquiring 5204 a series of poly-energetic measurements.

The method of FIG. 52 includes estimating 5205 cross-sectional images of the target object. For example, the cross-sectional images can be reconstructed using the acquired poly-energetic measurements or a second scan of the target object without collimators or blockers, can be estimated using a backward projection/ray-tracing technique, can be obtained by registering shape and structure information of the target object to measurements, or can be estimated using surface reconstruction techniques (such as structured light techniques or time-of-flight techniques).

The method of FIG. 52 also includes determining 5206 path lengths through the cross-sectional images.

The method of FIG. 52 also includes de-noising 5210 path lengths. For example, curve fitting, data resampling, and fixed point constraint can be applied.

The method of FIG. 52 includes de-noising 5208 poly-energetic measurements. For example, curve fitting, data resampling, and fixed point constraint can be applied.

The method of FIG. 52 includes estimating 5212 spectra for angular trajectories of the field of view.

The method of FIG. 52 includes determining 5214 angle-dependent spectra. Subsequently, the method ends at step 5216.

Figure 53:
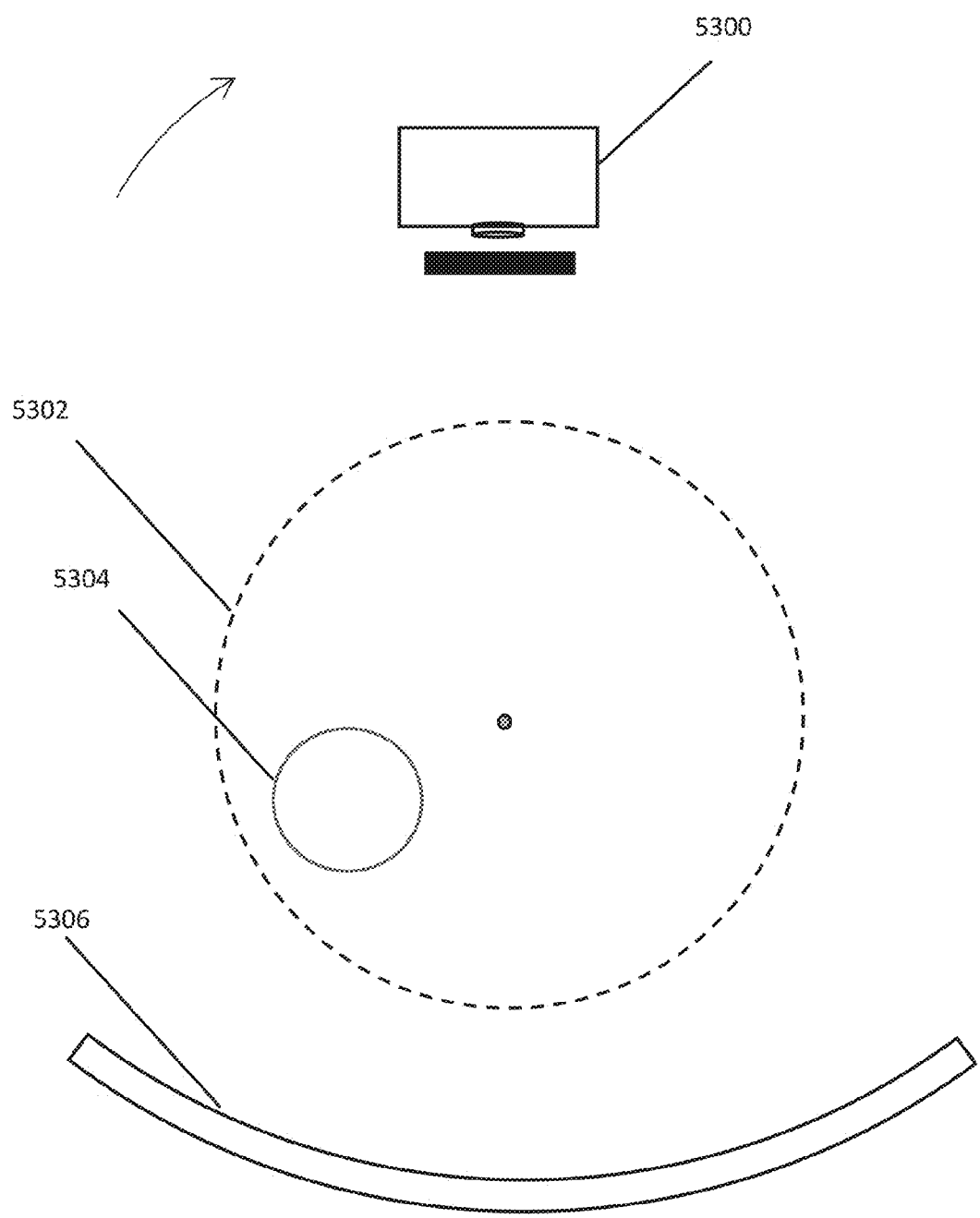
FIG. 53 is a block diagram of an example system for angle-dependent spectral estimation for a CT scanner in accordance with embodiments of the present disclosure.

In accordance with embodiments of the present disclosure, FIG. 53 illustrates a block diagram of an example system for angle-dependent spectral estimation for a CT scanner. Referring to FIG. 53, the system includes 5300 an X-ray tube, 5306 a X-ray detector, 5304 an off-centered target within 5302 the field of view.

Figure 54:
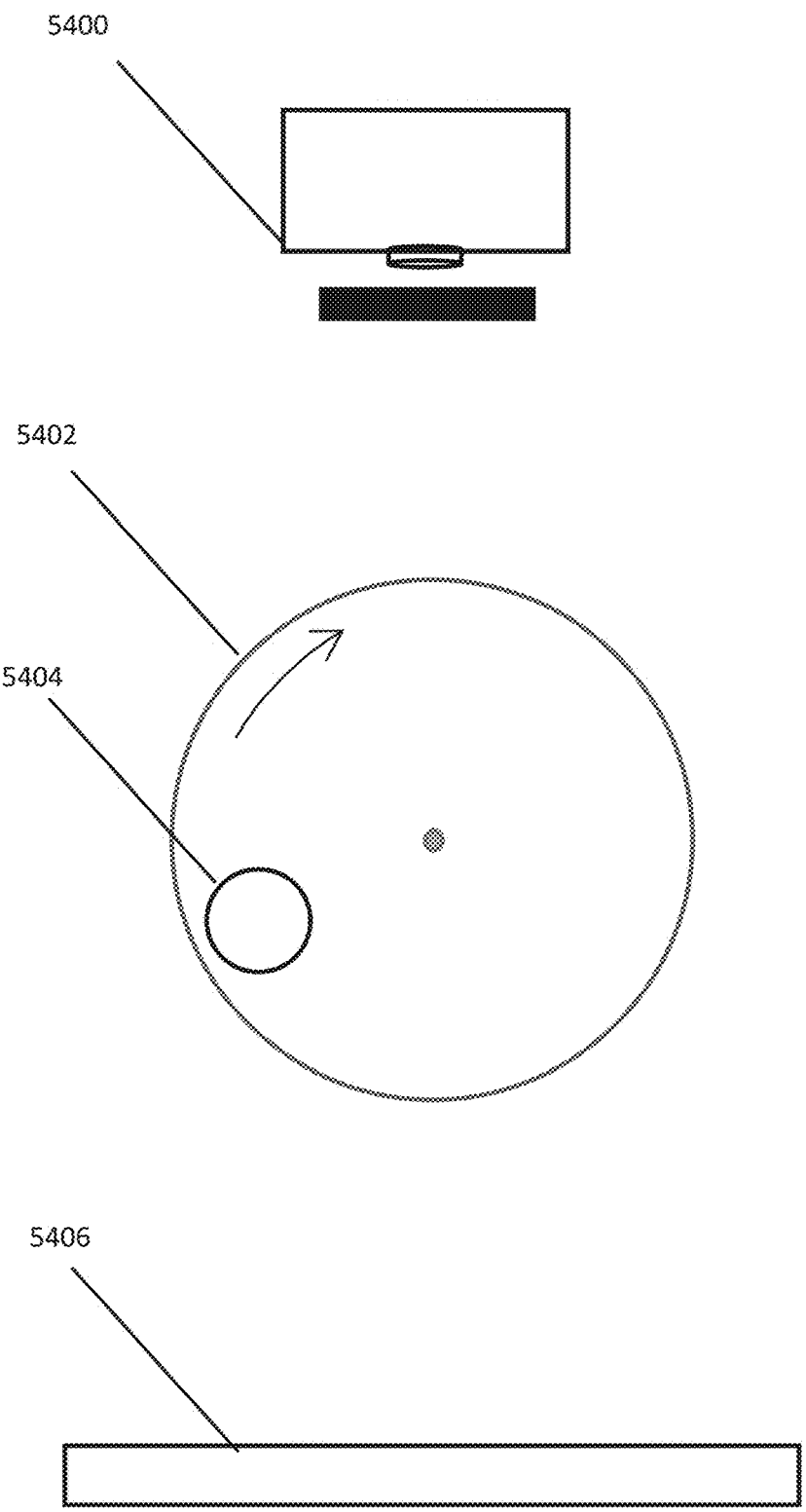
FIG. 54 is a block diagram of an example system for angle-dependent spectral estimation for a CT scanner, radiograph scanner, or tomosynthesis scanner in accordance with embodiments of the present disclosure.

In accordance with embodiments of the present disclosure, FIG. 54 illustrates a block diagram of an example system for angle-dependent spectral estimation for a CT scanner, radiograph scanner, or tomosynthesis scanner. Referring to FIG. 54, the system includes 5400 an X-ray tube, 5406 a X-ray detector, 5404 an off-centered target positioned on 5402 a rotational platform.

FIG. 55 depicts diagrams of examples of collimators and blockers, target objects as indicated. These components may be used in systems in accordance with embodiments of the present disclosure.

Figure 56:
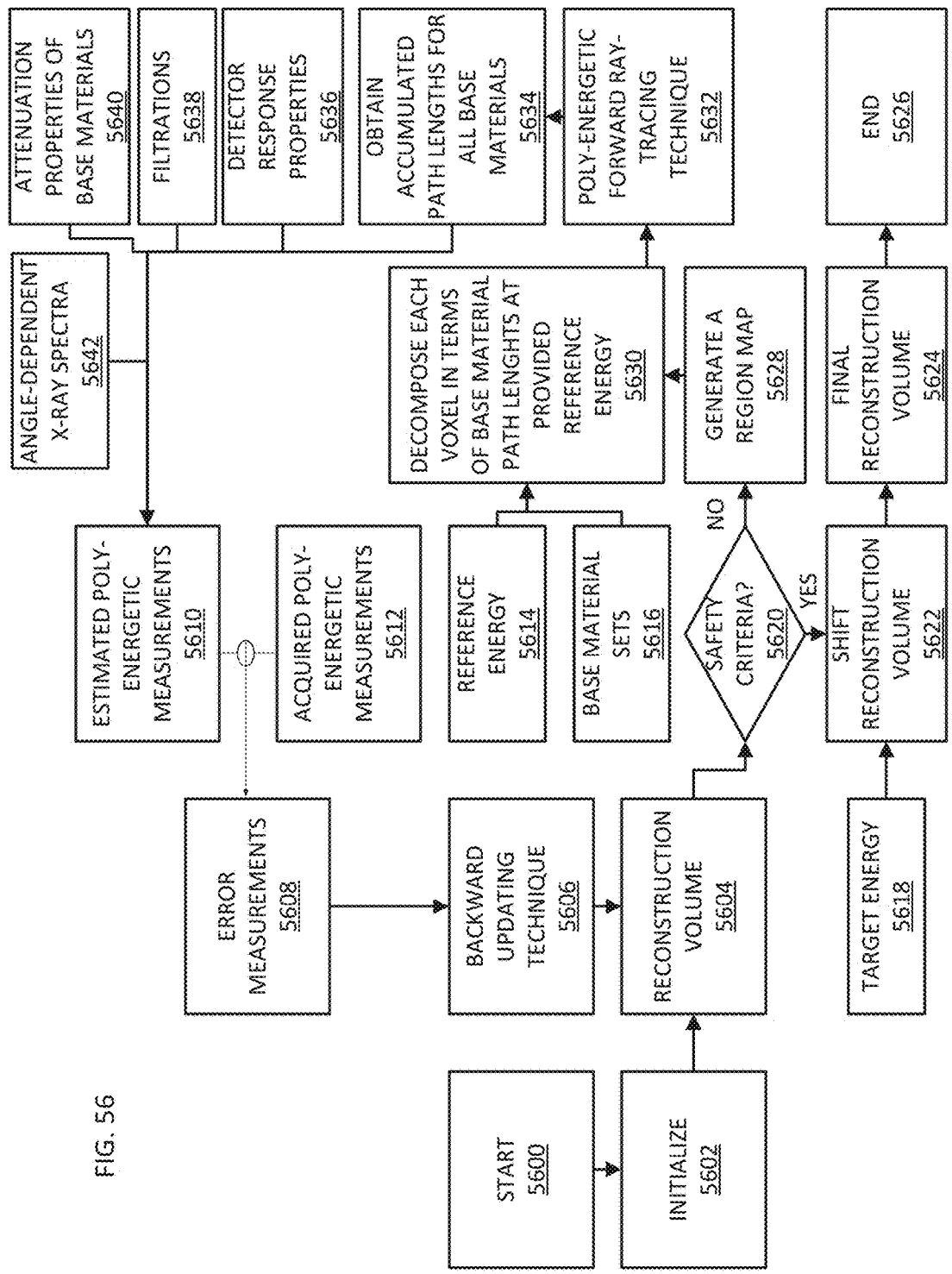
FIG. 56 is a flow chart of an example method for poly-energetic reconstruction in accordance with embodiments of the present disclosure.

FIG. 56 illustrates a flow chart of an example method for poly-energetic reconstruction in accordance with embodiments of the present disclosure. It is noted that the method may be implemented by a CT scanner or other suitable imaging equipment that is operably connected with a computing device. The computing device may include suitable hardware, software, and/or firmware for implementing the functionality of the example method or any other functions described herein. Referring to FIG. 56, the example method may start at step 5600.

The method of FIG. 52 includes initializing 5602 the reconstruction volume 5604. For example, the reconstruction volume can be initialize with zeros or can be reconstructed with conventional reconstruction algorithms (such as FBP, SART, etc.).

The method of FIG. 52 includes generating 5628 a region map.

The method of FIG. 52 includes decomposing 5630 each voxel in terms of base material path lengths at provided reference energy 5614 according to the base material set that is corresponding to its location in the generated region map 5628.

The method of FIG. 52 includes performing 5632 poly-energetic forward ray-tracing technique.

The method of FIG. 52 includes 5634 obtaining the accumulated path lengths for all base materials.

The method of FIG. 52 includes estimating 5620 poly-energetic measurements using angle-dependent spectra 5642, attenuation properties of base materials 5640, filtrations 5638, detector response properties 5636, and obtained accumulated path lengths of all base materials 5634.

The method of FIG. 52 includes obtaining 5608 error measurements by subtracting the estimated poly-energetic measurements 5610 from the acquired poly-energetic measurements 5612.

The method of FIG. 52 includes using 5606 backward updating technique and the error measurements 5608 to correct the reconstruction volume 5604. For example, the backward updating technique can be is one of filtered back projection (FBP), an algebraic reconstruction technique (ART), a simultaneous algebraic reconstruction technique (SART), simultaneous iterative reconstruction technique (SIRT), and a statistical reconstruction algorithm.

The method of FIG. 52 includes checking whether the reconstruction volume meets the predetermined criteria 5602. If no, performing another iterations to refine the reconstruction volume; if yes, shifting 5622 the reconstruction volume based on the provided target energy 5618 to the final reconstruction volume 5624, and the method ends at step 5626.

Figure 57:
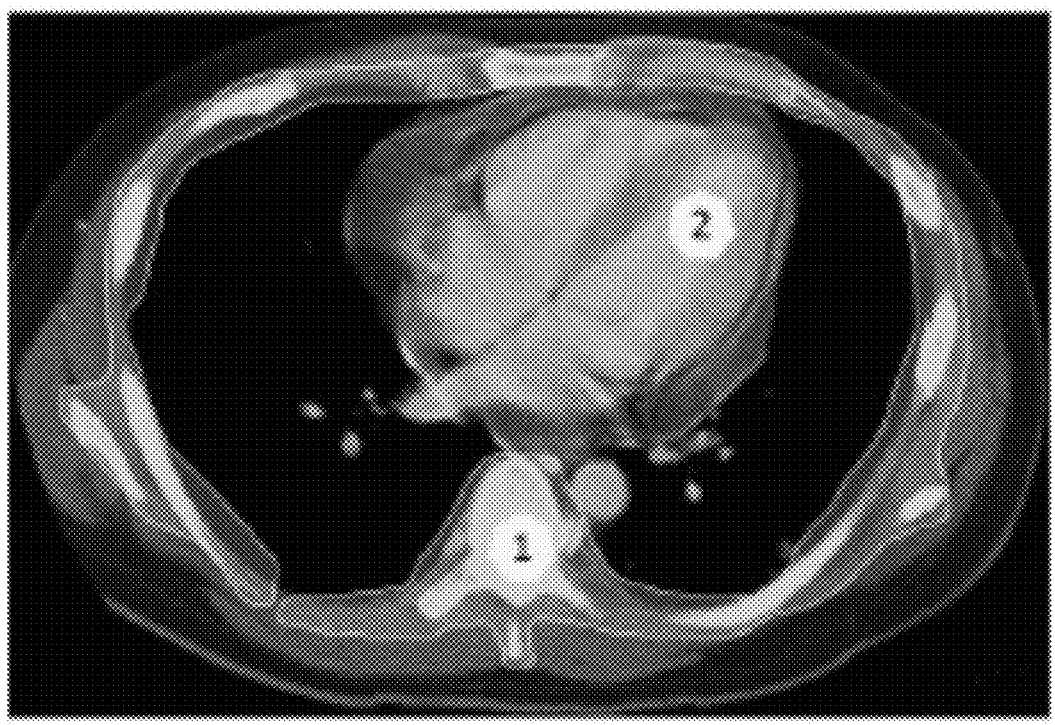
FIG. 57 is an image of an example region map having two regions.

FIG. 57 illustrates an image of an example region map having two regions. The base material set of region 1 possesses air, soft tissue, and, bone. The base material set of region 2 possesses air, soft tissue, and contrast agent.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A spectral estimation method comprising:
   generating, using a plurality of poly-energetic x-ray sources, x rays; directing, using a processor, the generated x-rays towards a target object;
   acquiring, by a processor, a series of poly-energetic measurements of x-rays from the target object;
   estimating, by the processor, cross-sectional images of the target object based on the poly-energetic measurements;
   determining, by the processor, path lengths through the cross-sectional images;
   determining, by the processor, de-noised poly-energetic measurements and de-noised path lengths based on the acquired poly-energetic measurements and the determined path lengths; and
   estimating, by the processor, spectra for angular trajectories of a field of view based on the de-noised poly-energetic measurements and the path lengths, wherein estimating spectra comprises using the following iterative algorithm:

$$I_s^{(k)} = \frac{I_s^{(k-1)}}{\sum_m A_{m,s}} \sum_m \frac{A_{m,s} Y_m}{\sum_{s'} A_{m,s'} I_{s'}^{(k-1)}}, m = 1, \ldots, N_M, s = 1, \ldots, N_S,$$

where
$Y_m$=de-noised poly-energetic measurements,
$N_M$=total number of transmission measurements,
k=kth iteration,
$I_s$=photon,
$N_S$=total number of samplings of the spectrum, and
  $A_{m,s}$=system matrix element comprising the information of de-noised path lengths, material attenuation coefficients or mass attenuation coefficients and material density distribution, and spectral interval; and
  reconstructing, by the processor, a volume based on the angle dependent spectra by executing the iterative algorithm, whereby executing the iterative algorithm increases reconstruction and convergence speed at the processor.

2. The spectral estimation method of claim 1, wherein acquiring the series of poly-energetic measurements comprises acquiring the series of poly-energetic measurements which the target object is one of stationary and moving.

3. The spectral estimation method of claim 1, further comprising positioning the target object off-center among the directed x-rays.

4. The spectral estimation method of claim 1, further comprising applying a scatter correction algorithm for reducing scattered radiation from the target object.

5. The spectral estimation method of claim 1, wherein estimating cross-sectional images comprises reconstructing the poly-energetic measurements, and
  wherein reconstructing the poly-energetic measurements comprises using one of filtered back projection (FBP), algebraic reconstruction technique (ART), simultaneous algebraic reconstruction technique (SART), simultaneous iterative reconstruction technique (SIRT), and a statistical reconstruction algorithm to reconstruct the poly-energetic measurements.

6. The spectral estimation method of claim 1, wherein estimating cross-sectional images comprises using a backward projection/ray-tracing technique to delineate a shape of the target object.

7. The spectral estimation method of claim 1, wherein estimating cross-sectional images comprises registering shape and structure information of the target object to measurements.

8. The spectral estimation method of claim 1, further comprising determining one or more of attenuation coefficients, mass attenuation coefficients, and material density distribution of at least one of material of the target object.

9. A spectral estimation system comprising:
  a plurality of poly-energetic x-ray sources configured to generate x-rays and to direct the x-rays towards a target object;
  detectors configured to acquire a series of poly-energetic measurements of x-rays from the target object; and
  a computing device comprising a memory and processor, wherein the processor is configured to:
    estimate cross-sectional images of the target object based on the poly-energetic measurements;
    determine path lengths through the cross-sectional images;
    determine de-noised poly-energetic measurements and de-noised path lengths based on the acquired poly-energetic measurements and the determined path lengths; and
    estimate spectra for angular trajectories of a field of view based on the de-noised poly-energetic measurements and the path lengths,
  wherein estimating spectra comprises using the following iterative algorithm:

$$I_s^{(k)} = \frac{I_s^{(k-1)}}{\sum_m A_{m,s}} \sum_m \frac{A_{m,s} Y_m}{\sum_{s'} A_{m,s'} I_{s'}^{(k-1)}}, m = 1, \ldots, N_M, s = 1, \ldots, N_S,$$

where
$Y_m$=de-noised poly-energetic measurements,
$N_M$=total number of transmission measurements,
k=kth iteration,
$I_s$=photon,
$N_S$=total number of samplings of the spectrum, and
  $A_{m,s}$=system matrix element comprising the information of de-noised path lengths, material attenuation coefficients or mass attenuation coefficients and material density distribution, and spectral interval; and
  reconstruct a volume based on the angle dependent spectra by executing the iterative algorithm, whereby executing the iterative algorithm increases reconstruction and convergence speed at the processor.

10. A poly-energetic reconstruction method comprising:
  providing a plurality of acquired poly-energetic measurements, a reference energy for reconstruction, and an initialized reconstruction volume;
  providing one or more base material sets;
  generating a region map based on a current reconstruction volume;
  decomposing each voxel of the current reconstruction volume into a plurality of base materials in terms of based material path lengths based on the provided reference energy, a voxel value of the reconstruction volume, the region map, and the corresponding base material set;
  performing a forward poly-energetic, ray-tracing technique to estimate poly-energetic measurements based on the current reconstruction volume;
  subtracting estimated poly-energetic measurements from the acquired poly-energetic measurements to obtain error measurements;
  performing a backward updating technique to update the current reconstruction volume based on a difference between the estimated poly-energetic measurements and acquired poly-energetic measurements;
  iterating the steps of providing one or more based material sets, initializing, and generating for one of a predetermined number of iterations or until the reconstruction volume converges and meets predetermined criteria, whereby the iterating step increases reconstruction speed at the processor; and
  transforming a finalized reconstruction volume from the reference energy to the target energy.

11. The poly-energetic reconstruction method of claim 10, wherein the reference energy comprises selecting proper reference energy to accelerate the speed of the reconstruction.

12. The poly-energetic reconstruction method of claim 10, further comprising adaptively changing the base material set based on an acquisition phase of a computed tomography (CT) exam, and wherein adaptively changing the base material set comprises adding, in perfusion CT, contrast agent materials for the poly-energetic reconstruction in a post-contrast phase.

13. The poly-energetic reconstruction method of claim 10, wherein generating a region map comprises using one of a segmentation technique and information about structure of a scanned object.

14. The poly-energetic reconstruction method of claim 10, wherein the region map is associated with a reconstruction volume having a single region.

15. The poly-energetic reconstruction method of claim 10, wherein decomposing each voxel comprises linearly decomposing each voxel to two adjacent base materials in the corresponding base material set at the provided reference energy.

16. The poly-energetic reconstruction method of claim 10, wherein the forward poly-energetic ray-tracing technique comprises:
integrating the base material path lengths of the voxels along x-ray paths to obtain accumulated path lengths for all base materials; and
computing the estimated poly-energetic measurements using the accumulate path lengths and computed tomography (CT) scanner properties.

17. The poly-energetic reconstruction method of claim 10, further comprising applying noise suppression to obtain the error measurements.

18. The poly-energetic reconstruction method of claim 10, further comprising using base material path lengths of each voxel to estimate the derivatives of the poly-energetic measurements with respect to the voxel values.

19. The poly-energetic reconstruction method of claim 10, wherein transforming the reconstruction volume comprises shifting a value of each voxel according to attenuation coefficient properties of the base materials in the base material set corresponding to the voxel.

* * * * *